United States Patent
Gierahn et al.

(10) Patent No.: US 12,071,663 B2
(45) Date of Patent: Aug. 27, 2024

(54) SEMI-PERMEABLE ARRAYS FOR ANALYZING BIOLOGICAL SYSTEMS AND METHODS OF USING SAME

(71) Applicant: MASSACHUSETTS INSTITUTE OF TECHNOLOGY, Cambridge, MA (US)

(72) Inventors: Todd M. Gierahn, Brookline, MA (US); J. Christopher Love, Somerville, MA (US); Travis K. Hughes, Cambridge, MA (US); Marc H. Wadsworth, II, Cambridge, MA (US); Alexander K. Shalek, Lexington, MA (US); Shaina Carroll, Cambridge, MA (US)

(73) Assignee: Massachusetts Institute of Technology, Cambridge, MA (US)

(*) Notice: Subject to any disclaimer, the term of this patent is extended or adjusted under 35 U.S.C. 154(b) by 1010 days.

(21) Appl. No.: 16/070,505

(22) PCT Filed: Jan. 17, 2017

(86) PCT No.: PCT/US2017/013791
§ 371 (c)(1),
(2) Date: Jul. 16, 2018

(87) PCT Pub. No.: WO2017/124101
PCT Pub. Date: Jul. 20, 2017

(65) Prior Publication Data
US 2019/0144936 A1 May 16, 2019

Related U.S. Application Data

(60) Provisional application No. 62/279,500, filed on Jan. 15, 2016.

(51) Int. Cl.
*B01J 19/00* (2006.01)
*C12Q 1/6874* (2018.01)

(52) U.S. Cl.
CPC ........ *C12Q 1/6874* (2013.01); *B01J 19/0046* (2013.01); *B01J 2219/00572* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 5,972,694 A * | 10/1999 | Mathus ............... B01L 3/50255 422/534 |
| 6,033,880 A | 3/2000 | Haff et al. |
| 6,524,456 B1 | 2/2003 | Ramsey et al. |
| 6,617,145 B2 | 9/2003 | Boone et al. |
| 7,041,481 B2 | 5/2006 | Anderson et al. |
| 7,129,091 B2 | 10/2006 | Ismagilov et al. |
| 7,708,949 B2 | 5/2010 | Stone et al. |
| 7,776,553 B2 | 8/2010 | Love et al. |
| RE41,780 E | 9/2010 | Anderson et al. |
| 8,273,573 B2 | 9/2012 | Ismagilov et al. |
| 8,304,193 B2 | 11/2012 | Ismagilov et al. |
| 8,329,407 B2 | 12/2012 | Ismagilov et al. |
| 8,658,430 B2 | 2/2014 | Miller et al. |
| 8,772,049 B2 | 7/2014 | Love et al. |
| 8,822,148 B2 | 9/2014 | Ismagliov |
| 8,835,187 B2 | 9/2014 | Love et al. |
| 8,835,358 B2 | 9/2014 | Fodor et al. |
| 8,865,479 B2 | 10/2014 | Love et al. |
| 8,889,083 B2 | 11/2014 | Ismagilov et al. |
| 9,089,844 B2 | 7/2015 | Hiddessen et al. |
| 9,126,160 B2 | 9/2015 | Ness et al. |
| 9,216,392 B2 | 12/2015 | Hindson et al. |
| 9,290,808 B2 | 3/2016 | Fodor et al. |
| 9,290,809 B2 | 3/2016 | Fodor et al. |
| 9,315,857 B2 | 4/2016 | Fu et al. |
| 9,347,059 B2 | 5/2016 | Saxonov |
| 9,388,465 B2 | 7/2016 | Hindson et al. |
| 9,500,664 B2 | 11/2016 | Ness et al. |
| 9,567,631 B2 | 2/2017 | Hindson et al. |
| 9,567,645 B2 | 2/2017 | Fan et al. |
| 9,567,646 B2 | 2/2017 | Fan et al. |
| 9,598,736 B2 | 3/2017 | Fan et al. |
| 9,636,682 B2 | 5/2017 | Hiddessen et al. |
| 9,637,799 B2 | 5/2017 | Fan et al. |

(Continued)

FOREIGN PATENT DOCUMENTS

| | | |
|---|---|---|
| EP | 2047910 A2 | 4/2009 |
| EP | 2 297 333 A1 | 3/2011 |

(Continued)

OTHER PUBLICATIONS

AeraSeal™ (Excel Scientific webpage rendered Jul. 26, 2021).*
AeraSeal™ (Excel Scientific webpage II rendered Mar. 27, 2022).*
SECO (Scientific Equipment Company web pages rendered: Sep. 14, 2022) (Year: 2022).*
Lu et al (Biomedical Materials 4 044103 (5pp)) (Year: 2009).*
Chung, et al., "Statistical Significance of Variables Driving Systematic Variation in High-Dimensional Data", Bioinformatics, vol. 31, No. 4, pp. 545-554, Advance Access publication: Oct. 21, 2014.
Collins, "Biomedical Research Highlighted in Science's 2018 Breakthroughs", NIH Director's Blog, pp. 1-9, Jan. 8, 2019.
Corbo, et al., "A Typology of Photoreceptor Gene Expression Patterns in the Mouse", PNAS, vol. 104, Issue 29, pp. 12069-12074, Jul. 17, 2007.

(Continued)

*Primary Examiner* — Christopher M Gross
(74) *Attorney, Agent, or Firm* — F. Brent Nix, Esq.; Johnson, Marcou, Isaacs & Nix, LLC

(57) ABSTRACT

The present application provides a method of assembling a container for one or multiple parallel steps of biochemical analysis on one or more cells comprising performing molecular bonding of a porous membrane on an apical or basal surface of an array having a plurality of wells, wherein the molecular bonding substantially isolates each well from adjacent wells.

49 Claims, 36 Drawing Sheets

(56) References Cited

U.S. PATENT DOCUMENTS

| | | | |
|---|---|---|---|
| 9,644,204 | B2 | 5/2017 | Hindson et al. |
| 9,649,635 | B2 | 5/2017 | Hiddessen et al. |
| 9,689,024 | B2 | 6/2017 | Hindson et al. |
| 9,695,468 | B2 | 7/2017 | Hindson et al. |
| 9,708,654 | B2 | 7/2017 | Hunicke-Smith et al. |
| 9,708,659 | B2 | 7/2017 | Fodor et al. |
| 9,816,121 | B2 | 11/2017 | Agresti et al. |
| 9,816,137 | B2 | 11/2017 | Fodor et al. |
| 9,826,137 | B2 | 11/2017 | Yokomizo |
| 9,845,502 | B2 | 12/2017 | Fodor et al. |
| 9,856,530 | B2 | 1/2018 | Hindson et al. |
| 9,885,034 | B2 | 2/2018 | Saxonov |
| 2002/0172965 | A1 | 11/2002 | Kamb et al. |
| 2005/0172476 | A1 | 8/2005 | Stone et al. |
| 2005/0260135 | A1* | 11/2005 | Baranski ............ A01K 67/0339 424/9.2 |
| 2007/0195127 | A1 | 8/2007 | Ahn et al. |
| 2008/0003142 | A1 | 1/2008 | Link et al. |
| 2008/0014589 | A1 | 1/2008 | Link et al. |
| 2009/0042737 | A1 | 2/2009 | Katz et al. |
| 2010/0002241 | A1 | 1/2010 | Hirose |
| 2010/0022414 | A1 | 1/2010 | Link et al. |
| 2010/0137163 | A1 | 6/2010 | Link et al. |
| 2010/0172803 | A1 | 7/2010 | Stone et al. |
| 2011/0111981 | A1 | 5/2011 | Love et al. |
| 2011/0116992 | A1 | 5/2011 | North |
| 2011/0281745 | A1* | 11/2011 | Love ................... B01L 3/50853 506/9 |
| 2011/0319298 | A1 | 12/2011 | Benner et al. |
| 2012/0015824 | A1 | 1/2012 | Love et al. |
| 2012/0122714 | A1 | 5/2012 | Samuels et al. |
| 2012/0141562 | A1* | 6/2012 | Achneck ................ A61P 7/02 424/400 |
| 2012/0149592 | A1 | 6/2012 | Love et al. |
| 2012/0219947 | A1 | 8/2012 | Yurkovetsky et al. |
| 2012/0220494 | A1 | 8/2012 | Samuels et al. |
| 2013/0274117 | A1 | 10/2013 | Church et al. |
| 2014/0093738 | A1* | 4/2014 | Bimanand .......... C08G 18/4277 428/425.9 |
| 2014/0155295 | A1 | 6/2014 | Hindson et al. |
| 2014/0235506 | A1 | 8/2014 | Hindson et al. |
| 2014/0357500 | A1 | 12/2014 | Vigneault et al. |
| 2015/0005199 | A1 | 1/2015 | Hindson et al. |
| 2015/0011430 | A1 | 1/2015 | Saxonov |
| 2015/0299784 | A1* | 10/2015 | Fan ..................... C12Q 1/6881 506/4 |
| 2018/0030515 | A1 | 2/2018 | Regev et al. |

FOREIGN PATENT DOCUMENTS

| | | |
|---|---|---|
| JP | 571822 A | 1/1982 |
| WO | 02099078 A2 | 12/2002 |
| WO | 2004002627 A2 | 1/2004 |
| WO | 2004016767 A2 | 2/2004 |
| WO | 2005003291 A2 | 1/2005 |
| WO | 2007089541 A2 | 8/2007 |
| WO | 2009036379 A2 | 3/2009 |
| WO | 2013188872 A1 | 12/2013 |
| WO | 2014026032 A2 | 2/2014 |
| WO | 2014047561 A1 | 3/2014 |
| WO | WO 2015/031691 A1 | 3/2015 |
| WO | 2016040476 A1 | 3/2016 |
| WO | 2017/124101 A | 7/2017 |

OTHER PUBLICATIONS

Cuatrecasas, Pedro, "Protein Purification by Affinity Chromatography", J Biol Chem, vol. 245, Issue 12, pp. 3059-3065, Jun. 25, 1970.
Damha, et al., "An improved procedure for derivatization of controlled-pore glass beads for solid-phase oligonucleotide synthesis", Nucleic Acids Res., vol. 18, No. 13, pp. 3813-3821, Accepted: May 17, 1990.
Descamps, et al., "Gelatinase B/matrix Metalloproteinase-9 Pprovokes Cataract by Cleaving Lens BetaB 1 Crystallin", The FASEB Journal, vol. 19, Issue 1, pp. 29-35, Jan. 2005.
Ding, et al., "Progress Towards a Systematic Comparison of Single Cell RNA-Seq Methods", Broad Institute, Feb. 12, 2019.
Dixit, et al., "Perturb-Seq: Dissecting Molecular Circuits with Scalable Single-Cell RNA Profiling of Pooled Genetic Screens", Cell, vol. 167, Issue 7, pp. 1853-1866, Dec. 15, 2016.
Dobin, et al., "Star: Ultrafast Universal RNA-seq Aligner", Bioinformatics, vol. 29, Issue 1, pp. 15-21, Advance Access publication: Oct. 25, 2012.
Dressman, et al., "Transforming single DNA molecules into fluorescent magnetic particles for detection and enumeration of genetic variations", PNAS, vol. 100, No. 15, pp. 8817-8822, Jul. 22, 2003.
Droege, et al., "The Genome Sequencer FLX System—longer reads, more applications, straight forward bioinformatics and more complete data sets.", J Biotechnol., vol. 136, Issues 1-2, pp. 3-10, Accepted: Mar. 31, 2008.
Edd, et al., "Controlled Encapsulation of Single Cells into Monodisperse Picoliter Drops", Lab Chip, vol. 8, Issue 8, pp. 1262-1264, Aug. 2008.
Ester, et al., "A Density-Based Algorithm for Discovering Clusters in Large Spatial Databases with Noise", pp. 226-231, KDD-96, 1996.
Farmer, et al., "Defining epithelial cell dynamics and lineage relationships in the developing lacrimal gland", Development, The Company of Biologists, vol. 144, Issue 13, pp. 2517-2528, Accepted: May 31, 2017.
Feigenspan, et al., "Expression of Neuronal Connexin36 in All Amacrine Cells of the Mammalian Retina", The Journal of Neuroscience, vol. 21, Issue 1, pp. 230-239, Jan. 1, 2001.
Gao, et al., "Secondary structure effects on DNA hybridization kinetics: a solution versus surface comparison", Nucleic Acids Research, 2006, vol. 34, No. 11, pp. 3370-3377, Accepted: May 27, 2006.
Glatthar, et al., "A New Photocleavable Linker in Solid-Phase Chemistry for Ether Cleavage", Org. Lett. 2000, vol. 2, No. 15, pp. 2315-2317, Received: May 18, 2000.
Greenfieldboyce, "Biological cartographers seek to map the trillions of cells in the human body", NPR, pp. 1-5, Jan. 5, 2019.
Greer, et al., "Linked read sequencing resolves complex genomic rearrangements in gastric cancer metastases", Genome Medicine, vol. 9, No. 57, pates 1-17, 2017.
Gueroult, et al., "How Cations Can Assist DNase I in DNA Binding and Hydrolysis", PLoS Comput Biol., vol. 6, Issue 11:e1001000, pp. 1-11, Nov. 18, 2010.
Haber, et al., "A single-cell survey of the small intestinal epithelium", Nature, vol. 551, No. 7680, pp. 333-339, Nov. 16, 2017.
Hamady, et al., "Error-correcting barcoded primers for pyrosequencing hundreds of samples in multiplex", Nature Methods, vol. 5, No. 3, pp. 235-237, Mar. 2008.
Hamady, et al., "Microbial community profiling for human microbiome projects: Tools, techniques, and challenges", Genome Res., vol. 19, No. 7, pp. 1141-1152, ISSN 1088-9051/09, Jul. 2009.
He, et al., "High-resolution crystal structures reveal plasticity in the metal binding site of apurinic/apyrimidinic endonuclease I.", Biochemistry, vol. 53, No. 41, pp. 6520-6529, Published: Sep. 24, 2014.
Hoffmann, et al., "DNA bar coding and pyrosequencing to identify rare HIV drug resistance mutations", Nucleic Acids Res., vol. 35, No. 13, e91, pp. 1-8, Published online: Jun. 18, 2007.
Holmberg, et al., "The biotin-streptavidin interaction can be reversibly broken using water at elevated temperatures.", Electrophoresis, vol. 26, No. 3, pp. 501-510, Feb. 2005.
Islam, et al., "Quantitative single-cell RNA-seq with unique molecular identifiers", Nature Methods, , vol. 11, No. 2, pp. 163-166, Feb. 2014.
Kaiser, et al., "Huge trove of British biodata is unlocking secrets of depression, sexual orientation, and more", Science | AAAS, pp. 1-12, Jan. 3, 2019.
Kovall, et al., "Structural, functional, and evolutionary relationships between exonuclease and the type II restriction endonucleases", Proc Natl Acad Sci U S A., vol. 95, No. 14, pp. 7893-7897, Jul. 1998.

(56) References Cited

OTHER PUBLICATIONS

Kumaresan, et al., "High-Throughput Single Copy DNA Amplification and Cell Analysis in Engineered Nanoliter Droplets", Anal. Chem., vol. 80, No. 10, pp. 3522-3529, May 15, 2008.
Kutnjak, et al., "Calorimetric study of octylcyanobiphenyl liquid crystal confined to a controlled-pore glass.", Physical Review E, The American Physical Society, pp. 021705-1-021705-12, Published: Aug. 22, 2003.
Litosh, et al., "Improved nucleotide selectivity and termination of 3'-OH unblocked reversible terminators by molecular tuning of 2-nitrobenzyl alkylated HOMedU triphosphates.", Nucleic Acids Res., vol. 39, No. 6, pp. 1-13, Published online: Jan. 11, 2011.
Macosko, et al., "Highly Parallel Genome-Wide Expression Profiling of Individual Cells Using Nanoliter Droplets", Cell, vol. 161, No. 5, pp. 1202-1214, May 21, 2015.
Malone, et al., "Bringing Renal Biopsy Interpretation Into the Molecular Age With Single-Cell RNA Sequencing", Seminars in Nephrology, vol. 38, Issue 1, pp. 1-17, Author Manuscript; available in PMC: Jan. 1, 2019.
Margulies, et al., "Genome Sequencing in Open Microfabricated High Density Picoliter Reactors", Nature, vol. 437, No. 7057, pp. 376-380, Sep. 15, 2005.
McKenna, et al., "The Macaque Gut Microbiome in Health, Lentiviral Infection, and Chronic Enterocolitis", PLoS Pathog., vol. 4, Issue 2, e20, pp. 0001-0012, Feb. 8, 2008.
Metzker, "Emerging technologies in DNA sequencing.", Genome Res., vol. 15, No. 12, pp. 1767-1776, Dec. 2005.
Miller, et al., "Basic Concepts of Microarrays and Potential Applications in Clinical Microbiology", Clinical Microbiology Reviews, vol. 22, No. 4, pp. 611-633, Oct. 2009.
Mol, et al., "DNA-bound structures and mutants reveal abasic DNA binding by APE1 and DNA repair coordination.", Nature, vol. 403, No. 6768, pp. 451-456, Jan. 27, 2000.
Narasimhan, et al., "Health and population effects of rare gene knockouts in adult humans with related parents", Science, vol. 352, No. 6284, pp. 474-477, Apr. 22, 2016.
Nguyen, "Optical detection for droplet size control in microfluidic droplet-based analysis systems", Nguyen et al., Optical detection for droplet size control in microfluidic droplet-based analysis systems, 117 Sensors and Actuators B 117, pp. 431-436, Available online: Jan. 18, 2006.
Novak, et al., "Single cell multiplex gene detection and sequencing with microfluidically generated agarose emulsions", Angew. Chem. Int. Ed., pp. 1-11, 2010.
Novak, et al., "Single Cell Multiplex Gene Detection and Sequencing with Microfluidically Generated Agarose Emulsions", Agnew. Chem. Int. Ed., pp. 390-395, Jan. 10, 2011.
Pal, et al., "Construction of developmental lineage relationships in the mouse mammary gland by single-cell RNA profiling", Nature Communications, vol. 8, Article No. 1627, pp. 1-14, Nov. 20, 2017.
Parameswaran, et al., "A pyrosequencing-tailored nucleotide barcode design unveils opportunities for large-scale sample multiplexing", Nucleic Acids Res., vol. 35, No. 19, e130, pp. 1-9, Published online: Oct. 11, 2007.
Pennisi, "Development Cell by Cell", Science, vol. 362, Issue 6421, pp. 1344-1345, Dec. 21, 2018.
Perona, "Type II restriction endonucleases.", Methods, vol. 28, No. 3, pp. 353-364, Accepted: Jul. 30, 2002.
Peterson, et al., "The effect of surface probe density on DNA hybridization", Nucleic Acids Res., vol. 29, No. 24, pp. 5163-5168, Dec. 15, 2001.
Qi, et al., "Digital analysis of the expression levels of multiple colorectal cancer-related genes by multiplexed digital-PCR coupled with hydrogel bead-array.", Analyst, vol. 136, No. 11, pp. 2252-2259, Accepted: Mar. 11, 2011.
Final Office Action for U.S. Appl. No. 15/453,405, issued by the U.S. Patent Office on Mar. 27, 2019, 17 pages.
Massachusetts Institute of Technology, "Communication Pursuant to Article 94(3) EPC for EP 17705198.4", Jul. 9, 2020, 5 pages.
"Markman Order in re Certain Microfluidic Systems and Components Thereof and Products Containing Same", Docket Alarm, pp. 1-6, Oct. 31, 2018.
"Molecular and Genomics Core Facility Equipment", Molecular and Genomics Core Facility, pp. 1-7, 2018.
"N,N'-Methylenebis(acrylamide)", 146072 Sigma-Aldrich, CAS No. 110-26-9, 2018.
"Neuroscience 2017 Program", Society for Neuroscience, pp. 1-2, 2017.
"Notice of Intent to Certify Sole Source", Sole Source Certification No. SS5098 for Bio-Rad ddSeq Single Cell Isolation System and associated accessories, pp. 1-5, Jun. 5, 2017.
"Nucleic Acid Sample Preparation for Downstream Analyses", GE Healthcare Life Sciences Manual, pp. 1-168, 2009.
"Omniscript Reverse Transcription Handbook", Qiagen, pp. 1-32, Oct. 2010.
"Phosphate-buffered saline (PBS)", pdb.rec8247-, Cold Spring Harbor Protocols (2006).
"Powerful New Tool for Genome Analysis", Georgia Tech Bioinformatics, pp. 1-3, Nov. 14, 2017.
"Q Sepharose High Performance SP Sepharose High Performance", GE Healthcare, Data File 18-1172-88 AB, pp. 1-8, Apr. 2006.
"Research Highlights: Human Cell Atlas", Human Cell Atlas | Broad Institute, pp. 1-4, Jan. 8, 2019.
"Restriction Endonucleases Technical Guide", BioLabs Inc., pp. 1-24, Aug. 2015.
"Reverse Transcription Reaction Setup—Seven Important Considerations", ThermoFisher Scientific, pp. 1-15, 2018.
"Sequencing Power for Every Scale Systems for every application. For every lab.", Illumina, pp. 1-70, 2016.
"Single-Cell RNA Data Analysis Workflow RNA analysis from single cells using the Illumina Bio-Rad Single-Cell Sequencing Solution with the BaseSpace® SureCell™ RNA Single-Cell App.", illumina | Bio-Rad, pp. 1-4, 2017.
"Single-cell RNAseq (Biorad/Illumina ddSEQ)", UNC School of Medicine, pp. 1-3, 2018.
"SITC 2017 Scientific Highlights—Nov. 11", The Sentinel—The Official Blog of the Society for Immunotherapy of Cancer (SITC)., pp. 1-4, Nov. 12, 2017.
"SureCell WTA 3' Library Prep Kit Support, Questions & Answers", Illumina, pp. 1-4, 2019.
"SureCell WTA 3' Library Prep Kit for the ddSEQ System", Ilumina, pp. 1-6, 2019.
"The Illumina Bio-Rad Single Cell Sequencing Solution", illumina | Bio-Rad, pp. 1-3, 2018.
"The Illumina Bio-Rad Single-Cell Sequencing Solution Robust and scalable single-cell sequencing", illumina | Bio-Rad, pp. 1-4, 2016.
"Top 10 Innovations 2015", The Scientist, pp. 1-12, Dec. 1, 2015.
"Transcriptor Reverse Transcriptase", Roche, Ver. 13, pp. 1-13, Jun. 2017.
"Types of Restriction Endonucleases", pp. 1-2, 2018.
U.S. Office Action issued in copending U.S. Appl. No. 15/453,405, filed Aug. 28, 2018, Aug. 28, 2018, 16 pages.
"University of Mississippi Medical Center, Molecular and Genomics Core Facility, Service Home", pp. 1-2, 2018.
"Genomics Resources Core Facility", Weill Cornell Medicine, pp. 1-5, 2018.
Abate, et al., "Beating Poisson encapsulation statistics using close-packed ordering", Lab Chip, vol. 9, pp. 2628-2631, Accepted: Jul. 24, 2009.
Adamson, et al., "A multiplexed single-cell CRISPR screening platform enables systematic dissection of the unfolded protein response", Cell., vol. 167, Issue 7, pp. 1867-18822, Dec. 15, 2016.
International Search Report and Written Opinion issued in International Application No. PCT/US2015/049178, mailed on Feb. 22, 2016, 18 pages.
Andersen, et al., "A Quantitative Study of the Human Cerebellum with Unbiased Stereological Techniques", The Journal of comparative neurology, vol. 326, Issue 4, pp. 549-560, Dec. 22, 1992.
Ascoli, et al., "Petilla Terminology: Nomenclature of Features of GABAergic Interneurons of the Cerebral Cortex", Nature reviews Neuroscience, vol. 9, pp. 557-568, Jul. 2008.

(56) References Cited

OTHER PUBLICATIONS

International Preliminary Report on Patentability issues in International Application No. PCT/US2015/049178, mailed on Mar. 23, 2017, 12 pages.
Barany, Francis, "Genetic Disease Detection and DNA Amplification Using Cloned Thermostable Ligase", PNAS, vol. 88, Issue 1, pp. 189-193, Jan. 1991.
Barany, Francis, "The Ligase Chain Reaction in a PCR World", PCR Methods and Applications, vol. 1, pp. 5-16, 1991.
Bar-Joseph, et al., "Genome-Wide Transcriptional Analysis of the Human Cell Cycle Identifies Genes Differentially Regulated in Normal and Cancer Cells", PNAS, vol. 105, Issue 3, pp. 955-960, Jan. 22, 2008.
Barres, et al., "Immunological, Morphological, and Electrophysiological Variation Among Retinal Ganglion Cells Purified by Panning", Neuron, vol. 1, Issue 9, pp. 791-803, Nov. 1988.
Beer, et al., "On-Chip Single-Copy Real-Time Reverse-Transcription PCR in Isolated Picoliter Droplets", Analytical Chemistry, vol. 80, Issue 6, pp. 1854-1858, Mar. 15, 2008.
Bentley, et al., "Accurate whole human genome sequencing using reversible terminator chemistry.", Nature, 456 (7218), pp. 53-59, Nov. 6, 2008.
Berman, et al., "Mapping the Stereotyped Behaviour of Free Moving Fruit Flies", Journal of the Royal Society Interface, vol. 11, Issue 99, 20140672, pp. 1-12, Aug. 20, 2014.
Binladen, et al., "The Use of Coded PCR Primers Enables High-Throughput Sequencing of Multiple Homolog Amplification Products by 454 Parallel Sequencing", PLoS One; vol. 2, Issue 2: e197, pp. 1-9, Feb. 14, 2007.
Bitinaite, et al., "User™ friendly DNA engineering and cloning method by uracil excision", Nucleic Acids Res. , vol. 35, No. 6, pp. 1992-2002, Publised online Mar. 6, 2007.
Black, Chris, "The Chromium™ System: Linked Read and Single Cell RNA-Seq Applications Powered by GemCode Technology", 10X Genomics, pp. 1-57, Jul. 17, 2017.
Bochet, Christian G., "Photolabile protecting groups and linkers", J. Chem. Soc., Perkin Trans. 1, 2002,0, pp. 125-142, First published as an Advance Article on the Web: Dec. 13, 2001.
Brennecke, et al., "Accounting for Technical Noise in Single-Cell RNA-seq Experiments", Nature methods, vol. 10, Issue 11, 1093-1095, Sep. 22, 2013.
Bringer, et al., "Microfluidic Systems for Chemical Kinetics that Rely on Chaotic Mixing in Droplets", Philosophical Transactions of the Royal Society a Mathematical Physical and Engineering Sciences, vol. 362, Issue 1818, pp. 1087-1104, Jun. 2004.
Britten, et al., "Repeated Sequences in DNA. Hundreds of Thousands of Copies of DNA Sequences have been Incorporated into the Genomes of Higher Organisms", Science, vol. 161, Issue 3841, pp. 529-540, Aug. 9, 1968.
Brouzes, et al., "Droplet Microfluidic Technology for Single-Cell High-Throughput Screening", Proceedings of the National Academy of Sciences, vol. 106, No. 34, pp. 14195-14200, Aug. 25, 2009.
Brown, et al., "Chemical Synthesis and Cloning of a Tyrosine tRNA Gene", Methods in Enzymology, vol. 68, pp. 109-151, 1979.
Buettner, et al., "Computational Analysis of Cell-to-Cell Heterogeneity in Single-Cell RNA-Sequencing Data Reveals Hidden Subpopulations of Cells", Nature Biotechnology, vol. 33, Issue 2, pp. 155-160, Feb. 2015.
Rothberg, et al., "An integrated semiconductor device enabling non-optical genome sequencing", Nature, vol. 475, pp. 348-352, Jul. 21, 2011.
Shimkus, et al., "A chemically cleavable biotinylated nucleotide: usefulness in the recovery of protein-DNA complexes from avidin affinity columns.", Proc Natl Acad Sci U S A., vol. 82, No. 9, pp. 2593-2597, May 1985.
Song, et al., "A Microfluidic System for Controlling Reaction Networks in Time", Angew. Chem. Int. Ed. 2003, vol. 42, No. 7, pp. 767-772, ,Received: Sep. 6, 2002.

Soumillon, et al., "Characterization of Directed Differentiation by High-Throughput Single-Cell RNA-Seq", BioRxiv, pp. 1-13, Preprint: Mar. 5, 2014.
Spies, et al., "Genome-wide reconstruction of complex structural variants using read clouds", Nat Methods, vol. 14, No. 9, pp. 915-920, Sep. 2017.
Stoeckius, et al., "Large-scale simultaneous measurement of epitopes and transcriptomes in single cells", Nature Methods, vol. 14, No. 9, pp. 865-868, Sep. 2017.
Taylor, et al., "A scalable high-throughput method for RNA-Seq analysis of thousands of single cells", illumina | Bio-Rad, 2016.
Tewhey, et al., "Microdroplet-based PCR enrichment for large-scale targeted sequencing", Nature Biotechnology, vol. 27, No. 11, pp. 1025-1031, Nov. 1, 2009.
The Broad Institute, Inc., "Communication Pursuant to Rule 164(2)(b) and Article 94(3) EPC", Jul. 11, 2018, 12 pages.
Tice, et al., "Formation of Droplets and Mixing in Multiphase Microfluidics at Low Values of the Reynolds and the Capillary Numbers", Langmuir, vol. 19, No. 22, pp. 9127-9132, Published on Web: Aug. 12, 2003.
Wilson, "Ape1 abasic endonuclease activity is regulated by magnesium and potassium concentrations and is robust on alternative DNA structures.", J Mol Biol., vol. 345, No. 5, pp. 1003-1014, Feb. 4, 2005.
Wu, et al., "Termination of DNA synthesis by N6-alkylated, not 3'-O-alkylated, photocleavable 2'-deoxyadenosine triphosphates", Nucleic Acids Res., vol. 35, No. 19, pp. 6339-6349, Sep. 18, 2007.
Yan, et al., "Intestinal enteroendocrine lineage cells possess homeostatic and injury-inducible stem cell activity", Cell Stem Cell, vol. 21, No. 1, pp. 78-90, Jul. 6, 2017.
Yan, et al., "Non-equivalence of Wnt and R-spondin ligands during Lgr5+ intestinal stem cell self-renewal", Nature, vol. 545, No. 7653, pp. 238-242, May 11, 2017.
Zhang, et al., "Massively Parallel Single-Molecule and Single-Cell Emulsion Reverse Transcription Polymerase Chain Reaction Using Agarose Droplet Microfluidics", Anal. Chem., vol. 84, No. 8, pp. 3599-3606, Published: Mar. 27, 2012.
Zheng, et al., "Massively parallel digital transcriptional profiling of single cells", Nature Communications, vol. 8, Article No. 14049, pp. 1-12, Published: Jan. 16, 2017.
Metzker, "Sequencing technologies—the next generation", Nature Reviews, Genetics, vol. 11, pp. 31-46, Published online: Dec. 8, 2009.
Sheng et al., "Different Strategies of Covalent Attachment of Oligonucleotide Probe onto Glass Beads and the Hybridization Properties", Applied Biochemistry and Biotechnology, 2008, pp. 54-65, vol. 152, No. 1.
Xu et al., "Microengineering Methods for Cell-based Microarrays and High-Throughput Drug-Screening Applications", Biofabrication, 2011, pp. 1-14, vol. 3, No. 3.
Yamamoto, "In situ Modification of Cell-Culture Scaffolds by Photocatalytic Decomposition of Organosilane Monolayers", Biofabrication, 2014, pp. 1-9, vol. 6, No. 3.
"2017 Top 10 Innovations", 2017 Top 10 Innovations, The Scientist, pp. 1-11, Dec. 1, 2017.
"Acrylamide Product Information Sheet", Sigma Aldrich 1996 Product Information Sheet, A8887, pp. 1-2, 1996.
"American Cell Biology Meeting Program 2017", The 2017 ASCB EMBO Meeting, pp. 1-198, Dec. 2017.
"An Introduction to Linked-Read Technology for a More Comprehensive Genome and Exome Analysis", 10X Genomics Technical Note, pp. 1-5, 2016.
Bio-Rad and Illumina to Co-Develop Comprehensive Solution for Single-Cell Genomics, "Scalable, High-Throughput Platform to Offer Unprecedented Insight into Gene Expression of Individual Cells," Bio-Rad Newsroom, pp. 1-2, Jan. 11, 2016.
"Bio-Rad ddSEQ Single-Cell Isolator Instruction Manual", Bio-Rad, Catalog #12004336, pp. 1-24, 2017.
"Bio-Rad Laboratories, Inc. Form 10-K for the year ended Dec. 31, 2016", pp. 1-92.
"Bio-Rad Life Science Research Product Catalog", Bio-Rad Life Science Research 2017 Product Catalog, pp. 1-500, 2017.

(56) References Cited

OTHER PUBLICATIONS

"Boston Medical Center/ Boston University School of Medicine Department of Medicine Newsletter", pp. 1-20, 2017.
"Cancer Moonshot", National Cancer Institute, pp. 1-4, Jan. 8, 2019.
"ChromiumTM Genome Reagent Kits v2 User Guide," Multiplex Kit, 96 rxns, PN-120262, 10X Genomics, pp. 1-71, 2016.
"ChromiumTM Single Cell 3' Reagent Kits Quick Reference Cards", ChromiumTM Single Cell 3' Chip Kit PN-120232, 10X Genomics, pp. 1-10, 2016.
"ChromiumTM Chromium Single Cell 3' Reagent Kits Safety Data Sheets", ChromiumTM Single Cell 3' Gel Bead Kit PN-120231, 10X Genomics, pp. 1-10, Jul. 11, 2016.
"ChromiumTM Chromium Single Cell 3' Reagent Kits v2 Safety Data Sheets," Chromium Single Cell 3' Gel Bead Kit v2, 16 runs, PN-120235, 10X Genomics, pp. 1-10, Oct. 7, 2016.
"Chromium Single Cell 3' Reagent Kits v3 with Feature Barcoding technology for CRISPR Screening", Chromium Single Cell 3' GEM, Library & Gel Bead Kit v3, 4 rxns PN-1000092, 10X Genomics, pp. 1-70, CG000184 | Rev A, 2018.
"ChromiumTM Single Cell 3' Reagent Kits v2 Quick Reference Cards," ChromiumTM Single Cell 3' Library & Gel Bead Kit, 4 rxns PN-120267, 10X Genomics, CG000075 | Rev C, pp. 1-10, 2017.
"ChromiumTM Single Cell 3' Reagent Kits Safety Data Sheets," ChromiumTM Single Cell 3' Library Kit, 10X Genomics, PN-120230, pp. 1-139, May 25, 2016.
"ChromiumTM Single Cell 3' Reagent Kits v2 Safety Data Sheets," ChromiumTM Single Cell 3' Library Kit v2 16 rxns, PN-120234, 10X Genomics, pp. 1-121, Oct. 7, 2016.
"Chromium Single Cell 3' Reagent Kits v2 User Guide," Chromium Single Cell 3' Library & Gel Bead Kit v2, 16 rxns PN-120237, 10X Genomics, pp. 1-74, 2018.
"ChromiumTM Single Cell V(D)J Reagent Kits User Guide," ChromiumTM Single Cell 5' Library & Gel Bead Kit, 16 rxns PN-1000006, 10X Genomics, pp. 1-73, 2017.
"Chromium Single Cell 3' Reagent Kits v2 User Guide", Chromium Single Cell A Chip Kit, 16 rxns PN-1000009, 10X Genomics, pp. 1-74, CG00052 | Rev E, 2018.
"Chromium Single Cell 3' Reagent Kits v2 Safety Data Sheets," Chromium Single Cell A Chip Kit, 48 runs, 10X Genomics, PN-120236, Oct. 6, 2016.
"Chromium Single Cell ATAC Reagent Kits," Chromium Single Cell ATAC Library & Gel Bead Kit, 16 rxns PN-1000110, 10X Genomics, CG000168 | Rev A, pp. 1-47, 2018.
"Chromium Single Cell DNA Reagent Kits", Chromium Single Cell DNA Library & Gel Bead Kit, 16 rxns PN-1000040, 10X Genomics, CG000153 | Rev B, pp. 1-65, 2018.
"ChromiumTM Controller Training Kit User Guide", 10X Genomics, CG00021 | Rev B, pp. 1-27, (Product ID 120244), 2016.
"ChromiumTM Training Kits Safety Data Sheets", ChromiumTM Training Reagents and Gel Bead Kit, 10X Genomics, PN-120238, Rev A, pp. 1-33, May 24, 2016.
"ddSEQ™ Cartridge Holder", Bio-Rad ddSEQ™ Cartridge Holder #12004739, 2016.
"ddSEQ™ Single-Cell Isolator—Accessories", ddSEQ™ Single-Cell Isolator—Accessories—Bio-Rad, pp. 1-2, 2016.
"ddSEQ™ Single-Cell Isolator—Ordering", ddSEQ™ Single-Cell Isolator Bio-Rad, 2016.
"ddSEQ™ Single-Cell Isolator by Bio-Rad", Bio-Rad, pp. 1-8, Select Science, 2019.
"ddSEQ™ Single-Cell Isolator by Bio-Rad", ddSEQ™ Single-Cell Isolator, Bio-Rad, pp. 1-2, 2016.
"ddSEQ™ Test Cartridges", Bio-Rad ddSEQ™ Test Cartridges #12003862, 2016.
"Deoxyribonuclease | from bovine pancreas", Sigma-Aldrich Deoxyribonuclease I from bovine pancreas, CAS No. 9003-98-9, 2018.

"DNase I (RNase-free)", New England Biolabs, Inc. (NEB), pp. 1-6, 2018.
"DTT 1,4-Dithiothreitol", Sigma-Aldrich, CAS No. 3483-12-3, pp. 1-4, 2015.
Office Action issued by the European Patent Office in Application No. 15767655.2 on Apr. 17, 2018, 4 pages.
Office Action issued by the European Patent Office in Application No. 15767655.2 on Jul. 11, 2018, 12 pages.
Banga, J.P., "SDS-Polyacrylamide Gel Electrophoresis (SDS-PAGE)", Encyclopedia of Immunology ISBN:0-12-226765-6, pp. 2143-2144, 1998.
"Generation of Human Tumor Atlases-Cancer Moonshot Recommendation", National Cancer Institute, pp. 1-4, Jan. 8, 2019.
"Genome Analysis Core", pp. 1-2, Georgia Institute of Technology, 2019.
"Georgia Tech—Shared User Management System", pp. 1-12, Georgia Institute of Technology, 2015.
"Hydrophobic Interaction Chromatography", Amersham Pharmacia Biotech 2000, Edition AB, pp. 1-104, ISBN 91-970490-4-2, 2000.
"Illumina and Bio-Rad Launch Solution for Single-Cell Genomic Sequencing to Enable Robust Study of Complex Diseases", Bio-Rad, pp. 1-2, Jan. 9, 2017.
"Illumina and Bio-Rad Launch Solution for Single-Cell Genomic Sequencing to Enable Robust Study of Complex Diseases", 69th AACC Annual Scientific Meeting Press Program, Article ID: 678428, pp. 1-6, Jul. 25, 2017.
"Illumina Bio-Rad SureCell WTA 3' Library Prep Reference Guide", Illumina, Document # 1000000021452 v01, pp. 1-53, Jun. 2017.
"Illumina SureCell WTA 3' Checklist", Illumina, Document # 1000000021454 v00, pp. 1-6, Feb. 2017.
"Illumina® | Bio-Rad® Single Cell Sequencing", illumina | Bio-Rad, pp. 1-37, 2015.
"Illumina® Bio-Rad® SureCellTM WTA 3' Library Prep Kit for the ddSEQTM System", illumina | Bio-Rad, pp. 1-4, 2015.
"Infoporte—Cores", Infoporte | Version: 7.1.1 | © 2019 The University of North Carolina at Chapel Hill.
"The Instrument—Chromium Controller Compatible Solutions", 10X Genomics, pp. 1-7, 2019.
Massachusetts Institute of Technology, "Communication Pursuant to Rule 164(2)(b) and Article 94(3) EPC for EP 17705198.4", Oct. 11, 2019, 9 pages.
Dekosky, et al., "High-Throughput Sequencing of the Paired Human Immunoglobulin Heavy and Light Chain Repertoire", Nature Biology, vol. 31, No. 2, Feb. 2013, pp. 166-169.
The Broad Institute, Inc., "International Preliminary Report on Patentability issued in International Application No. PCT/US2017/013791", mailed on Feb. 12, 2018, 7 pages.
The Broad Institute, Inc., "International Search Report and Written Opinion issued in International Application No. PCT/US2017/013791", mailed on Jul. 12, 2017, 15 pages.
Dekoskey, et al., "High-throughput sequencing of the paired human immunoglobulin heavy and light chain repertoire", Nature Biotechnology, 31(2), Feb. 2013, pp. 166-169.
Ilicic, et al., "Classification of Low Quality Cells from Single-Cell RNA-Seq Data", Genome Biology, vol. 17, No. 1, Feb. 17, 2016, 15 pages.
Macosko, et al., "Highly Parallel Genome-wide Expression Profiling of Individual Cells Using Nanoliter Droplets" Cell, 161, May 21, 2015, pp. 1202-1214.
Ogunniyi, et al., "Profiling Human Antibody Responses by Integrated Single-Cell Analysis", Vaccine, vol. 32, No. 24, May 19, 2014, 17 pages.
Steinberg, et al., "Strategies for Covalent Attachment of DNA to Beads", Biopolymers, vol. 73, No. 5, Feb. 17, 2004, pp. 597-605.
Yao, et al., "Functional Analysis of Single Cells Identifies a Rare Subset of Circulating Tumor Cells with Malignant Traits", Integrative Biology, vol. 6, No. 4, Apr. 2014, 20 pages.

* cited by examiner

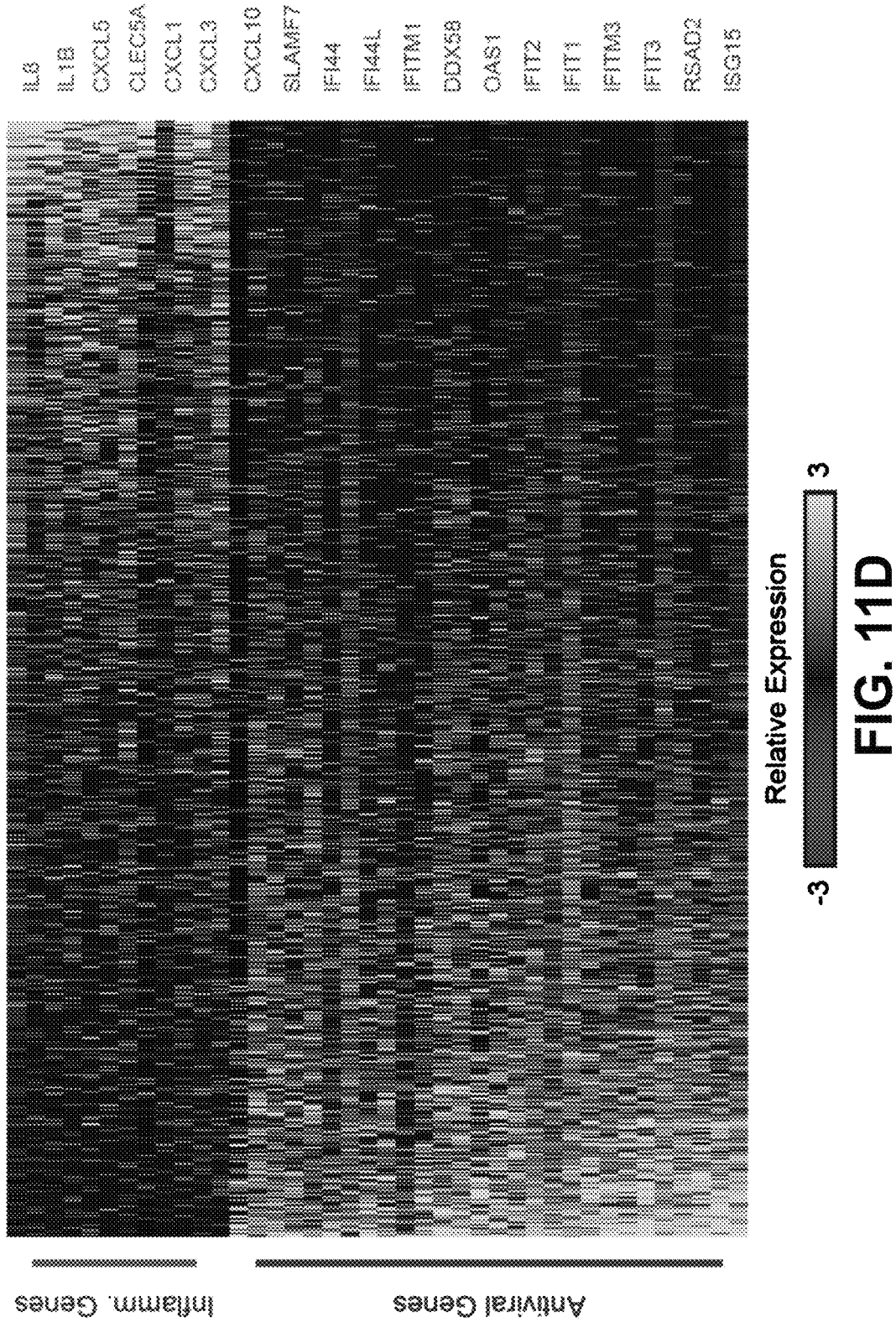

a
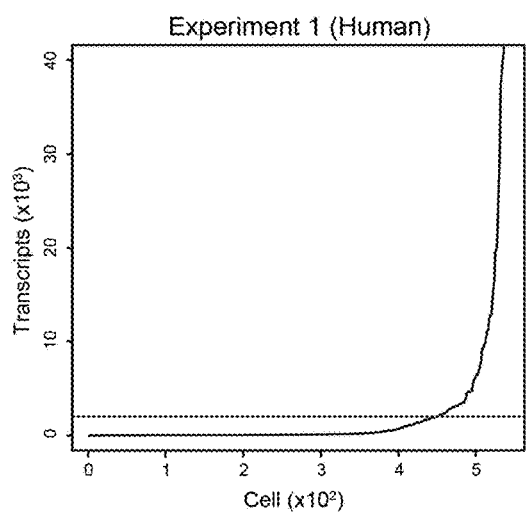 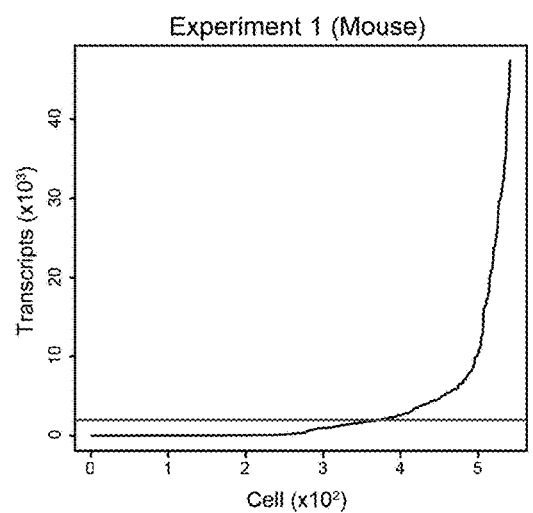
b
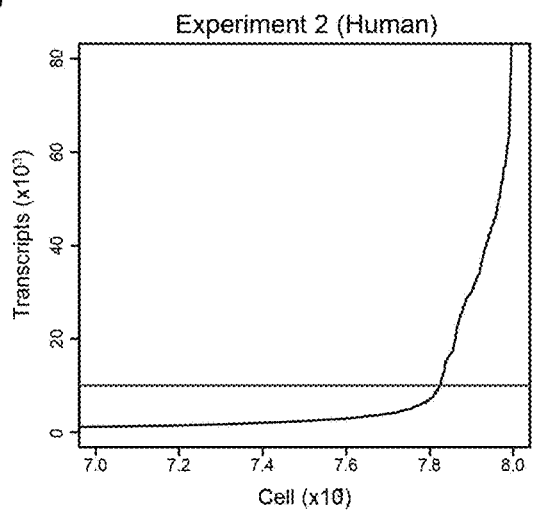 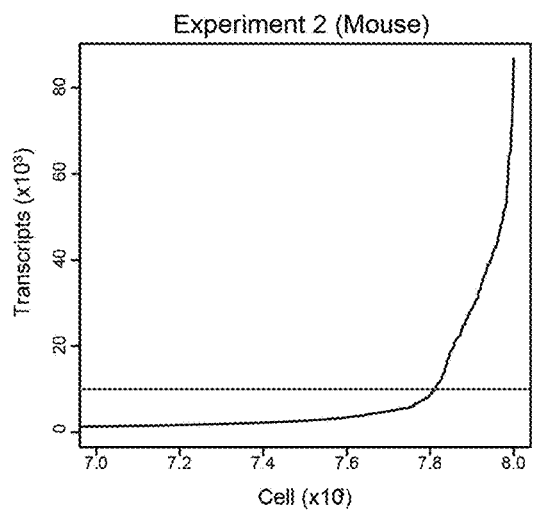
Figs. 20A-20B

SEMI-PERMEABLE ARRAYS FOR ANALYZING BIOLOGICAL SYSTEMS AND METHODS OF USING SAME

RELATED APPLICATIONS AND INCORPORATION BY REFERENCE

This application claims benefit of and priority to U.S. Provisional 62/279,500, filed on Jan. 15, 2016.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under grant numbers AI104274 and AI106025 awarded by the National Institutes of Health, and under Contract No. W911NF-13-D-0001 awarded by the U.S. Army Research Office. The government has certain rights in the invention.

FIELD OF THE INVENTION

The present application provides a method of assembling a container for one or multiple parallel steps of biochemical analysis on one or more cells comprising performing molecular bonding of a porous membrane on an apical surface of an array having a plurality of wells, wherein the molecular bonding substantially isolates each well from adjacent wells.

BACKGROUND OF THE INVENTION

The well-based biological analysis platform, also referred to as Seq-well, facilitates the creation of barcoded single-cell sequencing libraries from thousands of single cells using a device that contains 86,000 40-micron wells. In some embodiments, the device contains wells comprising 45 µm×45 µm×60 µm. Importantly, single beads can be loaded into each microwell with a low frequency of duplicates due to size exclusion (average bead diameter 35 µm). By using a microwell array, loading efficiency is greatly increased compared to drop-seq, which requires poisson loading of beads to avoid duplication at the expense of increased cell input requirements. Seq-well, however, is capable of capturing nearly 100% of cells applied to the surface of the device.

Due to its low input requirements and efficient capture of beads and cells, the Seq-well platform has broad application in numerous research and clinical settings. For example, the device provides Biologic Safety Level 3 (BL3) facilities to study the dynamics of tuberculosis infection or in the field.

While the platform has been optimized for the generation of individually barcoded single-cell sequencing libraries following confinement of cells and mRNA capture beads (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214), it is capable of multiple levels of data acquisition. The platform is compatible with other assays and measurements performed with the same array. Levels of cell surface proteins (Ogunniyi, A. O., B. A. Thomas, T. J. Politano, N. Varadarajan, E. Landais, P. Poignard, B. D. Walker, D. S. Kwon, and J. C. Love, "Profiling Human Antibody Responses by Integrated Single-Cell Analysis" Vaccine, 32(24), 2866-2873), secreted proteins (see, e.g., U.S. Pat. Nos. 7,776,553; 8,835,187; 8,772,049; 8,865,479; JP 571822; EP 2 297 333; U.S. application Ser. No. 13/132,858), cytolytic behaviors of cells (see, e.g., U.S. application Ser. No. 13/145,300), dynamic motility (see, e.g., Yao, X. et al. "Functional analysis of single cells identifies a rare subset of circulating tumor cells with malignant traits." Integr Biol (Camb), doi:10.1039/c3ib40264a (2014), and gene expression (see, e.g., U.S. application Ser. No. 12/911,642) can be assessed using microwell technology. By coupling array position through an oligo microarray or another method that enables spatial encoding of position (e.g., tagging via optical activation, contact printing, microarraying, jet printing, or the like), it will be possible to link multiple levels of biological information to single-cell sequencing data, or other genomic data or other downstream measurements, obtained from the Seq-well platform.

Unlike other microwell technology platforms (Cyto-Seq: Cellular Research/BD), membrane sealing enables efficient exchange of buffers, allowing for more efficient capture of biological molecules of interest and limits cross-contamination of molecules from adjacent wells by spatial diffusion. Moreover, the microwell technology platform enables easy addition and removal of materials from the container or well, a need currently not met by other modalities. Addition of materials allows for the introduction of necessary reagents, such as lysis buffers and affinity probes; removal or subtraction of materials allows for purification and other processes not previously well-suited on a massively parallel platform.

Citation or identification of any document in this application is not an admission that such document is available as prior art to the present invention.

SUMMARY OF THE INVENTION

The present application provides a high-throughput parallel single cell biochemical analysis in an array of wells or containers comprising or characterized by providing a first functionalized surface of each well or container, wherein the functionalized surface comprises an affinity resin; and providing a second functionalized surface of an array material to a top surface, wherein the functionalized surface provides accessible ionic functional groups. In an aspect of the method, the method further comprises at least one or more additional functionalized surface of each well or container, wherein the additional functionalized surfaces provides for multiplexing reactions. In a further aspect, the array material comprises polydimethylsiloxane, polycarbonate, polystyrene, polymethyl-methacrylate, polyvinylidene difluoride, polyvinylchloride, polypropylene, cyclic olefin co-polymer, a glass, or silicon. In another aspect of the method, the array material is doped with an ionic functional group anywhere from 1% to 30% (by molar basis). In an embodiment of the method, the array material is doped with a functional group which can undergo further molecular bonding or modification via covalent bonding anywhere from 1% to 30% (by molar basis). In an embodiment, the ionic functional group is a negatively charged functional group. In a further embodiment, the negatively charged functional group is a carboxylic acid. In an aspect of the method, the top surface comprises an array functionalized to an organosilane. In a further aspect, the organosilane functionalized array surface provides free alcohols upon treatment. In an embodiment, the treatment comprises air plasma under mild vacuum. In an embodiment, the free alcohols are reacted with an aminosilane providing an amine. In a further embodiment, the amine is activated with an isothiocyanate. In an embodiment, the isothiocynate is conjugated to a polysaccharide. In an embodiment, the ionic functional group is a positively charged functional group. In a further embodiment, the positively charged functional group is an amine. In an embodiment, the amine is a polyamine. In an aspect of the method, the amine is selected from a group consisting of chitosan, poly(lysine), polyglucosamine and poly(acetyl) glucosamine. In another aspect of the method, the affinity resin comprises a negatively charged surface, wherein the negatively charged surface repels mRNA, and wherein the negatively charged surface enables mRNA to be captured by poly(dT) beads. In an aspect, the affinity resin comprises a carboxylate. In a further aspect, the carboxylate is poly (glutamate) glutamate or aspartate. In an embodiment, the wells or containers comprise micro-sized wells, nano-sized wells, or pico-sized wells. In an embodiment, the wells or containers comprise 250 μm, 100 μm, 50 μm, 30 μm, 15 μm, 5 μm, or 1 μm wells. In an aspect of the method, the wells or containers are sealed with a membrane. In an embodiment, the membrane. In an embodiment, the membrane is an ultrafiltration membrane. In an embodiment, the membrane comprises a weak cationic exchange surface. In an embodiment, the ultrafiltration membrane comprises a polymeric surface functionalized with chitosan.

The present application provides a microwell comprising or characterized by a first functionalized surface of each well or container, wherein the functionalized surface comprises an affinity resin; and a second functionalized surface, wherein the functionalized surface provides accessible ionic functional groups. In an embodiment of the microwell, the second functionalized surface is configured for attachment of an ion exchange membrane. In an embodiment of the microwell, the top surface comprises an array functionalized to an organosilane. In a further embodiment, the organosilane functionalized array surface provides free alcohols upon treatment. In another embodiment, the treatment comprises air plasma under mild vacuum. In an embodiment, the free alcohols are reacted with an amino-silane providing an amine. In another embodiment, the amine is activated with an isothiocyanate. In an embodiment, the isothiocynate is conjugated to a polysaccharide. In another embodiment, the ionic functional group is a positively charged functional group. In an embodiment, the positively charged functional group is an amine. In a further embodiment, the negatively charged functional group is a polyamine. In an embodiment, the amine is selected from a group consisting of chitosan, poly(lysine), polyglucosamine and poly(acetyl)glucosamine. In another embodiment, the affinity resin comprises a negatively charged surface, wherein the negatively charged surface repels mRNA, and wherein the negatively charged surface enables mRNA to be captured by poly(dT) beads. In an embodiment of the microwell, the affinity resin comprises a carboxylate. In a further aspect, the carboxylate is poly(glutamate)glutamate or aspartate. In an embodiment, the wells or containers comprise micro-sized wells, nano-sized wells, or pico-sized wells. In an embodiment, the wells or containers comprise 250 μm, 100 μm, 50 μm, 30 μm, 15 μm, 5 μm, or 1 μm wells. In embodiments of the invention, the wells are from 250 μm to 100 μm, or from 100 μm to 50 μm, or from 50 μm to 30 μm, or from 30 μm to 15 μm, of from 15 μm to 5 μm, or from 5 μm to 1 μm. In an embodiment, the first functionalized surface comprises a nucleic acid. In an embodiment, the first functionalized surface comprises an antigen binding protein. In an embodiment, the microwell is configured to contain a barcoded bead. The present application also provides an array comprising two or more microwells of the aforementioned microwells.

In a related aspect, the present application provides method for high-throughput parallel single cell biochemical analysis in an array of wells or containers comprising or characterized by (a) a first functionalized surface of an open well or container, wherein the functionalized surface comprises an affinity resin or antigen binding protein; (b) loading each functionalized surface well or container with anywhere from 1 to 5 cells; (c) further loading each functionalized surface well or container with a barcoded poly (dT) bead, wherein the barcoded bead; (d) sealing the first functionalized surface well or container with a second functionalized surface; wherein the second functionalized surface is an ultrafiltration membrane; wherein the second functionalized surface is transfixed to the edges of the well or container providing a closed vessel; wherein the functionalized surface provides accessible ionic functional groups; (e) performing successive buffer exchanges to lyse the cells in solution, wherein the lyse cells provide protein and nucleic acids; and, (f) removing the ultrafiltration membrane. In another aspect, the present application provides a method for high-throughput parallel single cell biochemical analysis in an array of wells or containers comprising: (a) delivering a first reagent to a container comprising a functionalized inner surface; (b) attaching a membrane to a functionalized top surface; and (c) delivering a second reagent to the container by transfer through the membrane. In an embodiment, the method further comprises analyzing the barcoded beads, protein, and nucleic acids. In an embodiment, the method further comprises analyzing the reaction products.

The present application provides a research method comprising or characterized by obtaining the reaction product of any one of the foregoing methods and transmitting over a network or connection for receipt by an electronic data system data relating to the obtained reaction product. In a related aspect, the research method further comprises receiving by an electronic system the data relating to the obtained reaction product.

The present application provides an improved high-throughput parallel single cell biochemical analysis in an array of wells or containers comprising or characterized by providing a first functionalized surface of each well or container, wherein the functionalized surface comprises an affinity resin; and providing a second functionalized surface of an array material to a top surface, wherein the functionalized surface provides accessible ionic functional groups.

The present application provides an improved research method comprising or characterized by obtaining the reaction product of any one of the foregoing methods and transmitting over a network or connection for receipt by an electronic data system data relating to the obtained reaction product. In a related aspect, the research method further comprises receiving by an electronic system the data relating to the obtained reaction product.

The present application provides wells or containers wherein the wells or containers are open vessels. In a related aspect, the open vessels can be configured to affix a membrane or additional surface to provide a closed vessel. The wells or containers may be any number of shapes such as conical, flat-bottomed, hemispherical-bottomed. The wells or containers comprise volume to accommodate several types of starting material, including, but not limited to a barcoded bead, solution, and approximately 1 to 5 cells. Well dimensions are designed to accommodate only one bead enabling single-bead loading efficiencies of ~95%. Well dimensions may range anywhere from 15 microns to 250 microns. In an embodiment, the dimensions may range anywhere from 50 microns to 90 microns. In an embodiment, the dimensions may range anywhere from 75 microns to 100 microns. In an embodiment, the dimensions may range anywhere from 40 microns to 75 microns.

The present application provides a method of assembling a container for biochemical analysis, multiple steps of biochemical analysis, or multiple parallel steps of biochemical analysis on one or more cells comprising performing molecular bonding of a porous membrane on an apical or basal surface of an array having a plurality of wells, wherein the molecular bonding substantially isolates each well from adjacent wells. In an embodiment, the molecular bonding of the method of assembling a container for one or multiple parallel steps of biochemical analysis comprises one or more of covalent bonding, ion-ion bonding, dipole-dipole interaction, dipole-dipole interaction, ion-dipole interaction, hydrogen bonding, van der Waals forces. In an aspect of the method, the bonding is effective when the container is immersed in an aqueous solution. In a further aspect of the method, the plurality of wells comprises about at least 1,000 or at least 10,000 or at least 100,000 or at least 1,000,000. In an embodiment of the invention, the wells are micro-sized wells, nano-sized wells, or pico-sized wells (e.g., microliter, nanoliter, picoliter). In a further embodiment, the well volume is equal or less than a microliter, preferably equal or less than a nanoliter. In another embodiment, the isolation includes confining cells (eukaryotic or prokaryotic) or cellular components inside the wells, while allowing flow of liquid through the porous membrane. In an embodiment, the isolation includes confining macromolecules inside the wells, while allowing flow of liquid through the porous membrane. In another embodiment, the isolation includes confining macromolecules inside the wells, while allowing flow of small molecules through the porous membrane. In an even further embodiment of the method, the isolation includes confining RNA, DNA, proteins, or combination thereof inside the wells, while allowing flow of liquid through the porous membrane. In another embodiment of the method, the isolation includes confining RNA, DNA, proteins, or combinations thereof inside the wells, while allowing flow of small molecules through the porous membrane. In an embodiment, the isolation includes confining molecules having a size of 1, kDa, 10 kDa, 50 kDa, 100 kDa; 1,000 kDa, 10,000 kDa, 100,000 kDa, or of 1,000,000 kDa.

In a related aspect, the method of assembling a container for biochemical analysis, multiple steps of biochemical analysis, or multiple parallel steps of biochemical analysis on one or more cells, wherein the bonding between the porous membrane and the top surface of the array is reversible. In an embodiment of invention, the method of bonding comprises providing an array, wherein the exposed surface of the array bears charge of a first polarity; providing a porous membrane, wherein the porous membrane bears a charge of a second polarity, the second polarity being opposite the first polarity; hydrating the charged porous membrane; and positioning the charged porous membrane onto the charged top surface of the array. In a further embodiment, the method comprises a first and second polarity, wherein the first polarity is positive and the second polarity is negative. In an embodiment, the array top surface comprises organosiloxane functional groups conjugated to PDMS. In another embodiment, the array is a polymer poly-dimethylsiloxane (PDMS), polycarbonate (PC), polystyrene (PS), polymethyl-methacrylate (PMMA), PVDF, polyvinylchloride (PVC), polypropylene (PP), cyclic olefin co-polymer (COC), a glass, or is silicon. In an embodiment, the method comprises a top surface wherein the top surface comprises functional groups conjugated to cyclic olefin co-polymer using aryl diazonium salts. In a further embodiment, the functionalization of the top surface is achieved through UV-mediated graft polymerization. In an embodiment, the method comprises differential functionalization wherein the differential functionalization of well and surface for membrane attachment using UV-mediated graft polymerization. In another embodiment, the adsorption of biomolecules is reduced through UV mediated graft. In an even further embodiment, the polypropylene devices are modified with chitosan following oxygen plasma treatment.

In an aspect of the invention, the method comprises PMMA devices, wherein the devices are modified with chitosan following oxygen plasma treatment. In a related aspect, the method comprises polystyrene devices, wherein the polystyrene devices are modified with dextran. In an embodiment, the invention comprises PDMS devices, wherein the PDMS devices are modified with biological antifouling reagents.

In a related aspect of the invention, the method comprises a charge wherein the charge is induced on the top or bottom surface of the array by plasma treating the array; coating the exposed surface with an organosiloxane functional group and optionally treating the exposed surface of the array with a polysaccharide. In an embodiment, the polysaccharides is chitosan, chitin, or cellulose. In another embodiment, the method comprises covalent linking of the membrane. In an even further embodiment, the porous membrane has been functionalized. In an embodiment, the porous membrane has been functionalized by a reactive functional group. In an embodiment, the method comprises a porous membrane which has been functionalized with an amine, an aminosilane, a thiosilane, a methacrylate silane, or a poly(allylamine), and optionally in addition with one or more of maleimide, 2-iminothiolane (Traut's reagent), polyacrylic acid, bisepoxy-PEG.

In an aspect of the invention, the method comprises a functionalized surface, wherein the functionalization includes treating with an air or oxygen plasma, optionally followed by vapor or solution phase deposition of an amine silane or a thiosilane. In an embodiment, the method comprises treating the porous membrane with a reactive biotin, such as a biotin functionalized with a reactive group, such as a biotin linked to a leaving group, such as NHS-biotin. In an embodiment, the method further comprises treating the membrane with NHS-maleimide. In an embodiment, the method comprises an exposed surface of the array, wherein the exposed surface has been functionalized. In an embodiment, the method comprises an exposed surface, wherein the exposed surface of the array has been functionalized by a reactive functional group. In an embodiment, the method comprises an exposed surface, wherein the exposed surface of the array has been functionalized with an amine, an amine silane, a thiosilane, a methacrylate silane, a poly(allylamine), poly(lysine), BSA, epoxide silane, chitosan and optionally in addition with one or more of 2-iminothiolane (Traut's reagent), polyacrylic acid, epoxide-PEG, oxidized agarose.

In an aspect of the invention, the method comprises functionalization of an exposed surface, wherein the functionalization includes treating with an air or oxygen plasma followed by submersion in an aqueous solution followed by submersion in aqueous solution followed by baking. In another embodiment, the aqueous solution includes a polyamine such as polyethylenimine (PEI) or poly(lysine). In a further embodiment, the baking is performed at 80° C. In a related embodiment, the functionalization includes treating with an air or oxygen plasma followed by vapor deposition of an amine silane. In an embodiment, the functionalization results in a complementary crosslinking group on the exposed surface of the array. In an embodiment, the method comprises part or all of an inside surface wherein the part or all of the inside surface of the wells of the array is functionalized with a different molecule than the exposed surface of the array. In another embodiment, the method comprises part or all of an inside surface wherein the part or all of the inside surface of the wells of the array is functionalized to activate loaded cells. In a further embodiment, the method comprises part or all of an inside surface wherein the part or all of the inside surface of the wells of the array is functionalized to capture secreted products, such as proteins. In a further embodiment, the method comprises part or all of an inside surface wherein the part or all of the inside surface of the wells of the array is functionalized to make the wells hospitable to a living cell, for example with a hydrophilic coating, such as an alcohol, amine or a carboxylic acid functionality or any combination thereof. In an even further embodiment, the method comprises submerging the array in an aqueous solution. In an embodiment, the aqueous solution contains a functional group which will react with an amine to place a complementary crosslinking moiety on the exposed surface of the array. In another embodiment, the aqueous solution contains a functional group which will react with an amine to place a complementary crosslinking moiety on the porous membrane.

In another aspect of the invention, the method comprises an aqueous solution and a molecule, wherein the aqueous solution and molecule comprises streptavidin in a carbonate buffer, or any aqueous buffer solution which facilitates peptide bond formation. In an embodiment, the aqueous solution and molecule comprises 2-iminothiolane and streptavidin. In a further embodiment, the method comprises washing the array and heating the array. In an embodiment, the heating is performed in an aqueous buffer to a temperature of approximately 50° C. for approximately 10 minutes. In an embodiment, the method comprises moving the array to a buffer including a molecule for inclusion on the inside surface of the well. In an embodiment, the method comprises loading cells into the wells of the array prior to bonding the porous membrane on the exposed surface of the array. In an embodiment, the method comprises clamping the porous membrane to the array. In a further embodiment, the method comprises placing a glass slide on the exposed side or surface of the porous membrane and applying a clamp to the assembly comprised of the glass slide, the porous membrane and the array for a predetermined cure period, and removing the clamp after the predetermined cure period.

The present application provides a method for massively parallel single cell biochemical analysis, comprising providing a porous membrane, providing an array of wells, loading the wells of the array with cells, for example by pouring or pipetting a cell suspension onto the exposed surface of the array; and, assembling the porous membrane on the array by molecular bonding. In an embodiment, the method provides biochemical analysis, wherein the biochemical analysis comprises cell lysis performed in the well, and subsequently one or more of RT-PCR, RNA-seq, PCR, qPCR, DNA-seq, mass spectroscopy, ATAC-seq, bisulfite sequencing, immuno-PCR, in-situ sequencing, rolling circle amplification, in-situ hybridization, proximity extension assays, immunofluorescence, ELISA, reverse ELISA, multiple displacement reaction, DNase hypersensitivity, chip-seq, or any other genomic assay.

In an aspect of the invention provides a method wherein the porosity of the porous membrane is selected from porosities suitable for one or more of the following applications: protein capture after cell lysis, RNA capture after cell lysis, transcript capture after cell lysis, mammalian cell culture, protein capture trough micro-engraving, antibody staining for cytometry, bacterial cell culture.

In another aspect, the invention provides a kit for massively parallel single cell biochemical analysis, comprising: one or more porous membrane(s), one or more arrays of wells, optionally, a set of micro-beads, wherein each microbead bears a unique molecular identifier (UMI), optionally, a set of instructions for assembling the porous membrane on the array by bonding. In an embodiment, the invention provides a kit wherein the method of bonding comprises: providing an array, wherein the exposed surface of the array bears charge of a first polarity; providing a porous membrane, wherein the porous membrane bears a charge of a second polarity, the second polarity being opposite the first polarity; hydrating the charged porous membrane; and positioning the charged porous membrane onto the charged exposed surface of the array.

The present application also provides a container for multiple parallel single-cell biochemical analysis, comprising an array having a plurality of wells, wherein said array has an exposed surface in a planar configuration with the openings of the wells, and a porous membrane configured to be positioned on the exposed surface of the array, wherein the porous membrane and the exposed surface of the array can cooperate by establishing molecular bonding so as to substantially isolate each well, or a subset of wells, from adjacent wells.

In another aspect, the invention provides a container for selective manipulation of cells, comprising: at least one compartments having an opening, and a reversibly-sealed, porous membrane removably positioned over the opening of the compartment, wherein the porous membrane substantially isolates the compartment from adjacent compartments.

The present application generally provides methods of diagnosis and treatment in a subject in need thereof. The present application provides a method of identifying cellular heterogeneity in a subject. In certain embodiments, the cellular heterogeneity is associated with or a characteristic of a disease or disorder, or a state of a multicellular organism. Diseases or disorders comprising or characterized by cellular heterogeneity include, without limitation, neoplastic diseases, benign tumors, malignant tumors, sarcomas, carcinomas, and lymphomas. In an embodiment of the invention, the cellular heterogeneity characterizes a lung disease. In an embodiment of the invention, the cellular heterogeneity characterizes an immune disease or immune system state.

In an embodiment, the method comprises sequencing a nucleic acid sample from cells or tissues of a subject for example, but not limited to bronchial alveolar lavages and lung biopsies of the subject, thereby providing single cell sequences; analyzing cellular microenvironments using categorical spatial information; and, optionally assembling single cell sequences into a visual representation, wherein the relationship between amplified shared spatial barcodes of single cell sequences is obtained by a computational method.

The present application provides a method of identifying differentiation of myoblasts in a subject undergoing IGF therapy comprising sequencing a nucleic acid sample from myoblasts of a patient, thereby providing single cell sequences; analyzing cellular microenvironments using categorical spatial information; and, optionally assembling single cell sequences into a visual representation, wherein the relationship between amplified shared spatial barcodes of single cell sequences is obtained by a computational method.

The present application provides a method of identifying transcriptional regulation in macrophages comprising sequencing a nucleic acid sample from macrophages of a subject infected with *M. tuberculosis*, thereby providing single cell sequences of an infected subject; sequencing a nucleic acid sample from macrophages of a healthy subject uninfected with *M. tuberculosis*, thereby providing single cell sequences of an uninfected subject; measuring the differential nucleic acid levels between an infected subject and an uninfected subject; analyzing cellular microenvironments using categorical spatial information; and, optionally assembling single cell sequences into a visual representation, wherein the relationship between amplified shared spatial barcodes of single cell sequences is obtained by a computational method.

The present application provides a method of identifying cellular heterogeneity in acute myeloid leukemia cells in a subject having leukemia comprising sequencing a nucleic acid sample from acute myeloid leukemia cells of a subject, thereby providing single cell sequences; analyzing cellular microenvironments using categorical spatial information; and optionally assembling single cell sequences into a visual representation, wherein the relationship between amplified shared spatial barcodes of single cell sequences is obtained by a computational method.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

FIGS. 20A-20B illustrate transcript cutoff for species-mixing validation. Two arrays (a & b) were sequenced to confirm single-cell resolution and minimal cross-contamination between mouse and human cells. Applicants called cells by plotting the cumulative distribution of transcripts and making a cutoff at the elbow in the curve. In the first experiment (A), which was used to validate the single-cell resolution, Applicants shallowly sequenced the array and made the cutoff at 2,000 transcripts. In the second experiment (B), where Applicants sequenced the array deeply to allow a competitive comparison to Drop-Seq, Applicants made the cutoff at 10,000 transcripts.

R=0.751±0.0726; 10 Cells: R=0.952±0.008; 100 Cells: R=0.980±0.0006; 1000 Cells: R=0.983±0.0001).

FIGS. 22A-22I illustrate mapping lineage defining transcripts to PBMC clusters. (A) Clusters identified through graph-based clustering correspond to major immune cell populations. (B, E) CD4 T cells are characterized by expression of CD3D and T-cell receptor expression without pronounced expression of cytotoxic genes NKG7 and PRF1. (C,F) CD8 T cells are defined by expression of NKG7 and PRF1. (D,G) Monocytes are defined by expression of cathepsin B (CTSB) and SOD2. (E) Natural killer cells are characterized by expression of cytotoxic genes in the absence of T cell receptor expression. (H) B cells are marked by elevated expression of MS4A1 (CD20) transcripts. (I) Dendritic cells are enriched for expression of BIRC3.

Figure 23A:
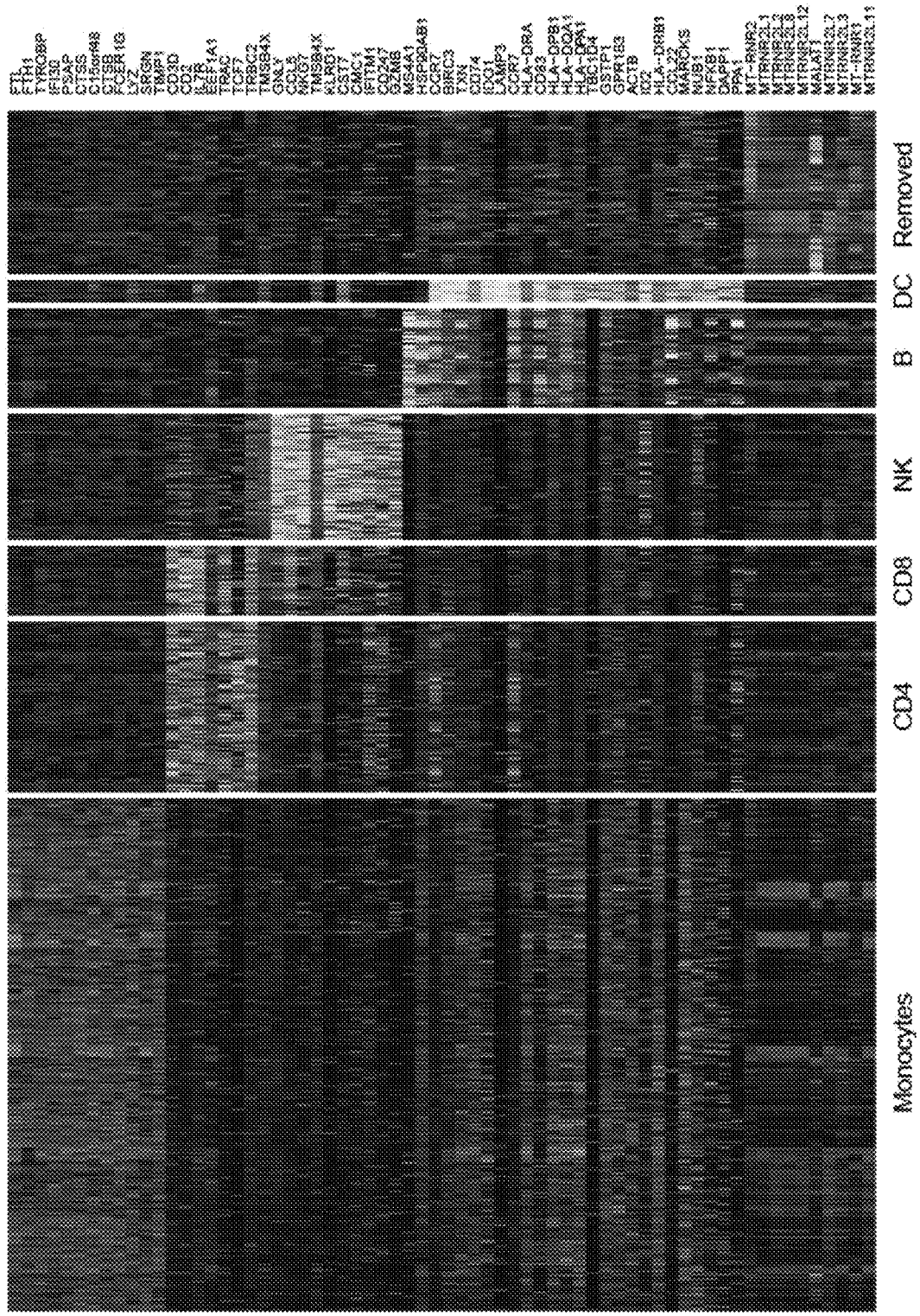
Figure 23B:
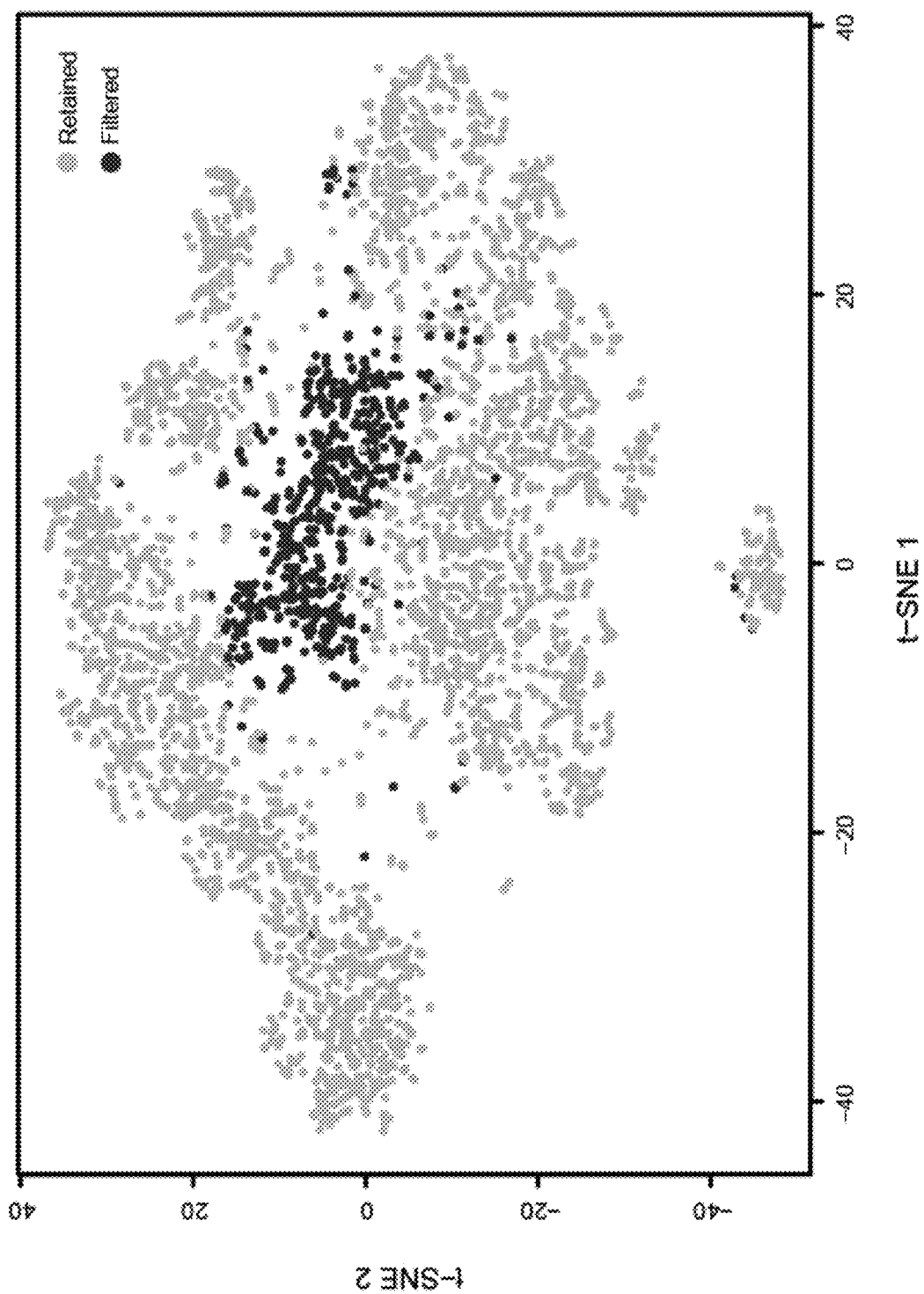

FIGS. 23A-23B illustrate a heatmap of PBMCs (A) Genes enriched in each cluster were identified using an "ROC" test in Seurat, comparing cells assigned to each cluster to all other cells. A heatmap was constructed using enriched genes found to define each cluster. One cluster of 602 cells that demonstrated exclusive enrichment of mitochondrial genes was removed as these likely represent low-quality or dying cells. (B) We generated a t-SNE projection of 4,296 cells with greater than 10,000 reads, 1,000 transcripts, 500 genes, and 65% transcript mapping. We removed a total of 602 cells from the final analysis found to be strongly enriched for expression of mitochondrial genes. The remaining 3,694 cells form distinct clusters enriched for lineage-defining that distinguish cells types from one another.

FIGS. 24A-24D illustrate read mapping quality in PBMCs. (A-C) Violin plots depicting reads (A), transcripts (B), and genes (C) per cell, separated by cell type. (D) Percent mRNA bases per cell, separated by cell type.

Figures 25A, 25B:
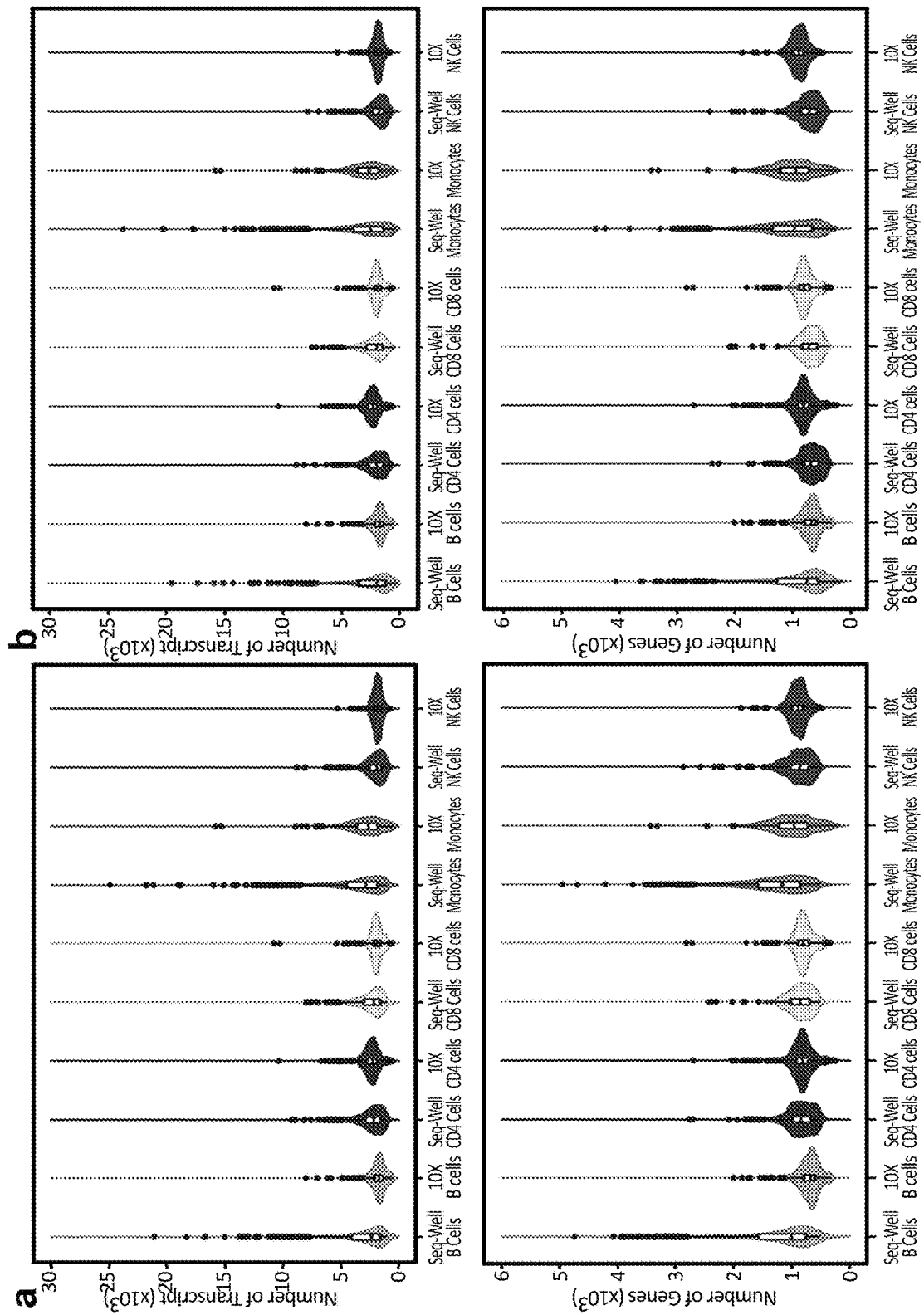

FIGS. 25A-25B illustrate a comparison of human PBMC gene and transcript capture with other massively-parallel scRNA-Seq methods. (a) Comparison of transcript capture (top) and gene detection (bottom) between Seq-Well and 10× Genomics within PBMC cell types prior to downsampling (colored as in FIG. 2; Center-line: Median; Limits: 1st and 3rd Quartile; Whiskers: +/−1.5 IQR; Points: Values >1.5 IQR). Among B cells (orange), an average of 1,315 genes and 3,632 transcripts were detected using Seq-Well and an average of 710 genes and 1,910 transcripts were detected in 10× Genomics data. Among CD4 T cells (blue), an average of 861 genes and 2,444 transcripts were detected using Seq-Well and an average of 815 genes and 2,370 transcripts were detected in 10× Genomics data. Among CD8 T cells (yellow), an average of 885 genes and 2,574 transcripts were detected using Seq-Well and an average of 809 genes and 2,029 transcripts were detected in 10× Genomics data. Among Monocytes (green), an average of 1,288 genes and 3,568 transcripts were detected using Seq-Well and an average of 974 genes and 2,835 transcripts were detected in 10× Genomics data. Among NK cells (red), an average of 902 genes and 2,338 transcripts were detected using Seq-Well and an average of 907 genes and 1,943 transcripts were detected in 10× Genomics data. (b) Transcript capture (top) and gene detection (bottom) upon downsampling of Seq-Well data to an average read depth 69,000 reads per cell (Center-line: Median; Limits: 1st and 3rd Quartile; Whiskers: +/−1.5 IQR; Points: Values >1.5 IQR). Upon downsampling, in Seq-Well, an average of 1,048 genes and 3103 transcripts were detected among B cells, 735 genes and 2,221 transcripts among CD4 T cells, 763 genes and 2,353 transcripts among CD8 T cells, 1,052 genes and 3,105 transcripts among monocytes, and 789 genes and 2,041 transcripts among NK cells.

FIGS. 26A-26D illustrate t-SNE visualization of exposed and unexposed macrophages using a 5,000 transcript cutoff. (A) Using a threshold of 5,000 detected transcripts identified 4,638 macrophages. (B) Among these 4,638 cells, 5 distinct clusters of macrophages were identified by performing graph-based clustering over 5 principal components (377 variable genes). (C) Clusters 1-3 are defined by unique gene expression signatures, while Clusters 4 and 5 are defined by expression of mitochondrial genes, suggesting low-quality cells (D) Following removal of cells within Clusters 4 and 5, there remain a total of 2,560 cells in Clusters 1-3.

FIGS. 27A-27D illustrate quality by cluster among tb macrophages. (A-C) Violin plots depicting reads (A), transcripts (B), and genes (C) per cell, separated by cluster. (D) Percent mRNA bases per cell, separated by cluster.

Figures 28A, 28B, 28C:
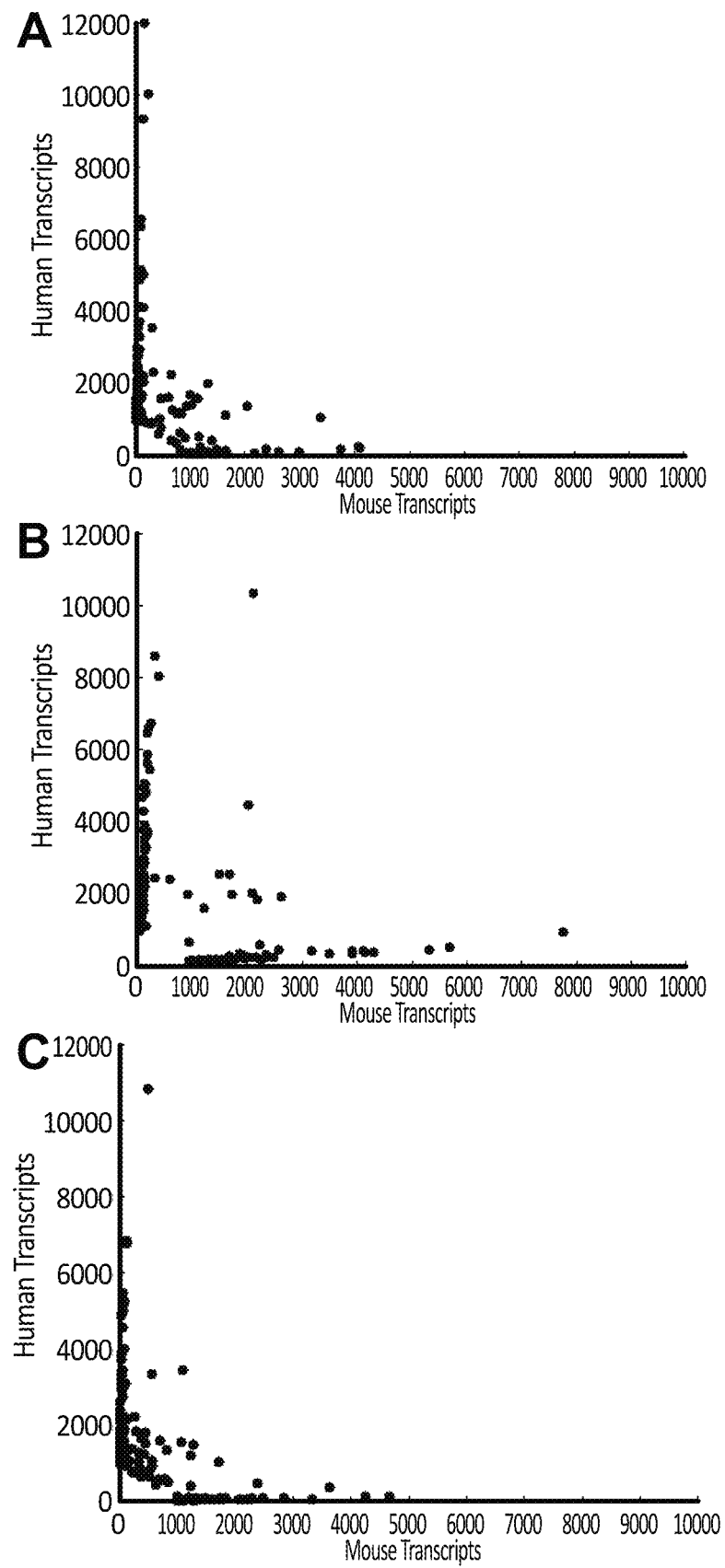

FIGS. 28A-28C illustrate the effect of doping of ionic functional group with carboxylic acid functional groups (see FIG. 16). (A) MicroTEC species-mixing experiment, 10% carboxylate doping. (B) MicroTEC species-mixing experiment, 20% carboxylate doping. (C) PDMS species-mixing experiment, no doping.

Figure 29:
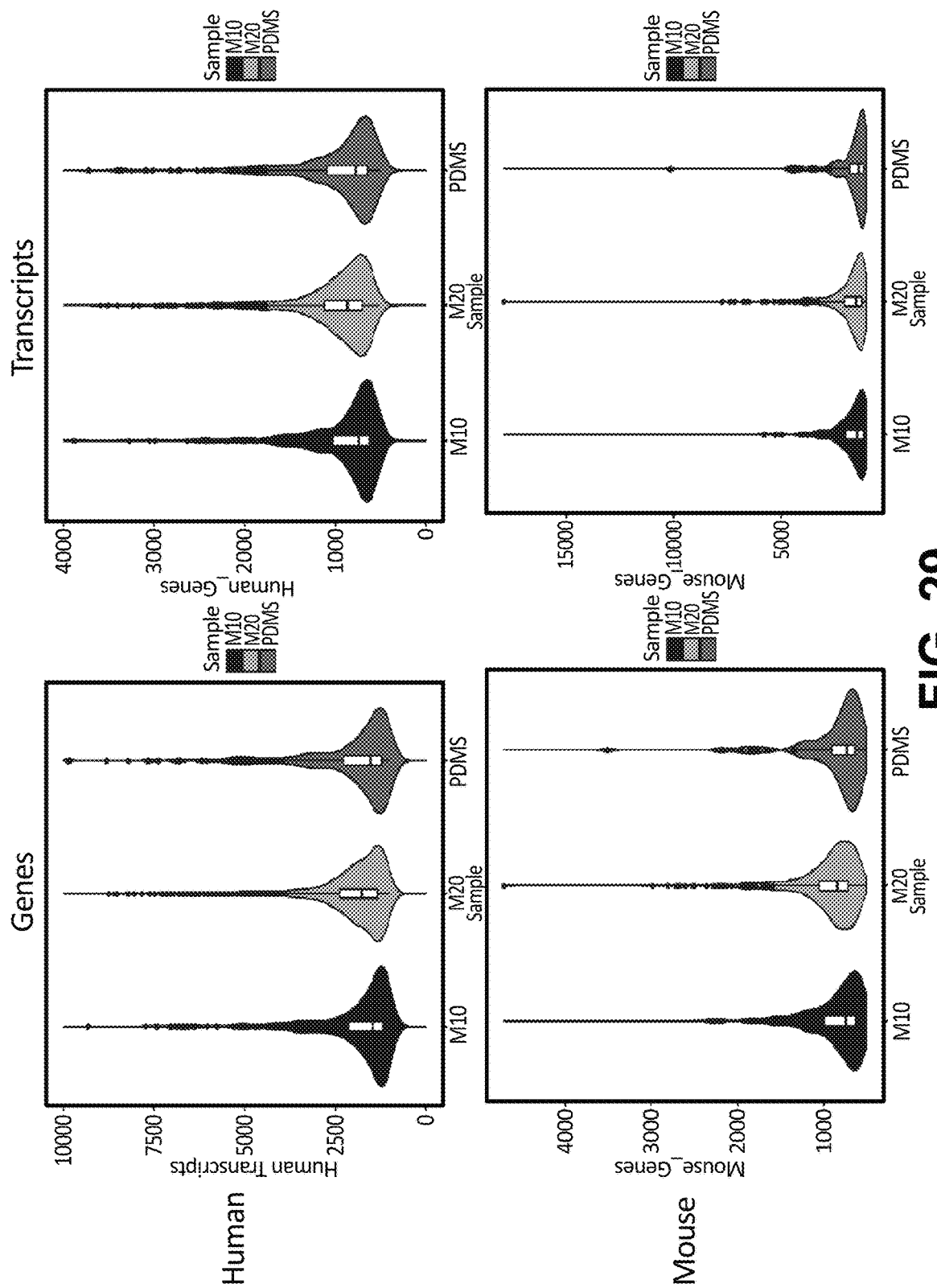

FIG. 29 illustrates gene, transcripts and cell yields. M10: MicroTEC, 10% carboxylate doping. M20: MicroTEC, 20% carboxylate doping. PDMS: PDMS, no doping.

DETAILED DESCRIPTION OF THE INVENTION

The present application provides a method of assembling a container for biochemical analysis, multiple steps of biochemical analysis, or multiple parallel steps of biochemical analysis on one or more cells comprising performing molecular bonding of a porous membrane on an apical or basal surface of an array having a plurality of wells, wherein the molecular bonding substantially isolates each well from adjacent wells or a subset of wells.

Applicants provide a methodology which allows attachment of a porous membrane to a container in conditions which are benign to living cells. Combined with arrays of picoliter-scale volume containers made, for example, in PDMS, the invention provides the creation of hundreds of thousands of isolated dialysis chambers which can be used for many different applications. In a related aspect of the invention, Applicants provide single cell lysis procedures for single cell RNA-seq, whole genome amplification or proteome capture; highly multiplexed single cell nucleic acid preparation (~100× increase over current approaches); highly parallel growth of clonal bacterial populations thus providing synthetic biology applications as well as basic recombinant protein expression; selection of bacterial that have increased secretion of a recombinant product possible product could also be small molecule metabolite which could have considerable utility in chemical industry and biofuels; retention of cells during multiple microengraving events'; long term capture of secreted products from single cells; and screening of cellular events. Principles of the present methodology allow for addition and subtraction of materials from the containers, which has not previously been available on the present scale in other modalities.

Applicants have established chemistries that enable the stable attachment of porous membranes to PDMS nanowell devices in conditions that do not affect cells. Applicants have established multiple chemistries to attach the membranes. In a preferred embodiment, Applicants have selected is to functionalize the PDMS device with an amino-silane and oxidize the membrane with plasma. Applicants have found that the selected functional group provides facile pH modification. With regard to general cell culture uses, the PDMS is amine functionalized by air plasma treatment followed by submersion in an aqueous solution of poly(lysine) followed by baking at 80° C. For processes that require robust denaturing conditions, the amine must be covalently linked to the surface. This is accomplished by treating the PDMS with air plasma, followed by submersion in an ethanol solution of amine-silane, followed by baking at 80° C., followed by submersion in 0.2% phenylene diisothiocyanate (PDITC) DMF/pyridine solution, followed by baking, followed by submersion in chitosan or poly(lysine) solution. For functionalization of the membrane for protein capture, membrane can be amine-silanized using vapor deposition and then treated in solution with NHS-biotin or NHS-maleimide to turn the amine groups into the crosslinking species.

After functionalization, the devices are loaded with cells (bacterial, mammalian or yeast) in compatible buffers. The cell laden device is then brought in contact with the functionalized membrane using a clamping device. A plain glass slide is placed on top of the membrane in the clamp to provide force for bringing the two surfaces together. After an hour incubation, as one hour is a preferred time span, the clamp is opened and the glass slide is removed. The device can then be submerged in any aqueous buffer for days without the membrane detaching, enabling repetitive measurements of the cells without any cell loss. The covalently-linked membrane is stable in many harsh buffers including guanidine hydrochloride which can be used to robustly lyse cells. If the pore size of the membrane is small, the products from the lysed cells will be retained in each well. The lysing buffer can be washed out and replaced with a different buffer which allows binding of biomolecules to probes preloaded in the wells. The membrane can then be removed, enabling addition of enzymes to reverse transcribe or amplify nucleic acids captured in the wells after lysis. Importantly, the chemistry enables removal of one membrane and replacement with a membrane with a different pore size to enable integration of multiple activities on the same array.

As discussed, while the platform has been optimized for the generation of individually barcoded single-cell sequencing libraries following confinement of cells and mRNA capture beads (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214), it is capable of multiple levels of data acquisition. The platform is compatible with other assays and measurements performed with the same array. For example, profiling of human antibody responses by integrated single-cell analysis is discussed with regard to measuring levels of cell surface proteins (Ogunniyi, A. O., B. A. Thomas, T. J. Politano, N. Varadarajan, E. Landais, P. Poignard, B. D. Walker, D. S. Kwon, and J. C. Love, "Profiling Human Antibody Responses by Integrated Single-Cell Analysis" Vaccine, 32(24), 2866-2873.) The authors demonstrate a complete characterization of the antigen-specific B cells induced during infections or following vaccination, which enables and informs one of skill in the art how interventions shape protective humoral responses. Specifically, this disclosure combines single-cell profiling with on-chip image cytometry, microengraving, and single-cell RT-PCR.

In a related aspect, mention is made of leveraging the present platform for use with secreted proteins. Examples of the technology disclosed herein may be used to identify secreted products (e.g., proteins) with a printed microarray (see, e.g., U.S. Pat. Nos. 7,776,553; 8,835,187; 8,772,049; 8,865,479; JP 571822; EP 2 297 333; U.S. application Ser. No. 13/132,858).

In other examples, other technologies have been cited as a method of providing a method of analyzing interactions between pairs of target and effector cells utilizing high-throughput screenings methods for profiling large numbers of single cells in microarrays (see, e.g., U.S. application Ser. No. 13/145,300). The present microwell technology provides one of skill in the art to profile cytolytic behaviors of cells and link multiple levels of biological information to single-cell sequencing data, or other genomic data or other downstream measurements, obtained from the Seq-well platform.

With regard to the analyte or samples discussed herein, cells come in different types, sub-types and activity states, which are classify based on their shape, location, function, or molecular profiles, such as the set of RNAs that they express. RNA profiling is in principle particularly informative, as cells express thousands of different RNAs. Approaches that measure for example the level of every type of RNA have until recently been applied to "homogenized" samples—in which the contents of all the cells are mixed together. Methods to profile the RNA content of tens and hundreds of thousands of individual human cells have been recently developed, including from brain tissues, quickly and inexpensively. To do so, special microfluidic devices have been developed to encapsulate each cell in an individual drop, associate the RNA of each cell with a 'cell barcode' unique to that cell/drop, measure the expression level of each RNA with sequencing, and then use the cell barcodes to determine which cell each RNA molecule came from. See, e.g., U.S. 62/048,227 filed Sep. 9, 2014.

A major determinant of each cell's function is its transcriptional program. Recent advances now enable mRNA-seq analysis of individual cells (Kurimoto K., et al., "An improved single-cell cDNA amplification method for efficient high-density oligonucleotide microarray analysis" (2006) Nucleic Acids Research, 34(5):e42; Tang F., et al., "mRNA-Seq whole-transcriptome analysis of a single-cell" (2009) Nature Methods 6(5): 377-82). HoFIGS.ver, current methods of preparing cells for profiling are applied to hundreds (Hashimshony T., et al., "CEL-Seq: single-cell RNA-Seq by multiplexed linear amplification" (2012) Cell reports 2, 666-673), Islam, S. et al., "Quantitative single-cell RNA-seq with unique molecular identifiers" (2012) Nature Methods 11, 163-166; Picelli S., et al., "Smart-seq2 for sensitive full-length transcriptome profiling in single cells" (2013) Nature Methods 10, 1096-98; Pollen, A., et al., "Low-coverage single-cell mRNA sequencing reveals cellular heterogeneity and activated signaling pathways in developing cerebral cortex" (2014) Nature Biotechnology 32, 1053-58; Shalek, A., et al., "Single-cell RNA-seq reveals dynamic paracrine control of cellular variation" (2014) Nature 510, 363-69) or (with automation) a few thousand cells (Jaitin, D., et al., "Massively parallel single-cell RNA-seq for marker-free decomposition of tissues into cell types" (2014) Science 343, 776-779), typically after first separating the cells by sorting (Shalek, A. K., Satija, R., Adiconis, X., Gertner, R. S., Gaublomme, J. T., Raychowdhury, R., Schwartz, S., Yosef, N., Malboeuf, C., Lu, D., et al. (2013). Single-cell transcriptomics reveals bimodality in expression and splicing in immune cells. Nature 498, 236-240), picking (Hashimshony T., et al., "CEL-Seq: single-cell RNA-Seq by multiplexed linear amplification" (2012) Cell reports 2, 666-673), or microfluidics (Shalek, A. K., Satija, R., Shuga, J., Trombetta, J. J., Gennert, D., Lu, D., Chen, P., Gertner, R. S., Gaublomme, J. T., Yosef, N., et al. "Single-cell RNA-seq reveals dynamic paracrine control of cellular variation" (2014) Nature 510, 363-369), and then amplifying each cell's transcriptome in its own well or microfluidics chamber. Scalable approaches will be needed to characterize complex tissues with many cell types and states, under diverse conditions and perturbations. Profiling large numbers of cells may also be important for distinguishing noise from biologically meaningful patterns (sometimes involving small numbers of genes) that recur in many cells (Grun, D., et al., "Validation of noise models for single-cell transcriptomics" (2014) Nature Methods 11, 637-640; Kharchenko, P., et al., "Bayesian approach to single-cell differential expression analysis" (2014) Nature Methods 11, 740-742).

Single Cell Profiling

Single-cell profiling is a technique that exposes inherent responses which otherwise are unable to be studied in the context of a complex, and non-uniform environment. Biological samples, such as tissue, are broken down in order to study cell types and reveal pertinent cell expression profiles. Currently, techniques used for single-cell profiling entail quantitative reverse transcription PCR (RT-qPCR) and single-cell RNA-Seq, as well as other single-cell genomic techniques. RT-qPCR provides a highly sensitive, high-throughput single-cell profiling technique with multiplexing developed to target mRNA, microRNA, non-coding RNA, and proteins. (Stahlberg, A; Kubista, M. Expert Rev. Mol. Diagn. 14(3), 323-331 (2014).

Performing studies that require data resolution at the single cell (or single molecule) level can be challenging or cost prohibitive under the best circumstances. Although techniques or instruments for single molecule or single cell analysis exist (e.g., digital polymerase chain reactions (PCR) or Fluidigm C1, respectively), none currently allows a scalable method for dynamically delivering reagents and/or appending molecular "information" to individual reactions such that a large population of reactions/assays can be processed and analyzed en masse while still maintaining the ability to partition results by individual reactions/assays. (mention is made of Mazutis, L., Gilbert, J., Ung, W. L., Weitz, D. A., Griffiths, A. D., and Heyman, J. A. (2013). Single-cell analysis and sorting using droplet-based microfluidics. Nature protocols 8, 870-891.)

Microfluidics involves micro-scale devices that handle small volumes of fluids. Because microfluidics may accurately and reproducibly control and dispense small fluid volumes, in particular volumes less than 1 μl, application of microfluidics provides significant cost-savings. The use of microfluidics technology reduces cycle times, shortens time-to-results, and increases throughput. Furthermore, incorporation of microfluidics technology enhances system integration and automation. Microfluidic reactions are generally conducted in microdroplets. The ability to conduct reactions in microdroplets depends on being able to merge different sample fluids and different microdroplets. See, e.g., US Patent Publication No. 20120219947.

Droplet microfluidics offers significant advantages for performing high-throughput screens and sensitive assays. Droplets allow sample volumes to be significantly reduced, leading to concomitant reductions in cost. Manipulation and measurement at kilohertz speeds enable up to $10^8$ discrete biological entities (including, but not limited to, individual cells or organelles) to be screened in a single day. Compartmentalization in droplets increases assay sensitivity by increasing the effective concentration of rare species and decreasing the time required to reach detection thresholds. Droplet microfluidics combines these powerful features to enable currently inaccessible high-throughput screening applications, including single-cell and single-molecule assays. See, e.g., Guo et al., Lab Chip, 2012, 12, 2146-2155.

Drop-Sequence methods and apparatus provides a high-throughput single-cell RNA-Seq and/or targeted nucleic acid profiling (for example, sequencing, quantitative reverse transcription polymerase chain reaction, and the like) where the RNAs from different cells are tagged individually, allowing a single library to be created while retaining the cell identity of each read. A combination of molecular barcoding and emulsion-based microfluidics to isolate, lyse, barcode, and prepare nucleic acids from individual cells in high-throughput is used. Microfluidic devices (for example, fabricated in polydimethylsiloxane), sub-nanoliter reverse emulsion droplets. These droplets are used to co-encapsulate nucleic acids with a barcoded capture bead. Each bead, for example, is uniquely barcoded so that each drop and its contents are distinguishable. The nucleic acids may come from any source known in the art, such as for example, those which come from a single cell, a pair of cells, a cellular lysate, or a solution. The cell is lysed as it is encapsulated in the droplet. To load single cells and barcoded beads into these droplets with Poisson statistics, 100,000 to 10 million such beads are needed to barcode ~10,000-100,000 cells.

In some aspects of the invention, the present application enables one to capture mRNA transcripts from single cells using the methods described. Mention is made of mRNA transcript capture from single cells using microfluidic devices. In a report by Walsh et al. Lab Chip, 2015, 15, 2968-2980, the disclosure relates to a microfluidic device for automatic hydrodynamic capture of single mammalian cells and subsequent immobilization and digital counting of polyadenylated mRNA molecules released from individual cells (see Abstract). Single HeLA cells are captured by hybridization to oligonucleotides attached on the glass surface in the device, which is visually monitored using single-molecule fluorescence imaging.

The present application expounds upon OPENARRAY® technology and enables one to couple OPENARRAY® technology with the currently described methods. Generally, OPENARRAY® technology uses a microscope slide-sized plate with 3,072 through-holes. Each plate contains 48 subarrays, each with 64 through-holes where each through-hole is 300 μm in diameter and 300 μm deep and is treated with hydrophilic and hydrophobic coatings. Reagents are retained in the through-holes via surface tension. The technology allows for real-time PCR based solution for high-throughput gene expression analysis, genotyping, microRNA analysis, and digital PCR applications.

Semi-Permeable Membranes

In some aspects of the invention, semi-permeable membranes refer to thin layers or coverings which allow certain compounds, molecules, ions, or proteins to pass through via diffusion. In some aspects the diffusion requires energy to pass through the membrane and is sometimes referred to as active transport. In other aspects, the invention is practiced with a semi-permeable membrane including pores which may be used to separate a material with a specific size. As a result, such a semi-permeable or separation membrane may be applied to biological analysis by using this property to remove any undesired components. A semi-permeable membrane is also termed a selectively permeable membrane, a partially permeable membrane or a differentially permeable membrane, and is a type of membrane, e.g., biological membrane, that may allow certain molecules or ions to pass through it, e.g., by diffusion or facilitated diffusion or passive transport or active transport; accordingly, a membrane as in the present invention or as meeting criteria as herein discussed may be considered permeable, or semi-permeable, or selectively permeable or partially permeable or differentially permeable, or a biological membrane, or a membrane that allows certain molecules or ions to pass through it, or a membrane that allows certain molecules or ions to pass through it by diffusion, or a membrane that allows certain molecules or ions to pass through it by facilitated diffusion, or a membrane that allows certain molecules or ions to pass through it by passive transport, or a membrane that allows certain molecules or ions to pass through it by active transport. The membrane for biological analysis may be divided into various types according to the size of the micropores (including a microfiltration membrane, an ultrafiltration membrane, a nanofiltration membrane, a reverse osmotic membrane, and the like). These membranes have characteristics determined according to the characteristics of the pores formed therein. For example, a membrane with relatively high porosity may decrease driving pressure but may have lower physical strength. On the contrary, a membrane with relatively low porosity may have higher physical strength but may increase driving pressure. Additionally, the pores of such a membrane may be more densely distributed to facilitate selective separation of a material having a specific size. In an embodiment of the invention, the membrane may be assembled in a layer-by-layer fashion. The layer-by-layer assembly may form a functional multi-layered thin membrane by alternatively combining a polymer electrolyte, nanoparticles, particles, proteins, large organic molecules, and the like having a positive ion charge with another polymer electrolyte, nanoparticles, nanoparticles, particles, proteins, large organic molecules, and the like having a negative ion charge through molecular attraction including, but not limited to, electrostatic attraction, hydrogen bonding, and electron transfer.

Ultrafiltration

In an aspect of the invention, methods are described which entails ultrafiltration. Membrane filtration comprises ultrafiltration, where pressure and/or concentration gradients enable separation of analytes through a semipermeable membrane. Ultrafiltration is applicable for the purification of protein solutions, where membranes are defined by a molecular weight cut off in order to provide the separation of the desired proteins.

Ultrafiltration leverages the relationship between applied pressure on the solution to be separated and the flux through the membrane described by the equation:

$$J = \frac{TMP}{\mu R_t}$$

where J represents the flux, TMP represents the transmembrane pressure, is solvent viscosity, and Rt is the sum of membrane and fouling resistance. Membrane fouling is a process wherein a solution or a particle is deposited on a membrane surface and/or the membrane pores such that the deposition the membrane performance is degraded.

One of skill in the art is familiar with and may employ different labeling substances in connection with the apparatus, compositions, kits, and methods described herein, such as fluorescent dyes, enzymes, coenzymes, chemiluminescent substances, and radioactive substances. Specific examples include radioisotopes (e.g., 32P, 14C, 125I, 3H, and 131I), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and ruthenium. In the case where biotin is employed as a labeling substance, preferably, after addition of a biotin-labeled antibody, streptavidin bound to an enzyme (e.g., peroxidase) is further added.

Advantageously, the label is a fluorescent label. Examples of fluorescent labels include, but are not limited to, Atto dyes, 4-acetamido-4'-isothiocyanatostilbene-2,2'disulfonic acid; acridine and derivatives: acridine, acridine isothiocyanate; 5-(2'-aminoethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives; coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5''-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresolphthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N',N' tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine.

The fluorescent label may be a fluorescent protein, such as blue fluorescent protein, cyan fluorescent protein, green fluorescent protein, red fluorescent protein, yellow fluorescent protein or any photoconvertible protein. Colormetric labeling, bioluminescent labeling and/or chemiluminescent labeling may further accomplish labeling. Labeling further may include energy transfer between molecules in the hybridization complex by perturbation analysis, quenching, or electron transport between donor and acceptor molecules, the latter of which may be facilitated by double stranded match hybridization complexes. The fluorescent label may be a perylene or a terylene. In the alternative, the fluorescent label may be a fluorescent bar code.

The oligonucleotide tags may be detectable by virtue of their nucleotide sequence, or by virtue of a non-nucleic acid detectable moiety that is attached to the oligonucleotide such as but not limited to a fluorophore, or by virtue of a combination of their nucleotide sequence and the non-nucleic acid detectable moiety.

In some embodiments, a detectable oligonucleotide tag may comprise one or more nonoligonucleotide detectable moieties. Examples of detectable moieties may include, but are not limited to, fluorophores, microparticles including quantum dots (Empodocles, et al., Nature 399:126-130, 1999), gold nanoparticles (Reichert et al., Anal. Chem. 72:6025-6029, 2000), microbeads (Lacoste et al., Proc. Natl. Acad. Sci. USA 97(17):9461-9466, 2000), biotin, DNP (dinitrophenyl), fucose, digoxigenin, haptens, and other detectable moieties known to those skilled in the art. In some embodiments, the detectable moieties may be quantum dots. Methods for detecting such moieties are described herein and/or are known in the art.

Thus, detectable oligonucleotide tags may be, but are not limited to, oligonucleotides which may comprise unique nucleotide sequences, oligonucleotides which may comprise detectable moieties, and oligonucleotides which may comprise both unique nucleotide sequences and detectable moieties.

A unique label may be produced by sequentially attaching two or more detectable oligonucleotide tags to each other. The detectable tags may be present or provided in a plurality of detectable tags. The same or a different plurality of tags may be used as the source of each detectable tag may be part of a unique label. In other words, a plurality of tags may be subdivided into subsets and single subsets may be used as the source for each tag.

In some embodiments, one or more other species may be associated with the tags. In particular, nucleic acids released by a lysed cell may be ligated to one or more tags. These may include, for example, chromosomal DNA, RNA transcripts, tRNA, mRNA, mitochondrial DNA, or the like. Such nucleic acids may be sequenced, in addition to sequencing the tags themselves, which may yield information about the nucleic acid profile of the cells, which can be associated with the tags, or the conditions that the corresponding droplet or cell was exposed to.

In one aspect single cells or single organelles or single molecules (proteins, RNA, DNA) are encapsulated into containers, chambers, or wells from an aqueous solution/dispersion. In a related aspect, multiple cells or multiple molecules may take the place of single cells or single molecules. The aqueous droplets of volume ranging from 1 pL to 10 nL work as individual reactors.

Methods for producing droplets of a uniform volume at a regular frequency are well known in the art. One method is to generate droplets using hydrodynamic focusing of a dispersed phase fluid and immiscible carrier fluid, such as disclosed in U.S. Publication No. US 2005/0172476 and International Publication No. WO 2004/002627. It is desirable for one of the species introduced at the confluence to be a pre-made library of droplets where the library contains a plurality of reaction conditions, e.g., a library may contain plurality of different compounds at a range of concentrations encapsulated as separate library elements for screening their effect on cells or enzymes, alternatively a library could be composed of a plurality of different primer pairs encapsulated as different library elements for targeted amplification of a collection of loci, alternatively a library could contain a plurality of different antibody species encapsulated as different library elements to perform a plurality of binding assays. Principles of the present invention allow for library construction. The introduction of a library of reaction conditions onto a substrate is achieved by pushing a premade collection of library droplets out of a vial with a drive fluid. The drive fluid is a continuous fluid. The drive fluid may comprise the same substance as the carrier fluid (e.g., a fluorocarbon oil). For example, if a library consists of ten picoliter droplets is driven into an inlet channel on a microfluidic substrate with a drive fluid at a rate of 10,000 picoliters per second, then nominally the frequency at which the droplets are expected to enter the confluence point is 1000 per second. However, in practice droplets pack with oil between them that slowly drains. Over time the carrier fluid drains from the library droplets and the number density of the droplets (number/mL) increases. Hence, a simple fixed rate of infusion for the drive fluid does not provide a uniform rate of introduction of the droplets into the microfluidic channel in the substrate. Moreover, library-to-library variations in the mean library droplet volume result in a shift in the frequency of droplet introduction at the confluence point. Thus, the lack of uniformity of droplets that results from sample variation and oil drainage provides another problem to be solved. For example, if the nominal droplet volume is expected to be 10 picoliters in the library, but varies from 9 to 11 picoliters from library-to-library then a 10,000 picoliter/second infusion rate will nominally produce a range in frequencies from 900 to 1,100 droplet per second. In short, sample to sample variation in the composition of dispersed phase for droplets made on chip, a tendency for the number density of library droplets to increase over time and library-to-library variations in mean droplet volume severely limit the extent to which frequencies of droplets may be reliably matched at a confluence by simply using fixed infusion rates. In addition, these limitations also have an impact on the extent to which volumes may be reproducibly combined. Combined with typical variations in pump flow rate precision and variations in channel dimensions, systems are severely limited without a means to compensate on a run-to-run basis. The foregoing facts not only illustrate a problem to be solved, but also demonstrate a need for a method of instantaneous regulation of microfluidic control over microdroplets within a microfluidic channel.

A cell library element may include, but is not limited to, hybridomas, B-cells, primary cells, cultured cell lines, cancer cells, stem cells, cells obtained from tissue, or any other cell type. Cellular library elements are prepared by encapsulating a number of cells from one to hundreds of thousands in individual droplets. The number of cells encapsulated is usually given by Poisson statistics from the number density of cells and volume of the droplet. However, in some cases the number deviates from Poisson statistics as described in Edd et al., "Controlled encapsulation of single-cells into monodisperse picolitre drops." Lab Chip, 8(8): 1262-1264, 2008. The discrete nature of cells allows for libraries to be prepared in mass with a plurality of cellular variants all present in a single starting media and then that media is broken up into individual droplet capsules that contain at most one cell. These individual droplets capsules are then combined or pooled to form a library consisting of unique library elements. Cell division subsequent to, or in some embodiments following, encapsulation produces a clonal library element.

A bead based library element may contain one or more beads, of a given type and may also contain other reagents, such as antibodies, enzymes or other proteins. In the case where all library elements contain different types of beads, but the same surrounding media, the library elements may all be prepared from a single starting fluid or have a variety of starting fluids. In the case of cellular libraries prepared in mass from a collection of variants, such as genomically modified, yeast or bacteria cells, the library elements will be prepared from a variety of starting fluids.

A large variety of elastomeric materials may be used in fabrication of the devices of the invention. Elastomers in general are polymers existing at a temperature between their glass transition temperature and liquefaction temperature. For illustration, a brief description of the most common classes of elastomers is presented below.

Silicone polymers have great structural variety, and a large number of commercially available formulations. In an exemplary aspect of the present invention, the present systems are fabricated from an elastomeric polymer such as GE® RTV 615 (formulation), a vinyl-silane crosslinked (type) silicone elastomer (family). In one embodiment, the silicone polymer is polydimethylsiloxane (PDMS).

Functionalized photocurable perfluoropolyether (PFPE) is particularly useful as a material for fabricating solvent-resistant microfluidic devices for use with certain organic solvents. These PFPEs have material properties and fabrication capabilities similar to PDMS but with compatibility with a broader range of solvents. Suitable PFPE compounds are described, for example, in International Publication Nos. WO 2005/030822 and WO 2005/084191 and Rolland et al., "Solvent-resistant photocurable 'liquid Teflon' for microfluidic device fabrication," 126 J. Amer. Chem. Soc. 2322-23 (2004).

Other suitable materials include polyisoprenes, polybutadienes, polychloroprenes, polyisobutylenes, poly(styrene-butadiene-styrene)s, polyurethanes, poly(bis(fluoroalkoxy) phosphazene) (PNF, Eypel-F), poly(carborane-siloxanes) (e.g., Dexsil), poly(acrylonitrile-butadiene) (nitrile rubber), poly(1-butene), poly(chlorotrifluoroethylene-vinylidene fluoride) copolymers (Kel-F), poly(ethyl vinyl ether), poly (vinylidene fluoride), poly(vinylidene fluoride-hexafluoropropylene) copolymer (available, for example, under the VITON® trademark), elastomeric compositions of polyvinylchloride (PVC), polysulfone, polycarbonate, polymethylmethacrylate (PMMA), and polytetrafluoroethylene (available, for example, under the TEFLON® trademark).

Applicants contemplate use of micro-sized arrays and nano-sized arrays. Generally, micro-sized arrays refer to (sub) nanoliter-scale volumes. For arrays with linear dimensions which range anywhere from 1 μm to 1,000 μm, the volumes are on the order of 1 pL to 1 nL, generally. Therefore, linear dimensions and volumetric dimensions are referred to discretely.

One of skill in the art will recognize that methods and systems of the invention are not limited to any particular type of sample, and methods and systems of the invention may be used with any type of organic, inorganic, or biological molecule (see, e.g, US Patent Publication No. 20120122714). In particular embodiments the sample may include nucleic acid target molecules. Nucleic acid molecules may be synthetic or derived from naturally occurring sources. In one embodiment, nucleic acid molecules may be isolated from a biological sample containing a variety of other components, such as proteins, lipids and non-template nucleic acids. Nucleic acid target molecules may be obtained from any cellular material, obtained from an animal, plant, bacterium, fungus, or any other cellular organism. In certain embodiments, the nucleic acid target molecules may be obtained from a single cell. Biological samples for use in the present invention may include viral particles or preparations. Nucleic acid target molecules may be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the invention. Nucleic acid target molecules may also be isolated from cultured cells, such as a primary cell culture or a cell line. The cells or tissues from which target nucleic acids are obtained may be infected with a virus or other intracellular pathogen. A sample may also be total RNA extracted from a biological specimen, a cDNA library, viral, or genomic DNA.

Generally, nucleic acid may be extracted from a biological sample by a variety of techniques such as those described by Maniatis, et al., Molecular Cloning: A Laboratory Manual, Cold Spring Harbor, N.Y., pp. 280-281 (1982). Nucleic acid molecules may be single-stranded, double-stranded, or double-stranded with single-stranded regions (for example, stem- and loop-structures).

Nucleic acid obtained from biological samples typically may be fragmented to produce suitable fragments for analysis. Target nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In one embodiment, nucleic acid from a biological sample is fragmented by sonication. In another embodiment, nucleic acid is fragmented by a hydroshear instrument. Generally, individual nucleic acid target molecules may be from about 40 bases to about 40 kb. Nucleic acid molecules may be single-stranded, double-stranded, or double-stranded with single-stranded regions (for example, stem- and loop-structures).

A biological sample as described herein may be homogenized or fractionated in the presence of a detergent or surfactant. The concentration of the detergent in the buffer may be about 0.05% to about 10.0%. The concentration of the detergent may be up to an amount where the detergent remains soluble in the solution. In one embodiment, the concentration of the detergent is between 0.1% to about 2%. The detergent, particularly a mild one that is nondenaturing, may act to solubilize the sample. Detergents may be ionic or nonionic. Examples of nonionic detergents include triton, such as the Triton™ X series (Triton™ X-100 t-Oct-$C_6H_4$—($OCH_2$—$CH_2$)$_x$OH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™. 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14E06), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulfonate. It is contemplated also that urea may be added with or without another detergent or surfactant.

Lysis or homogenization solutions may further contain other agents, such as reducing agents. Examples of such reducing agents include dithiothreitol (DTT), β-mercaptoethanol, DTE, GSH, cysteine, cysteamine, tricarboxyethyl phosphine (TCEP), or salts of sulfurous acid.

Size selection of the nucleic acids may be performed to remove very short fragments or very long fragments. The nucleic acid fragments may be partitioned into fractions which may comprise a desired number of fragments using any suitable method known in the art. Suitable methods to limit the fragment size in each fragment are known in the art. In various embodiments of the invention, the fragment size is limited to between about 10 and about 100 Kb or longer.

Extraction or isolation of individual proteins, protein complexes, proteins with translational modifications, and protein/nucleic acid complexes is performed using methods known in the art.

Applications of the disclosed device may include use for the dynamic generation of molecular barcodes (e.g., DNA oligonucleotides, fluorophores, etc.) either independent from or in concert with the controlled delivery of various compounds of interest (drugs, small molecules, siRNA, CRISPR guide RNAs, reagents, etc.). For example, unique molecular barcodes can be created in one array of nozzles while individual compounds or combinations of compounds can be generated by another nozzle array. Barcodes/compounds of interest can then be merged with cell-containing droplets. An electronic record in the form of a computer log file is kept to associate the barcode delivered with the downstream reagent(s) delivered. This methodology makes it possible to efficiently screen a large population of cells for applications such as single-cell drug screening, controlled perturbation of regulatory pathways, etc. The device and techniques of the disclosed invention facilitate efforts to perform studies that require data resolution at the single cell (or single molecule) level and in a cost effective manner.

A plurality of biological assays as well as biological synthesis are contemplated for the present invention.

In an advantageous embodiment, polymerase chain reactions (PCR) are contemplated (see, e.g., US Patent Publication No. 20120219947). Methods of the invention may be used for merging sample fluids for conducting any type of chemical reaction or any type of biological assay. In certain embodiments, methods of the invention are used for merging sample fluids for conducting an amplification reaction in a droplet. Amplification refers to production of additional copies of a nucleic acid sequence and is generally carried out using polymerase chain reaction or other technologies well known in the art (e.g., Dieffenbach and Dveksler, PCR Primer, a Laboratory Manual, Cold Spring Harbor Press, Plainview, N.Y. [1995]). The amplification reaction may be any amplification reaction known in the art that amplifies nucleic acid molecules, such as polymerase chain reaction, nested polymerase chain reaction, polymerase chain reaction-single strand conformation polymorphism, ligase chain reaction (Barany F. "Genetic disease detection and DNA amplification using cloned thermostable ligase" (1991) PNAS 88:189-193; Barany F. "The ligase chain reaction in a PCR world." (1991) PCR Methods and Applications 1:5-16), ligase detection reaction (Barany F. "Genetic disease detection and DNA amplification using cloned thermostable ligase" (1991) PNAS 88:189-193), strand displacement amplification and restriction fragments length polymorphism, transcription based amplification system, nucleic acid sequence-based amplification, rolling circle amplification, and hyper-branched rolling circle amplification.

In certain embodiments, the amplification reaction is the polymerase chain reaction. Polymerase chain reaction (PCR) refers to methods by K. B. Mullis (U.S. Pat. Nos. 4,683,195 and 4,683,202, hereby incorporated by reference) for increasing concentration of a segment of a target sequence in a mixture of genomic DNA without cloning or purification. The process for amplifying the target sequence includes introducing an excess of oligonucleotide primers to a DNA mixture containing a desired target sequence, followed by a precise sequence of thermal cycling in the presence of a DNA polymerase. The primers are complementary to their respective strands of the double stranded target sequence.

To effect amplification, primers are annealed to their complementary sequence within the target molecule. Following annealing, the primers are extended with a polymerase so as to form a new pair of complementary strands. The steps of denaturation, primer annealing and polymerase extension may be repeated many times (i.e., denaturation, annealing and extension constitute one cycle; there may be numerous cycles) to obtain a high concentration of an amplified segment of a desired target sequence. The length of the amplified segment of the desired target sequence is determined by relative positions of the primers with respect to each other, and therefore, this length is a controllable parameter.

Methods for performing PCR in droplets are shown for example in Link et al. (U.S. Patent application numbers 2008/0014589, 2008/0003142, and 2010/0137163), Anderson et al. (U.S. Pat. No. 7,041,481 and which reissued as RE41,780) and European publication number EP2047910 to Raindance Technologies Inc. The content of each of which is incorporated by reference herein in its entirety.

Primers may be prepared by a variety of methods including but not limited to cloning of appropriate sequences and direct chemical synthesis using methods well known in the art (Narang et al., Methods Enzymol., 68:90 (1979); Brown et al., Methods Enzymol., 68:109 (1979)). Primers may also be obtained from commercial sources such as Operon Technologies, Amersham Pharmacia Biotech, Sigma, and Life Technologies. The primers may have an identical melting temperature. The lengths of the primers may be extended or shortened at the 5' end or the 3' end to produce primers with desired melting temperatures. Also, the annealing position of each primer pair may be designed such that the sequence and, length of the primer pairs yield the desired melting temperature. The simplest equation for determining the melting temperature of primers smaller than 25 base pairs is the Wallace Rule ($Td=2(A+T)+4(G+C)$). Computer programs may also be used to design primers, including but not limited to Array Designer Software (Arrayit Inc.), Oligonucleotide Probe Sequence Design Software for Genetic Analysis (Olympus Optical Co.), NetPrimer, and DNAsis from Hitachi Software Engineering. The TM (melting or annealing temperature) of each primer is calculated using software programs such as Oligo Design, available from Invitrogen Corp.

In certain embodiments, the three temperature zones are used for the amplification reaction. The three temperature zones are controlled to result in denaturation of double stranded nucleic acid (high temperature zone), annealing of primers (low temperature zones), and amplification of single stranded nucleic acid to produce double stranded nucleic acids (intermediate temperature zones). The temperatures within these zones fall within ranges well known in the art for conducting PCR reactions. See for example, Sambrook et al. (Molecular Cloning, A Laboratory Manual, 3rd edition, Cold Spring Harbor Laboratory Press, Cold Spring Harbor, N.Y., 2001).

In another embodiment, examples of assays are ELISA assays (see, e.g., US Patent Publication No. 20100022414). Prior emulsion libraries may comprise a plurality of aqueous droplets within an immiscible fluorocarbon oil which may comprise at least one fluorosurfactant, wherein each droplet is uniform in size and may comprise at least a first antibody, and a single element linked to at least a second antibody, wherein said first and second antibodies are different. In one example, each library element may comprise a different bead, wherein each bead is attached to a number of antibodies and the bead is encapsulated within a droplet that contains a different antibody in solution. These antibodies may then be allowed to form "ELISA sandwiches," which may be washed and prepared for a ELISA assay. Further, these contents of the droplets may be altered to be specific for the antibody contained therein to maximize the results of the assay. The present methodology allows for sample preparation without the use of oil, which facilitates addition and removal of materials during various sample processing steps.

In another embodiment, single-cell assays are also contemplated as part of the present invention (see, e.g., Ryan et al., Biomicrofluidics 5, 021501 (2011) for an overview of applications of microfluidics to assay individual cells). A single-cell assay may be contemplated as an experiment that quantifies a function or property of an individual cell when the interactions of that cell with its environment may be controlled precisely or may be isolated from the function or property under examination. The research and development of single-cell assays is largely predicated on the notion that genetic variation causes disease and that small subpopulations of cells represent the origin of the disease. Methods of assaying compounds secreted from cells, subcellular components, cell-cell or cell-drug interactions as well as methods of patterning individual cells are also contemplated within the present invention.

Cellularizing

Isolating specific cell types is often desirable for clinical diagnostic and therapeutic applications. In the clinical diagnostics field, there is a need, for example, for morphological analysis of tumor cells, fetal karyotyping, and tissue typing procedures. Therapeutically, there is a need, for example, for purging cells or tissues intended for use in autologous cellular or tissue transfusions or transplantations, e.g. purging tissues of viral antigens and tumor cells. There is also a need for enriching or isolating desirable cells for use in transplantations, e.g. for use in ex vivo expansion of hematopoietic cells intended for allogeneic and autologous transplantation, and for the use in adoptive immunotherapy of potent antigen presenting cells (dendritic cells), cytotoxic T lymphocytes, natural killer (NK) cells and natural suppressor cells.

Several methods are known in the art for separating desirable cells from body fluids. Such methods include separating cells based upon buoyant density in a cell separation composition (U.S. Pat. No. 4,927,750), separating serological factors on density gradients using latex beads coated with antiserological factor (U.S. Pat. No. 3,862,303), separating cells through the use of a magnetic field (U.S. Pat. No. 4,777,145), and separating T and B cells on density gradients (U.S. Pat. No. 4,511,662). Cell separation methods known in the art may have the disadvantage of cell loss due to the sticking of cells to tubes and pipettes.

Fluorescence-activated cell sorting (FACS) is a type of flow cytometry that allows a researcher to separate samples expressing a fluorescence marker from those not expressing the marker. Cells are suspended in a stream of fluid and passing them by an electronic detection apparatus. A heterogeneous mixture of cells can be separated one cell at a time based on the light scattering and the fluorescent characteristics of each cell. The cells are suspended in a narrow, rapidly flowing stream of liquid with a large separation between cells. The stream of cells is formed into individual droplets, preferably with one cell per droplet. Just before the stream breaks into droplets, the flow passes through a fluorescence measuring station where the fluorescent character of interest of each cell is measured. An electrical charging ring is placed just at the point where the stream breaks into droplets. A charge is placed on the ring based on the immediately prior fluorescence intensity measurement, and the opposite charge is trapped on the droplet as it breaks from the stream. The charged droplets then fall through an electrostatic deflection system that diverts droplets into containers based upon their charge.

Magnet-activated cell sorting (MACS) uses superparamagnetic nanoparticles and microfluidic columns to assist in separating and isolating specific cell types and in areas like immunology, cancer research, neuroscience, and stem cell research. Cells are incubated with magnetic nanoparticles coated with antibodies against a particular surface antigen. Cells can be directly labeled or attached to the magnetic nanoparticles if the cells express the particular surface antigen and thus attach to the magnetic nanoparticles. Cells can be indirectly labeled by incubating with a primary antibody directed against a cell surface marker, with magnetic nanoparticles then binding to the primary antibody or to a molecule that is conjugated to the primary antibody.

The labeled cells in solution are then placed in a column and then a strong magnetic field is applied. During separation, the magnetically labeled cells are retained within a column. Unlabeled cells flow through. After a washing step, the column is removed from the magnetic field of the separator, and the target cells are eluted from the column. This is referred to as positive and can be performed by direct or indirect magnetic labeling. The type of nanoparticle can be varied for a specific antigen/molecule binding to allow for capture of different types of cells. Negative selection could alternatively be performed such that the antibody used is against surface antigen(s) which are known to be present on cells that are not of interest. After administration of the cells/magnetic nanoparticles solution onto the column the cells expressing these antigens bind to the column and fraction that goes through is collected, as it contains almost no cells with desired antigens.

In another aspect the present invention provides a diagnostic method for early detection and tracking of a proliferative disease, such as but not limited to cancer progression, by determining the presence of at least one peptide or nucleic acid of the present invention in a patient sample. The patient sample may comprise or be derived from one or more cells or tissues of, without limitation, blood, sputum, saliva, urine, tumor tissue, lymphatic fluid, semen or feces.

The invention provides a diagnostic and method of use, comprising a first functionalized surface of each well or container, wherein the functionalized surface comprises an affinity resin; and a second functionalized surface, such as a top surface of an array material, wherein the functionalized surface provides accessible ionic functional groups. The second surface is configured to be sealed, for example with a permeable membrane, as described herein. According to the invention, the well or container is loaded with one or more cells, such as 1, 2, 3, 4, 5 or more cells of a cell or tissue sample, together with a detection agent, and sealed, for example with a permeable membrane as described herein. In an embodiment of the invention, the detection agent is attached to a barcoded bead. In an embodiment of the invention, the detection reagent is selected to bind to a peptide or nucleic acid. In certain example embodiments, additional reagents may be preloaded into the well or container before sealing. Such reagents can include, without limitation, DNA and/or RNA amplification reagents, polymerases, reverse transcriptase, nucleases, enzymes, antigen binding proteins, labeling reagents, and the like.

In one embodiment, the diagnostic is configured to detect one or more mutated nucleic acids, for example by amplification based methods and/or sequencing. For example, reverse transcription PCR (RT-PCR) can be used to detect mutations in transcribed genes. Additionally, any sequencing technique can be used to determine the presence of a mutation. The present invention also provides for a kit that includes primers that are specific to sequences encompassing the mutations.

Functionalization of Nanoarray

To prepare the PDMS arrays, they are first plasma treated to coat the surface with hydroxyls, giving them a negative charge. The arrays then undergo silanization with APTES, which is the process of covering a surface with organofunctional alkoxysilane molecules—this occurs when the surface hydroxyls attack and displace the silane's alkoxy groups, forming —Si—O—Si— bonds. After successful APTES coating and PDITC-coating step, the array is treated with chitosan, a linear polysaccharide that is derived from chitin, giving the surface an overall positive charge and mitigating the adsorption properties of PDMS.

Functionalization of Membrane

Before the nanowell is sealed, the porous polycarbonate membranes are plasma treated to coat the surface with hydroxyls, giving them a negative charge. These arrays are immediately hydrated, then attached to the nanowell at the appropriate time. Electrostatic bonding or electrostatic attraction of polycarbonate membranes is necessary to maintain attachment and nanowell sealing during the application of harsh lysis buffer. Adding to the complexity of membrane attachment is the need to maintain cell viability during membrane attachment.

Comparatively, attachment of a porous membrane is preferred over use of a glass slide (cited herein) as it allows for efficient buffer exchange.

Hot Embossing

An alternative to using PDMS that mitigates adsorption to arrays is hot embossing, which is the process of imprinting microstructures on a substrate using a master mold. Essentially, these PDMS arrays could be used to imprint microstructures onto substrates like poly(methyl methacrylate) (PMMA), polystyrene, and polypropylene. In doing so, the chemistry used to covalently attach the polycarbonate membrane would be modified according to which substrate is being used. For example, other chemistries suitable for application include: poly(methyl methylacrylate) which enables one to forgo plasma treatment, however it swells and dissolves in many organic solvents, and has poor resistance due to hydrolyzed ester groups.

Pore Size Tolerances

Variation in the pore size of membranes attached to nano-well devices can be used for numerous applications. By controlling pore size, it allows for efficient exchange of buffer solutes while retaining user-selected bulky macromolecules (e.g. cellular proteins, cytokines, nucleic acids, etc.) following cell lysis, limiting loss of molecules of interest and increasing the capture efficiency.

The thickness of membranes used in the current implementation is 10-15 nm, however, increasing membrane thickness could be used to vary the diffusion rate of buffers. An additional modification to membrane design includes membranes that contain pH-sensitive polymers or hydrogels that are capable of altering permeability in response to changes in buffer pH. Importantly, the pH range available is not limited by requirements for cell viability once cells have been lysed.

As one of skill in the art would recognize, other processes for lysing the cell can be employed (e.g., with or without elevating the temperature), the reagents can be added sequentially or together, the cell and the capture substrate can be held in different chambers (e.g., so that the activation chemical is added directly to the capture substrate and does not contact the cell prior to lysis), and the various steps can be conducted in any suitable order, provided that the cellular components are released for capture by the activated capture substrate.

After cell lysis, the enzyme can be neutralized and/or diluted in the mixing circuit. To elevate the temperature of the microfluidic device, any suitable method of controlling the temperature of the device can be used. For example, the device can be placed on a thermocycler to elevate the temperature of the device and maintain a specified temperature of the device. Alternatively, the thermocycler can be set to vary between a lower temperature and a higher temperature over a predetermined period of time. The predetermined period of time can correspond to a minimum amount of time for a cell lysis reaction to occur in the mixing circuit. In other embodiments, the device can be subjected to a lower temperature to cool the device, chemicals, enzymes, fluid, and/or components of the cell. This microfluidic device is well suited for various temperature control solutions through standard lab equipment and without extensive modifications to the equipment.

In an aspect of the invention, the present disclosure relates to porosity. For example, the step of admixing the isolated aggregation of cellular constituents with monomers may be carried out in an aqueous solution, or in an aqueous aliquot or droplet present in an oil emulsion. The polymer matrix may be a hydrogel. The polymer matrix may be any hydrogel capable of polymerization to create a solid matrix that fixes the cellular constituents and provides a porosity capable of allowing labeling ligands to freely diffuse through the network of pores. The cellular constituents may be further fixed by treating with an aldehyde. The aldehyde may be formaldehyde, paraformaldehyde, or glutaraldehyde. Not being bound by a theory the fixation in a solid matrix prevents the mixing of the cellular constituents between the isolated aggregations of cellular constituents. Not being bound by a theory, capturing cellular constituents in a solid polymer mesh ensures that they are physical units that can be ligand and/or antibody stained as a pool and isolated as single cells or isolated aggregates of cellular constituents subsequently. Not being bound by a theory, the fixing of cellular constituents in the polymer matrix allows access to the labeling ligands to intracellular constituents.

In one embodiment, to ensure proper staining of intracellular and cell surface proteins with, for instance, DNA-tagged antibodies, single cells are embedded in hydrogel droplets. Not being bound by a theory, the hydrogel mesh provides a physical framework, chemically incorporates biomolecules and is permeable to macromolecules such as antibodies (Chung, K., Wallace, J., et al., "Structural and Molecular Interrogation of Intact Biological Systems" (2013) Nature, 497, 332-337). In one embodiment, to further improve permeability and staining efficiency, lipids are cleared (Chung, K., Wallace, J., et al., "Structural and Molecular Interrogation of Intact Biological Systems" (2013) Nature, 497, 332-337). Not being bound by a theory, the clearance of the lipids and the porosity of the hydrogel allow for more efficient washing and removal of unspecific antibodies. This higher accuracy of measurement is important for the high multiplex measurements and computational inference of regulatory mechanisms.

Figure 1A:
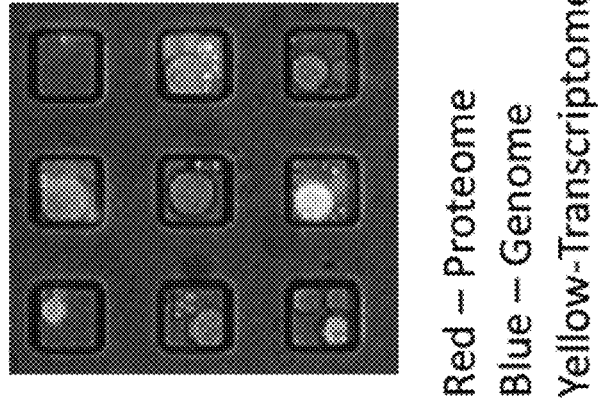
FIGS. 1A-1B illustrate a schematic of the technique for massively parallel capture of matched transcriptome, proteome and genome of single cells. A) Treated arrays of nanoliter-scale wells are pre-loaded with affinity resins specific for mRNA (barcoded-poly(dT) beads), protein (NHS-activated or aldehyde-activated agarose beads) and genome (weak anionic exchange resin). Cells are then loaded and the array is sealed with an ultrafiltration membrane. Successive buffer exchanges are then performed to lyse the cells and then activate separately each affinity resin to capture its intended target, primarily through changes in the ionic strength and pH of the buffer. Once captured, the membrane is removed and the mRNA reverse transcribed to cDNA. The protein can be queried through iterative fluorescent staining using antibodies or stained with DNA-barcoded antibodies which are subsequently transferred to the barcoded poly(dT) bead to add a cell barcode to the antibody barcode tag. Both cDNA and antibody tags are then sequenced in bulk. The genome can be recovered by micromanipulation or amplified in the nanowell using PCR or WGA. B) Exemplar image of nanoliter scale wells in which DNA (blue), mRNA (yellow) and protein (red) have been captured on separate surfaces.
Figure 1B:
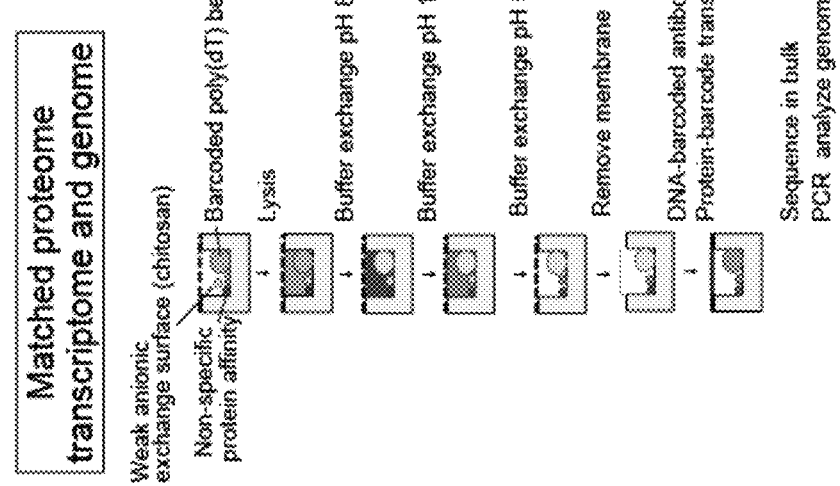
Figure 2A:
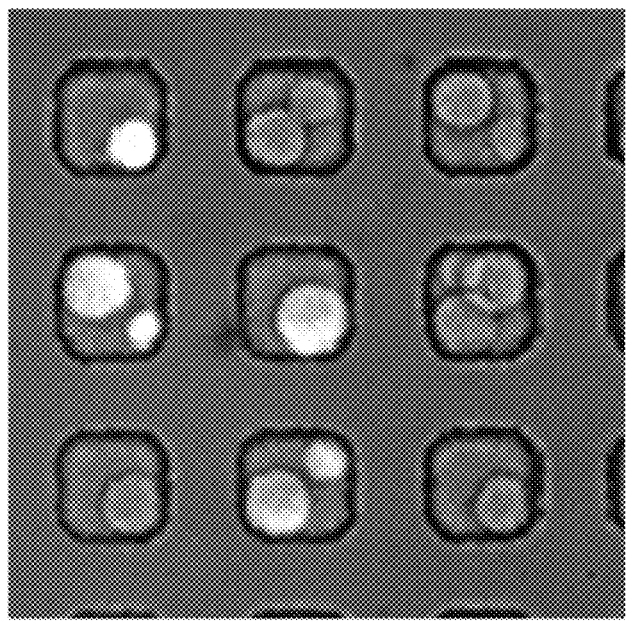
FIGS. 2A-2B illustrate massively parallel capture and reverse transcription of mRNA from cells in nanoliter-scale wells. A) Poly-dT-coated agarose beads were co-loaded with PBMC stained with calcein, sealed in with ultrafiltration membrane and imaged for calcein signal. B) Cells were lysed by buffer exchange with lysis buffer and transcript was then captured by buffer exchanging with hybridization buffer. The membrane was then removed and transcript was reverse transcribed using a reaction mix doped with BrdUTP. Incorporated BrdU was visualized by digesting mRNA with RNAseH and staining with αBrdU-PE antibody.
Figure 2B:
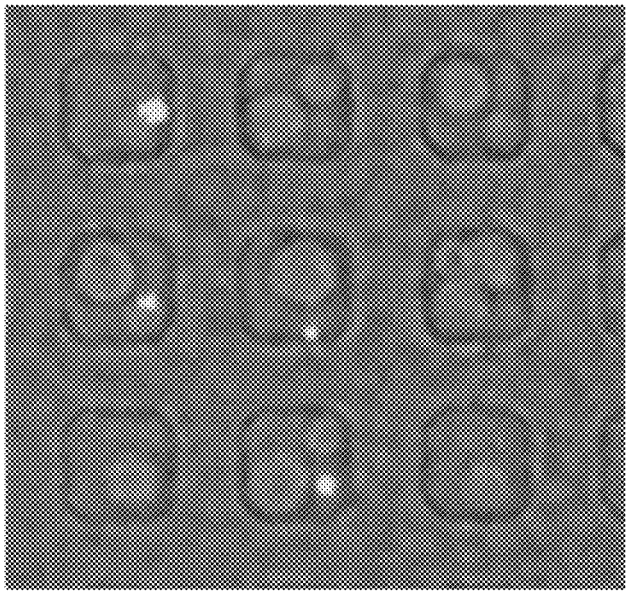
Figure 3:
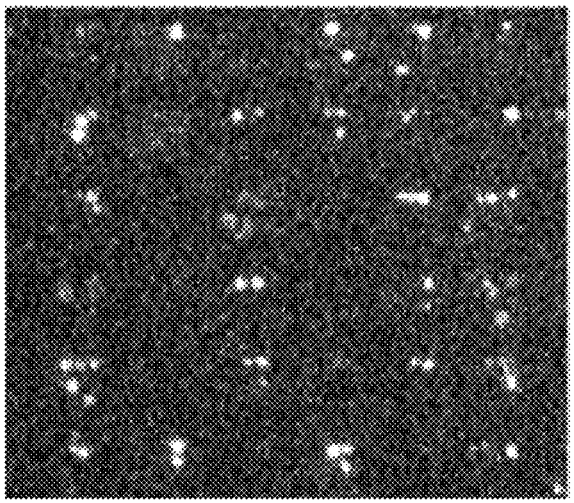
FIG. 3 illustrates massively parallel capture of protein from cells in nanowell. A) Glyoxal functionalized agarose beads and PBMC labeled with αCD45-AF647 antibody were co-loaded into functionalized nanoliter scale wells, sealed in with ultrafiltration membrane and imaged for AF647 signal. B) Cells were lysed by buffer exchanging with GuTCN+sarkosyl lysis buffer and then imaged for AF647 signal. C) Protein was then induced to covalently bind to glyoxal resin by raising pH to pH 10 for 1 hr and then arrays were imaged for AF647 signal.
Figure 3:
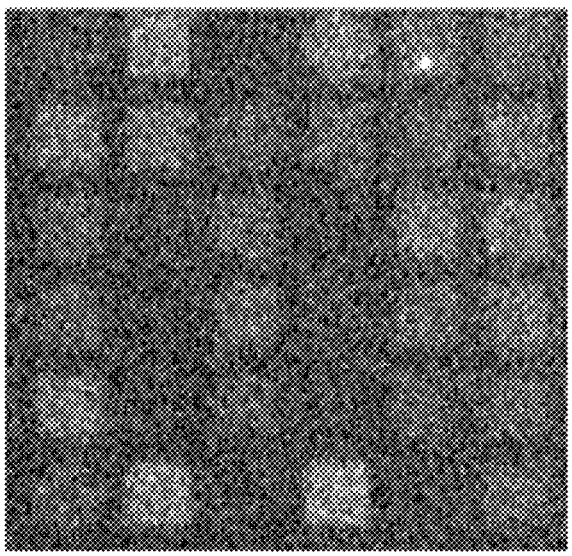
Figure 3:
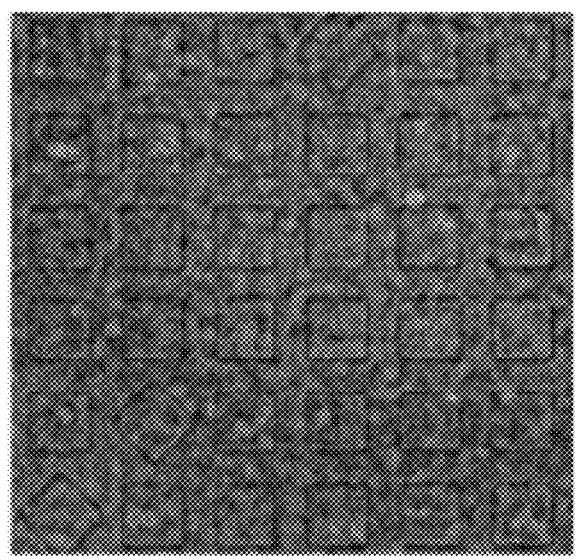
Figure 4:
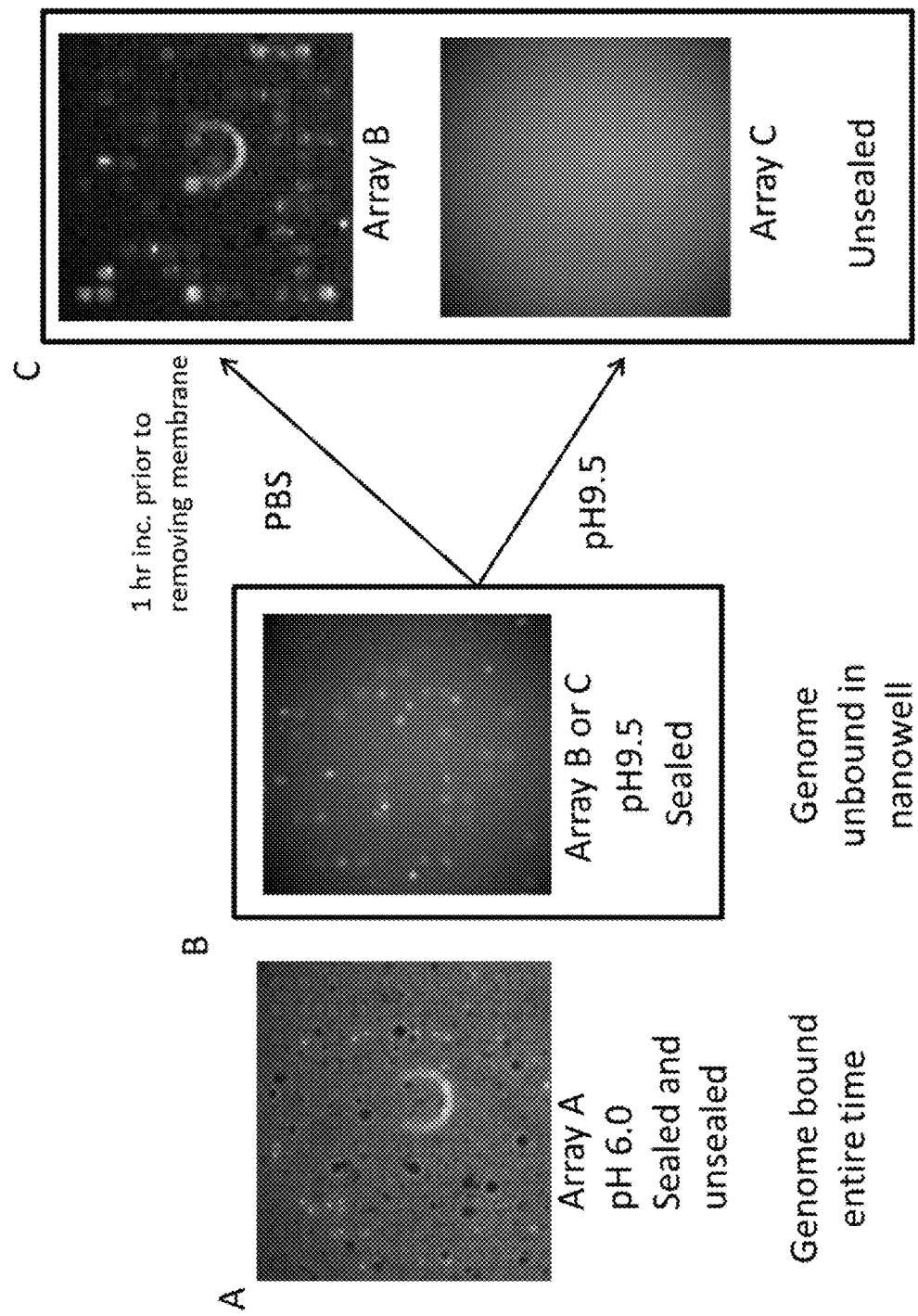
FIG. 4 illustrates massively parallel capture of genomes from cells in nanoliter scale wells. PBMC were loaded into three nanowell devices functionalized with chitosan on top surface and inner well surface. Cells were sealed in using ultrafiltration membrane, lysed through buffer exchange with GuTCN+sarkosyl for 1 hr, and then buffer exchanged with hybridization buffer at pH 6 (Array A) or pH 9.5 (Array B and C) containing Sytox Green to stain the genome for 1 hr. Arrays were imaged for Sytox signal. Array B was buffer exchanged with a hybridization buffer at pH 7.4 for 1 hour. The membranes were removed and arrays imaged again for Sytox signal. A is an exemplar image of Array A before or after membrane removal—genome remains bound to surface in punctate form where cell originally sat. B is an exemplar image Arrays B or C while still sealed with membrane—genome diffuse through well indicating free diffusion. C is an exemplar images of Arrays B and C after membrane removal. Genome remains bound in array buffer exchanged with pH 7.4 buffer while genomes are lost from arrays kept in pH 9 buffer.

The hydrogel mesh provides a physical framework, chemically incorporates biomolecules and is permeable to macromolecules such as antibodies (Chung, K., Wallace, J., et al., "Structural and Molecular Interrogation of Intact Biological Systems" (2013) Nature, 497, 332-337). Lipids are cleared as described (Chung, K., Wallace, J., et al., "Structural and Molecular Interrogation of Intact Biological Systems" (2013) Nature, 497, 332-337). FIGS. 2 A and B show hydrogel embedded cells that have been fluorescently stained for genomic DNA, the intracellular protein PCNA, and surface marker CD51. In addition, applicants are able to detect protein levels present in the hydrogel encapsulated cell as shown FIG. 2C, where a GFP KI cell line was stained with an Alexa647 anti-GFP antibody, and a spearman correlation of 0.98 is observed by FACS measurement, whereas a BD Cytofix/perm protocol led to a correlation of 0.36. This shows that clearance of the lipids and the porosity of the hydrogel allow for more efficient washing and removal of unspecific antibodies. This higher accuracy of measurement is especially crucial in a high multiplex measurements and computational inference of regulatory mechanisms.

Optical Plastic Devices

Device construction will not be limited to soft lithography in PDMS or other elastomeric polymers. Construction of nanowell devices in optical plastic including poly(methyl methacrylate) (PMMA), cyclic olefin co-polymer (COC), polyvinyl, polystyrene, and polypropylene is possible using hot embossing or 3D printing technologies. Consistent membrane attachment via covalent linkage relies on close and uniform contact between reactive moieties on the surface of the device and membrane. Minor deformability of elastomeric materials facilitates efficient attachment of polycarbonate membranes to the surface of PDMS arrays to form a seal. Minimal elasticity and minor imperfections in the surface of optical plastic devices might interfere with efficient attachment of polycarbonate membranes to the surface of hot embossed devices.

Membrane attachment and nanowell sealing for optical plastic devices will, therefore, rely on materials with a relatively high degree of elasticity capable of forming a uniform seal. By varying the deformability of membrane substrates, Applicants can achieve the desired range of size selectivity while maintaining efficient sealing. Options include the use of PDMS membranes and woven fiber membranes.

3D printing could be used to selectively print layered devices using different plastics with different surface functionalizations, namely, to reduce surface adsorption of biomolecules of interest within nanowells while optimizing membrane attachment to the surface of the device. For example, 3D printing with low-retention surfactant-coated polymers (mention is made of U.S. Pat. No. 6,319,664) could be followed by printing and/or functionalization of the surface for membrane attachment. Other methods for synthesis of low-retention polymers involve doping surfactants into polymers through melting and mixing that are then suitable for injection molding or 3D printing (mention is made of European Patent 1464677). Importantly, it would be possible to print a combination of polymers on the same device, whereby polymers optimal for the membrane attachment could be printed on the surface device, while polymers ideally suited for cell culture, RNA capture, protein isolation, etc. could be used to form the bulk of the nanoliter scale wells.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Generalized Protocol

Array Functionalization

Figure 5:
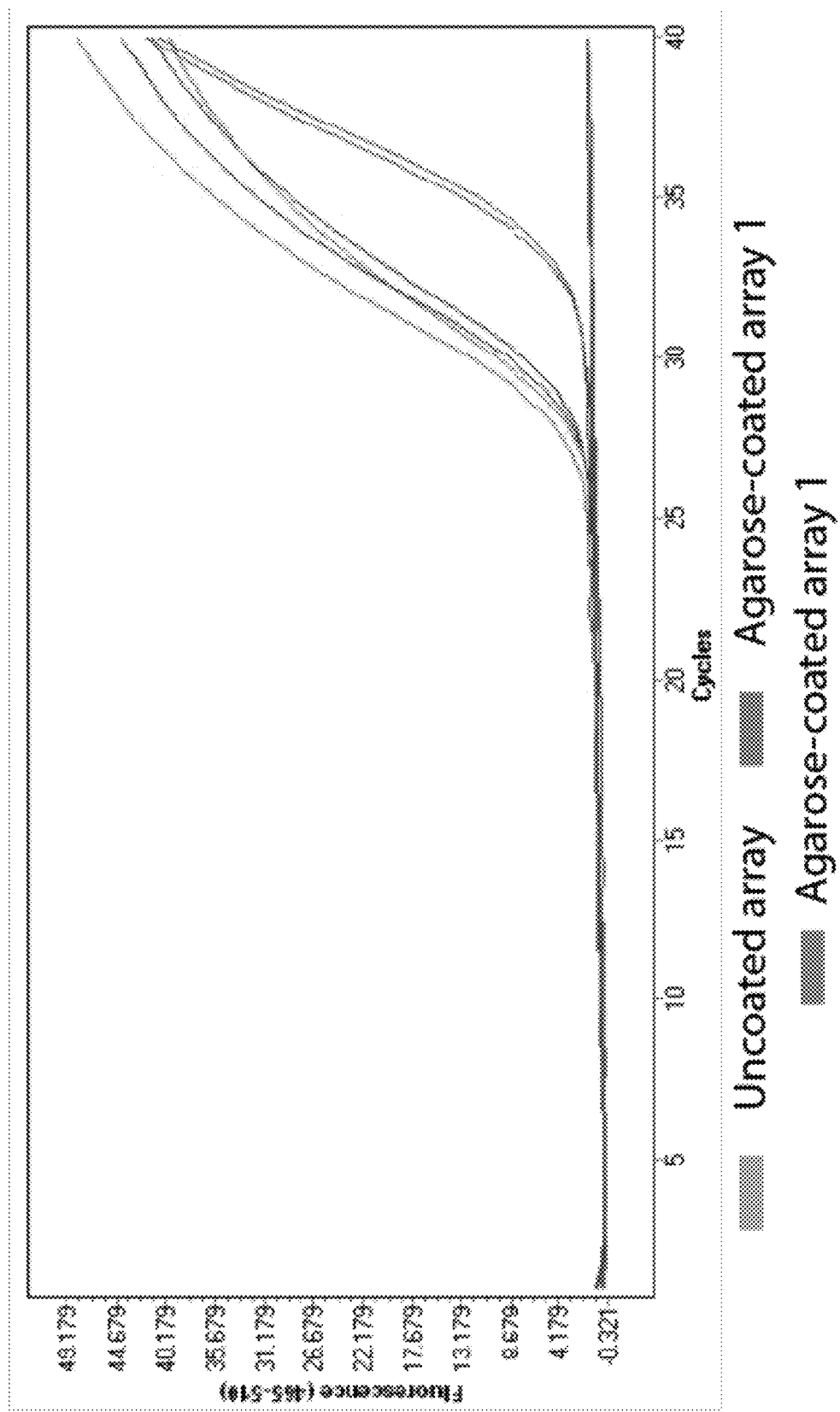
FIG. 5 illustrates agarose coating of arrays improves transcript capture. Top surfaces of 3 nanowell arrays were functionalized with chitosan and wells were functionalized with poly(glutamate) using typical procedure. Two of the arrays were then further functionalized with a thin film agarose hydrogel only on the inner well surfaces. Nanowell arrays were then used to capture and reverse transcribe mRNA from single cells. Beads were collected from array and technical replicates of 1000 beads were used in a qPCR reaction measuring the number of GAPDH cDNA molecules. Amplification curves for untreated (blue) and the two agarose treated arrays (red and green) are displayed.
Figure 6:
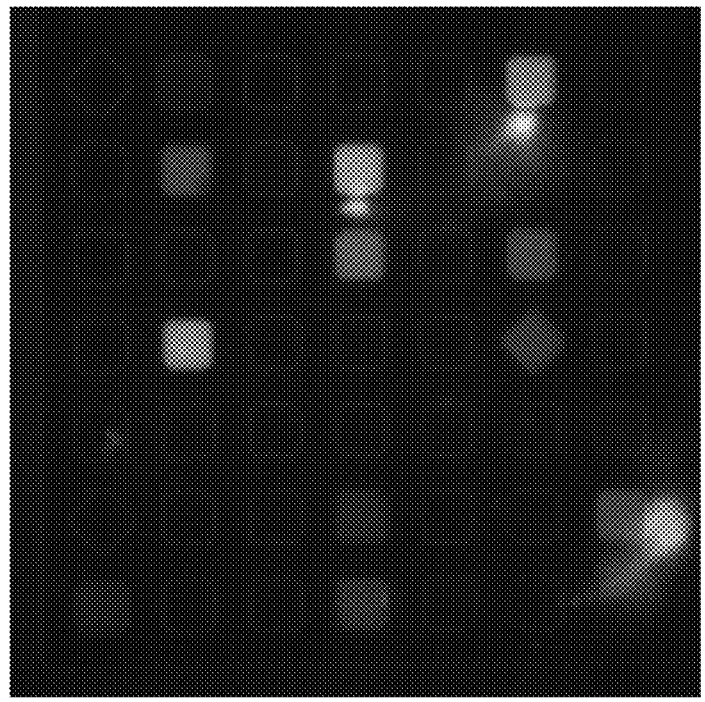
FIG. 6 illustrates WGA in membrane-covered nanoliter scale wells.
Figure 7:
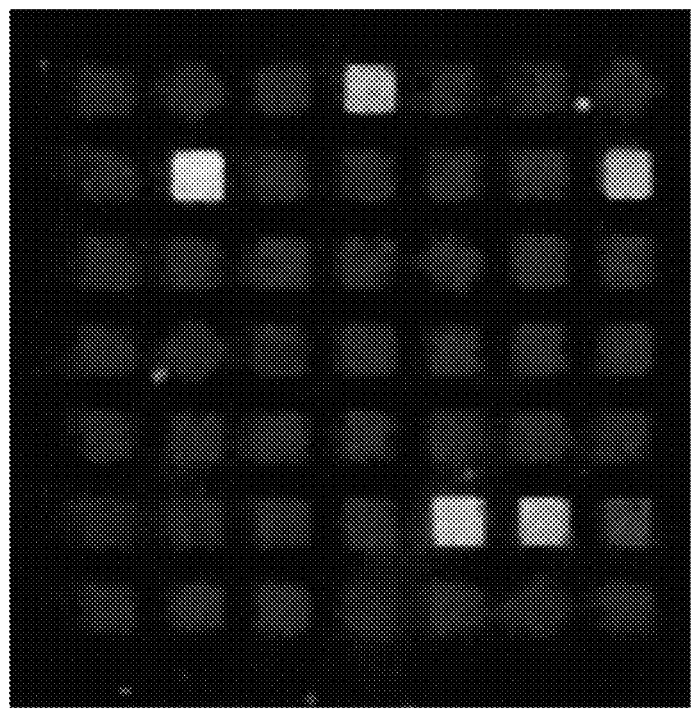
FIG. 7 illustrates microengraving through the membrane.
Figure 8:
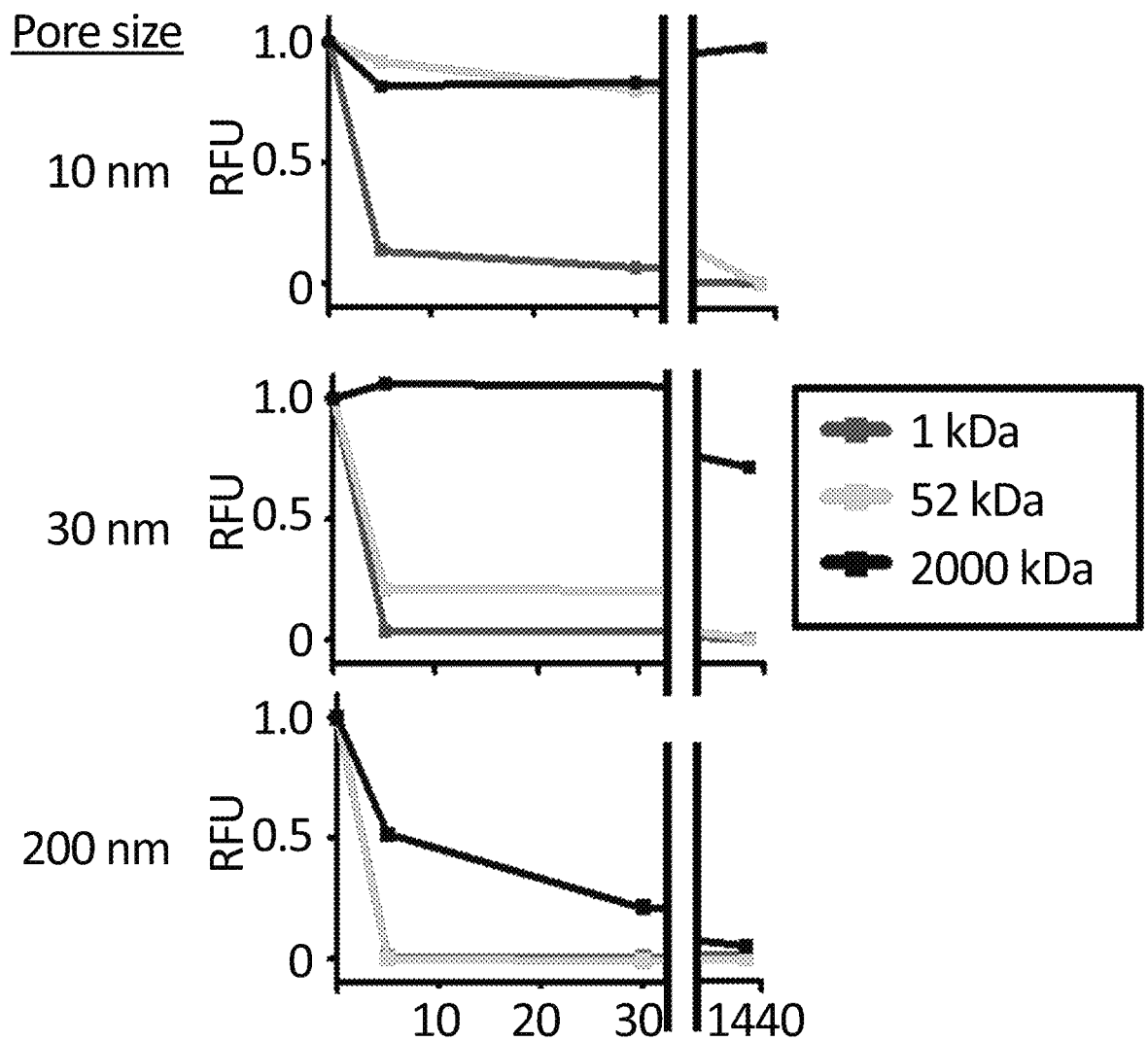
FIG. 8 illustrates the effect of pore size on analyte diffusion from cells.

Procedure for massively parallel capture from single cells of transcript, protein or genomic content or any combination thereof begins by functionalizing a surface of an array material, for example, the top PDMS surface of the arrays with a poly-amine to enable robust membrane attachment in aqueous solutions. Chitosan is the preferred polyamine as its charge can be more easily manipulated by pH but poly (lysine) also works. This can be done by nonspecific absorption of the polymers to the surface but if robust denaturing lysis buffers are to be used, covalent linking of the polymer to the surface is required to maintain sealing. This is achieved by first covalently linking an amine silane to the surface through typical silane chemistry, followed by cross-linking of the amine layer with a homo-bifunctional amine crosslinker, preferably phenylene diisothiocyanate. The second half of the crosslinker is then used to covalently attach the amine polymer to the top surface. This can be done specifically to only the top surface by utilizing the hydrophobicity of the surface and the small area of the wells, namely PDITC functionalized arrays submerged in aqueous solutions do not hydrate the wells over many hours so only the top surface is exposed to the polyamine for functionalization. After top surface treatment, the wells can be functionalized with any number of molecules containing an amine, preferably Tris (creates more hydrophilic, neutral surface) or poly(glutamate) to create a negative surface to repel mRNA from the PDMS surface, enabling more to be specifically bound by the poly(dT) bead. Finally, Applicants have demonstrated that covering of the PDMS surface within the well with an agarose hydrogel further decreased nonspecific binding of mRNA to the PDMS surface. (FIG. 5). This required developing special protocols to achieve because it is critical that the agarose does not coat the top surface as this prevents efficient binding of the membrane to the surface. Array functionalization can be done in batches of 25 or more and once functionalized, the arrays have been demonstrated to be stabile for at least one week stored at 4° C.

Macromolecule Capture

Macromolecular capture is accomplished by co-loading cells of interest and affinity resin for the molecule of interest into functionalized arrays. The preferred resin for mRNA is barcoded, poly(dT) beads, for protein is base-activated resins such as NHS or glyoxal activated agarose beads and for genome is weak anionic exchange resins. When multiple macromolecular capture is desired, it is critical that the resins are specific to their intended target which is accomplished either by the specificity of the resin or the sequence in which the resins are activated for binding—i.e, anionic exchange resin when active will bind both DNA and RNA and some protein when active at low pH and low ionic strength, but can be held in the well in an inactive form by high pH buffer while RNA and protein bind their respective resins. Typically, the affinity resins are loaded into the nanowell array first due to buffer requirements for efficient resin loading (low pH for protein resin and high pH for poly(dT) beads) that are toxic to cells. Once the desired combination of resins is loaded, buffer is switched to tissue culture media and cells are loaded. The nanoliter scale wells are then sealed using a track-etched polycarbonate ultrafiltration membrane using a clamp. After 30 min the clamp is removed. In normal tissue media, wells can remain sealed for >24 hours retaining any macromolecule within the volume of the nanowell while allowing exchange of small molecules from bulk solutions in which the sealed array is submerged. Crucially, the buffers can be easily changed, enabling control over the reaction conditions within the sealed nanoliter scale wells. The sealed array goes through a series of buffer exchanges and hybridizations depending on the identity and number of macromolecules that are to be captured. Once all molecules are secured to a surface, the membrane is peeled off the array. Typically, reverse transcription is the first step performed after membrane removal as mRNA is the most labile of the macromolecules. Protein is the next to be analyzed which can be accomplished directly with fluorescent antibodies. Applicants envision ultimately using DNA-barcoded antibodies to label proteins and post transcriptional modifications. The protein DNA barcodes will be released from the antibody, captured on the barcoded poly(dT) bead and reading out protein content with sequencing using the bead barcode to match it to the transcript but this has not been fully implemented yet. Captured genomic content can be queried through on array PCR, amplified on array use WGA or recovered through micromanipulation for bulk processes.

Seq-Well

Figure 9:
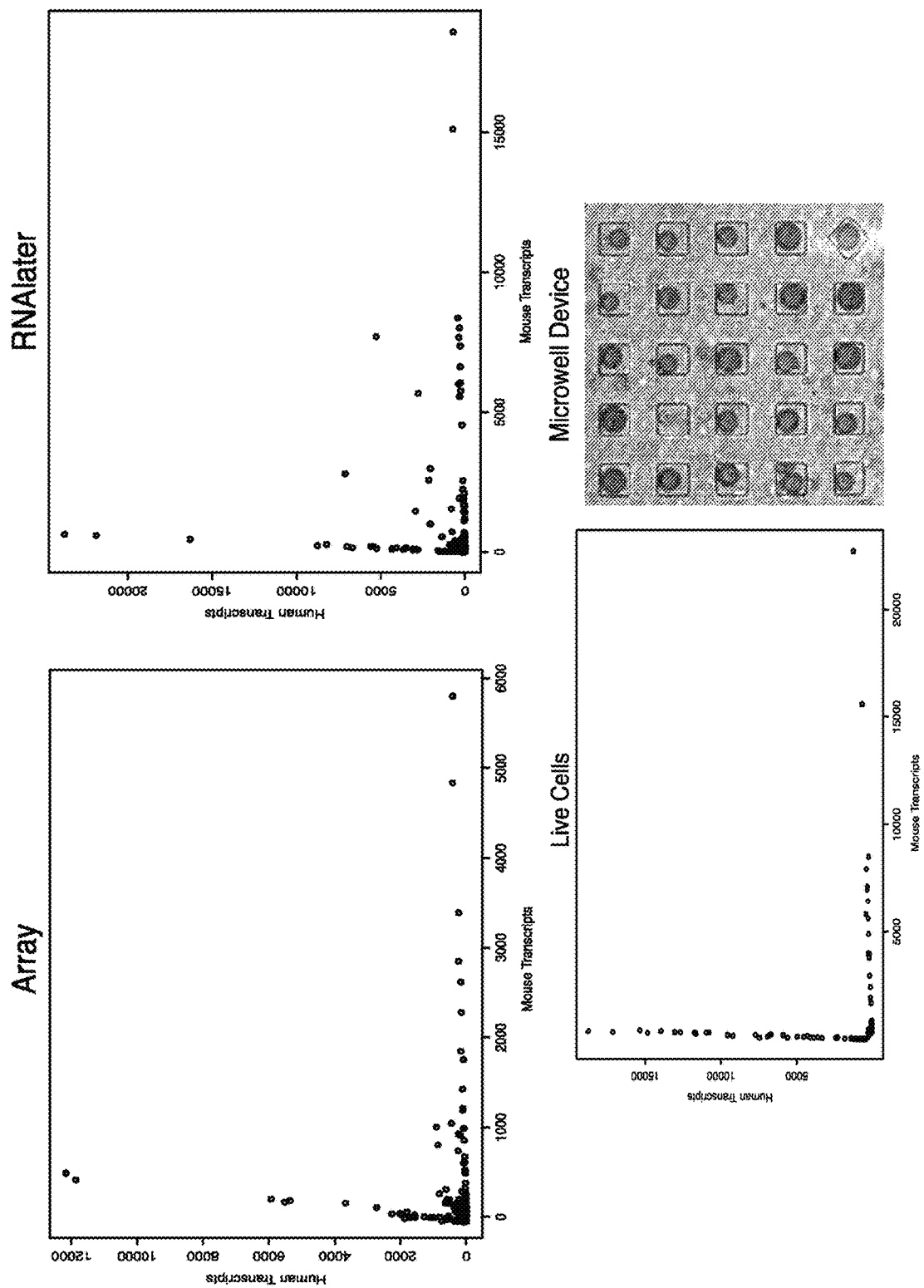
FIG. 9 illustrates the Seq-Well clearly separates a mixture of mouse and human cells. Each unique cell barcode only aligns to one of the two species, proving that each barcode distinguishes a single cell. Reverse transcription or other molecular processing can be performed on the array ('array') or off of the array ('live cells') after cellular isolation, lyse, and affinity capture. Fixed cells can also be run on the array and cells can be fixed on the array prior to running ('RNAlater').

Once all desired analysis of macromolecules on the array has been completed, the barcoded beads can be recovered from the array through centrifugation or scraping them off the surface. The barcoded cDNA can undergo whole transcriptome amplification and then be sequenced in bulk. Each sequencing read can be traced back to a single cell using the bead barcode attached to each transcript during the RT reaching identical to published protocols such as DropSeq (FIG. 9, "live cells"). In other instances, reverse transcription can be performed on the array (FIG. 9, "array").

Bead Synthesis

Barcoded oligo-dT beads (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214) were purchased from Chemgenes (Wilmington, MA, USA; Cat. #MACOSKO-2011-10) at 10 umol scale (~100 arrays). Bead functionalization and reverse phosphoramidite synthesis was performed by Chemgenes Corporation using Toyopearl HW-65S resin (30 micron mean particle diameter) obtained from Tosoh Biosciences (Cat. #19815). Surface hydroxyls were reacted with a PEG derivative to obtain an 18-carbon linker to serve as a support for oligo synthesis. Reverse-direction phosphoramidite synthesis was performed using an Expedite 8909 DNA/RNA synthesizer at 10 micromole scale with a coupling time of 3 minutes. Initially, a conserved PCR handle was synthesized followed twelve rounds of split and pool synthesis to generate 16,777,216 unique barcode sequences. Addition of an 8-mer random sequence was performed to generate unique molecular identifiers (UMIs) on each capture oligo. Finally, a 30-mer poly-dT capture sequence was synthesized to enable capture of polyadenylated mRNA species.

Imaging Differential Surface Functionalization

Differential labeling of the top and inner well surfaces was visualized by substituting 1 µg/mL PE-Streptavidin for chitosan (step 8, Seq-Well Protocol and 1 µg/mL AlexaFluor488-Streptavidin for the poly-glutamate (step 10, Seq-Well Protocol) in the standard functionalization protocol (FIG. 15). Carboxylation of the inner well surfaces was visualized by treating the functionalized array with 100 µg/mL EDC/10 µg/mL NHS MES (pH 6.0) solution for 10 min, washing twice with MES buffer, once with sodium borate buffer (pH 8.5), and incubating overnight with 1 µg/mL Alexa-Fluor 568-labeled antibody. Arrays were washed three times with phosphate buffered saline (PBS) and imaged using Alexa Fluor 568 channel.

Visualizing Lysate Retention (Imaging)

PBMCs were labeled with αCD45-AF647. Cells were washed and loaded onto two arrays previously blocked with 1% BSA solution for 30 min and one array functionalized with chitosan as described above. A polycarbonate membrane was attached to the chitosan-functionalized array as described above. The array was submerged in PBS and imaged for AF647 fluorescence to identify wells containing cells. The BSA-blocked arrays were imaged prior to membrane attachment because the membrane would detach when submerged in media. After imaging, a plasma-treated polycarbonate membrane was attached to one of the BSA-blocked arrays as described (Dekoskey, B. J., et al., "High-throughput sequencing of the paired human immunoglobulin heavy and light chain repertoire" (2013) Nature Biotechnology 31, 166-169). Briefly, the membrane was placed on the array with forceps and all excess media was aspirated from the array. The open BSA-blocked array and the chitosan array were submerged in 5 mL of 5 M GCTN lysis buffer. 500 µL of lysis buffer was placed on the top of membrane attached to the BSA-blocked array as described (Dekoskey, B. J., et al., "High-throughput sequencing of the paired human immunoglobulin heavy and light chain repertoire" (2013) Nature Biotechnology 31, 166-169). Five and thirty minutes later, 100 block positions were imaged on each array, encompassing 12,100 individual wells. Automated image analysis software was used to background subtract each image, identify cell and well locations and extract AF647 signal intensity of the cells and the well volumes (FIG. 16).

Calculating Bead Loading Efficiency

Figures 13A, 13B:
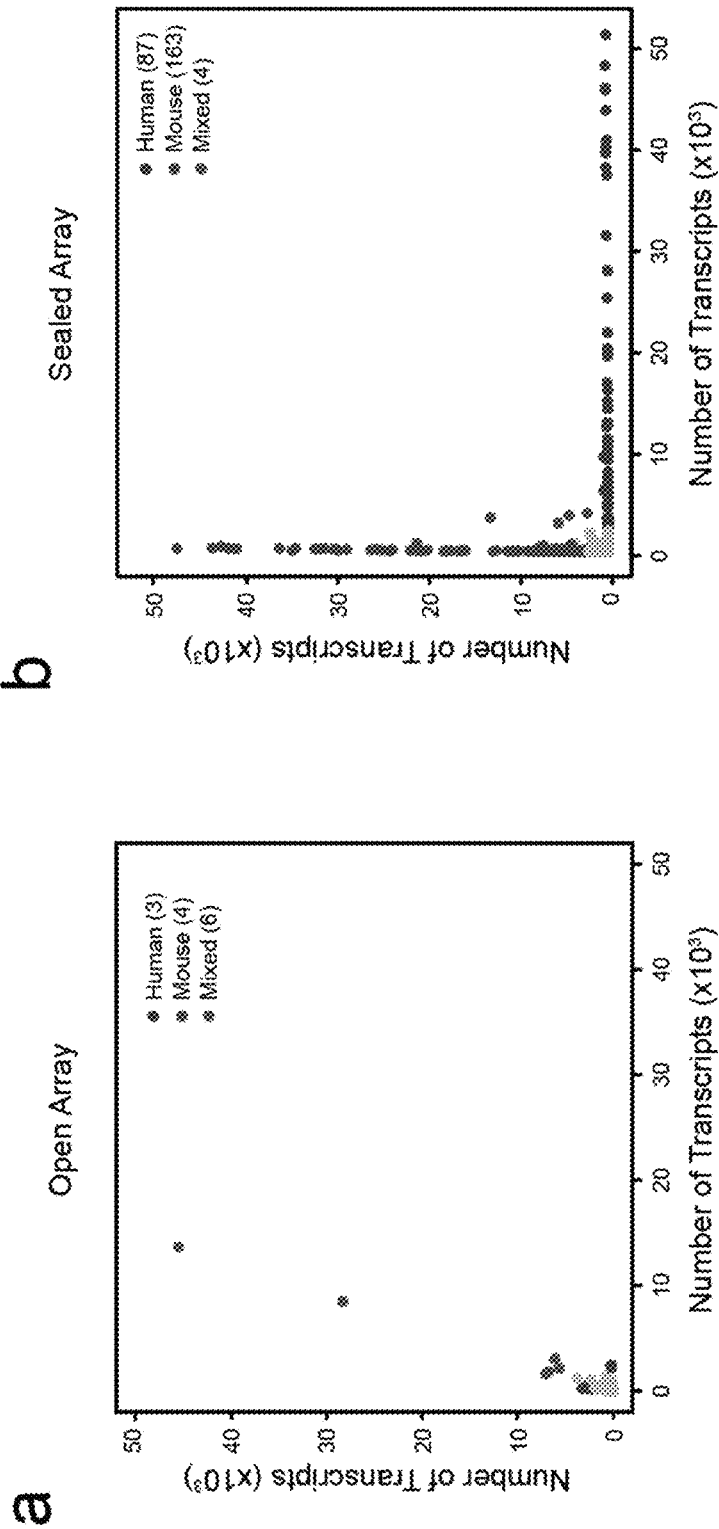
FIGS. 13A-13B illustrates open array gene and transcript capture. (A) An open array format results in decreased gene and transcript capture, and increased cross-contamination, relative to the membrane sealing implemented in Seq-Well. (B) Species mixing experiments with reversible membrane sealing using Seq-Well provides increased gene/transcript capture and improved single-cell resolution.
Figure 14:
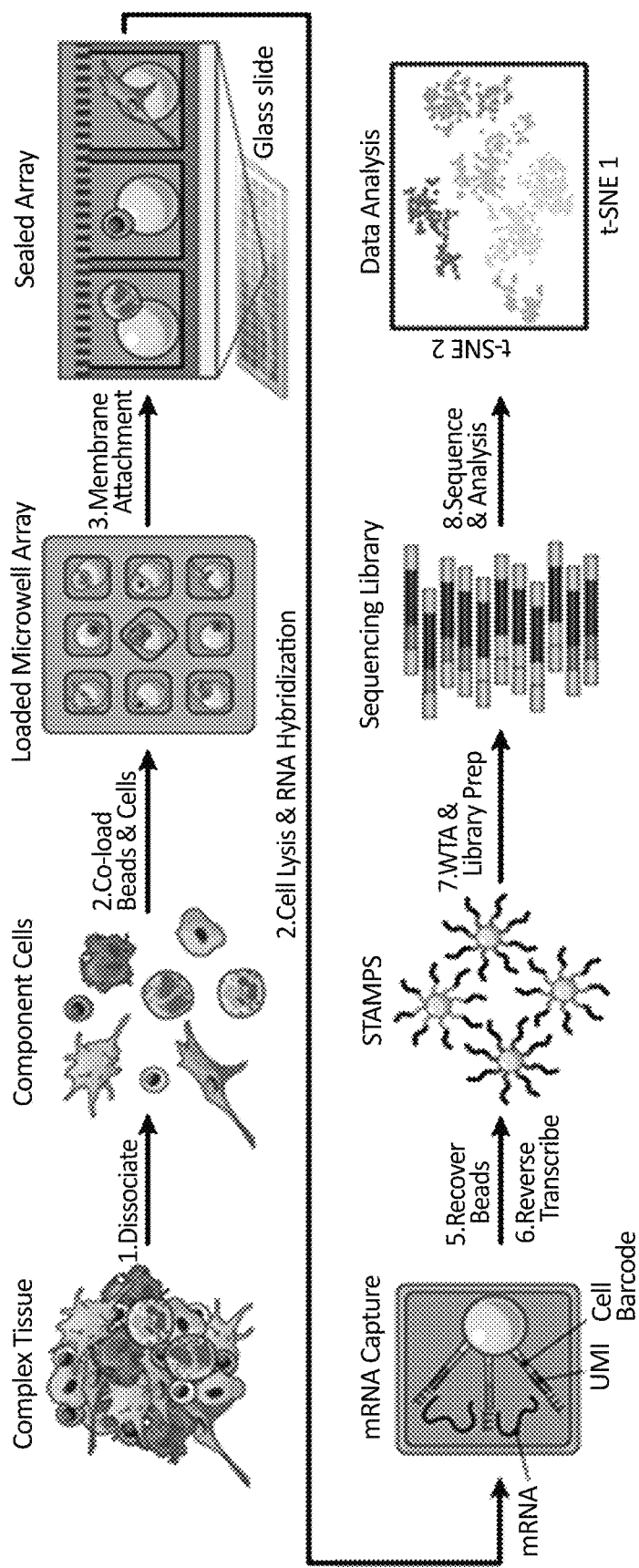
FIG. 14 illustrates Seq-Well experimental workflow. Cells are obtained from complex tissues or clinical biopsies, and digested to form a single-cell suspension. Barcoded mRNA capture beads are added to the surface of the microwell device, settling into wells by gravity, and then a single-cell suspension is applied. The device is sealed using a semipermeable membrane that, upon addition of a chemical lysis buffer, confines cellular mRNAs within wells while allowing efficient buffer exchange. Liberated cellular transcripts hybridize to the bead-bound barcoded poly(dT) primers that contain a cell barcode (shared by all probes on the same bead but different between beads) and a unique molecular identifier (UMI) for each transcript molecule. After hybridization, the beads are removed from the array and bulk reverse transcription is performed to generate single-cell cDNAs attached to beads. Libraries are then made by a combination of PCR and tagmentation, and sequenced. After, Single-cell transcriptomes are assembled in silico using cell barcodes and UMIs.

Bead loading efficiencies were determined by loading two functionalized arrays with beads as outlined above (FIG. 13). Arrays were imaged in transmitted light and AF488 channel to capture bead autofluorescence. Automated image analysis was used to identify well locations and extract the $75^{th}$ percentile fluorescence intensity in each well. Histogram analysis of fluorescence intensities was used to identify empty wells and wells containing beads. Finally, manual review of 50 randomly selected image positions, each containing 121 nanowells, of a total of 690 positions was used to calculate the frequency of wells containing two beads.

Calculating Cell Loading Efficiency

To calculate cell loading efficiencies and well occupancy distributions (FIG. 15), HEK293 and 3T3 cells were labeled with Calcein AM (Life Technologies) and Calcein Violet (Life Technologies), respectively, per the manufacturer's recommendations. 200 µL of serial dilutions of a 1:1 mix of the cells at an estimated concentration of 1,000, 10,000 and 100,000 cells/mL were loaded in functionalized arrays in triplicate using the standard protocol. To determine the distribution of cells present in 200 µL of these solutions, the same volume of each solution was added to 12 wells each of a 96 well plate. 690 array positions on each array were imaged in the transmitted light, AF488 and AF405 spectral channels. Overlapping images of each well of the 96-well plate were acquired in the same channels. Automated image analysis was used to identify well and cell locations in the array images. The overlapping images of the 96-well plate were stitched together based on x-y location of each image and analyzed in a similar manner to identify cell locations. All three dilutions were used to determine the distribution of well occupancy as a function of the number of cells loaded. The 10,000 cells/mL dilution were used to calculate cell loading efficiency.

Species Mixing Experiments

Murine NIH/3T3 cells (ATCC, CRL-1658) were cultured in Dulbecco's modified eagle medium (DMEM) with glutamate and supplemented with 10% fetal calf serum (FCS) at 37° C. and 5% CO2. Human 293T cells (ATCC, CRL-11268) were cultured at 37° C. and 5% $CO_2$ in DMEM with glutamate supplemented with 10% fetal bovine serum (FBS). The media was removed from the culture flasks, which were then rinsed with 5 mL of 1×PBS. Cells were detached from the surface of the culture flasks by applying 3.5 mL of Trypsin-LE (Life Technologies) and incubating at room temperature for 5 minutes. Once cells had de-adhered, 10 mL of complete media was added, and cells were pelleted by spinning at 500 G for 10 minutes. Cell pellets were resuspended in 1 mL of media and a 10 µL aliquot was used to count cells. A total of 100,000 HEK and 3T3 cells were again pelleted and resuspended in 1 mL of media. For species mixing experiments, a total of 200 µL of a single-cell suspension containing 5,000 HEK and 5,000 NIH/3T3 cells was applied to the surface of two nanowell devices loaded with beads. In the first experiment, of the 60,000 beads collected from the array, 9,600 beads were pooled for subsequent processing and sequencing, from which Applicants identified 254 high-quality cells with greater than 2,000 transcripts. In the second experiment, of the 25,000 beads collected from the array, 15,000 beads were pooled for subsequent processing and sequencing, from which Applicants identified 331 high-quality cells with greater than 10,000 transcripts, greater than 2,000 genes, and greater than 90% transcript purity (i.e. >90% of transcripts from the same species). Also, as in Drop-Seq, Applicants attempted to validate capture efficiency using ERCC spike-ins; however, this required us to load ERCCs onto the nanowell array by pipetting, which proved inefficient to properly assess capture efficiency since Applicants could not evenly distribute ERCCs to nanowells.

HEK Population Experiments

Figure 21:
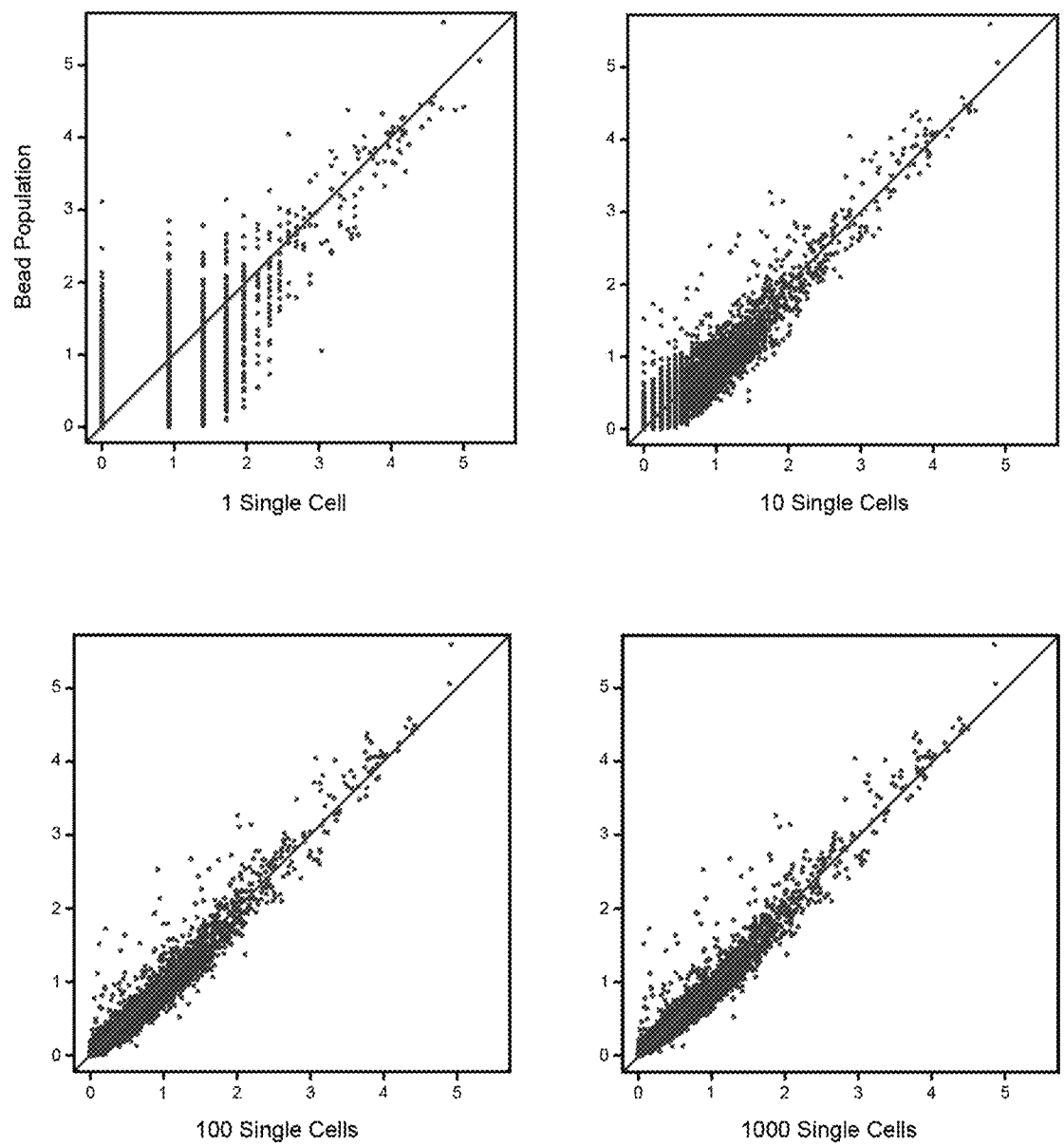
FIG. 21 illustrates a comparison of in-silico HEK293 populations with bulk populations. Scatterplots showing the correlation between gene expression estimates from bulk populations (40,000 HEK cells and 40,000 mRNA capture) and populations generated in-silico from 1, 10, 100, and 1,000 randomly-sampled single HEK293 cells (1 Cell.
Figures 22A, 22B, 22C, 22D, 22E, 22F, 22G, 22H, 22I:
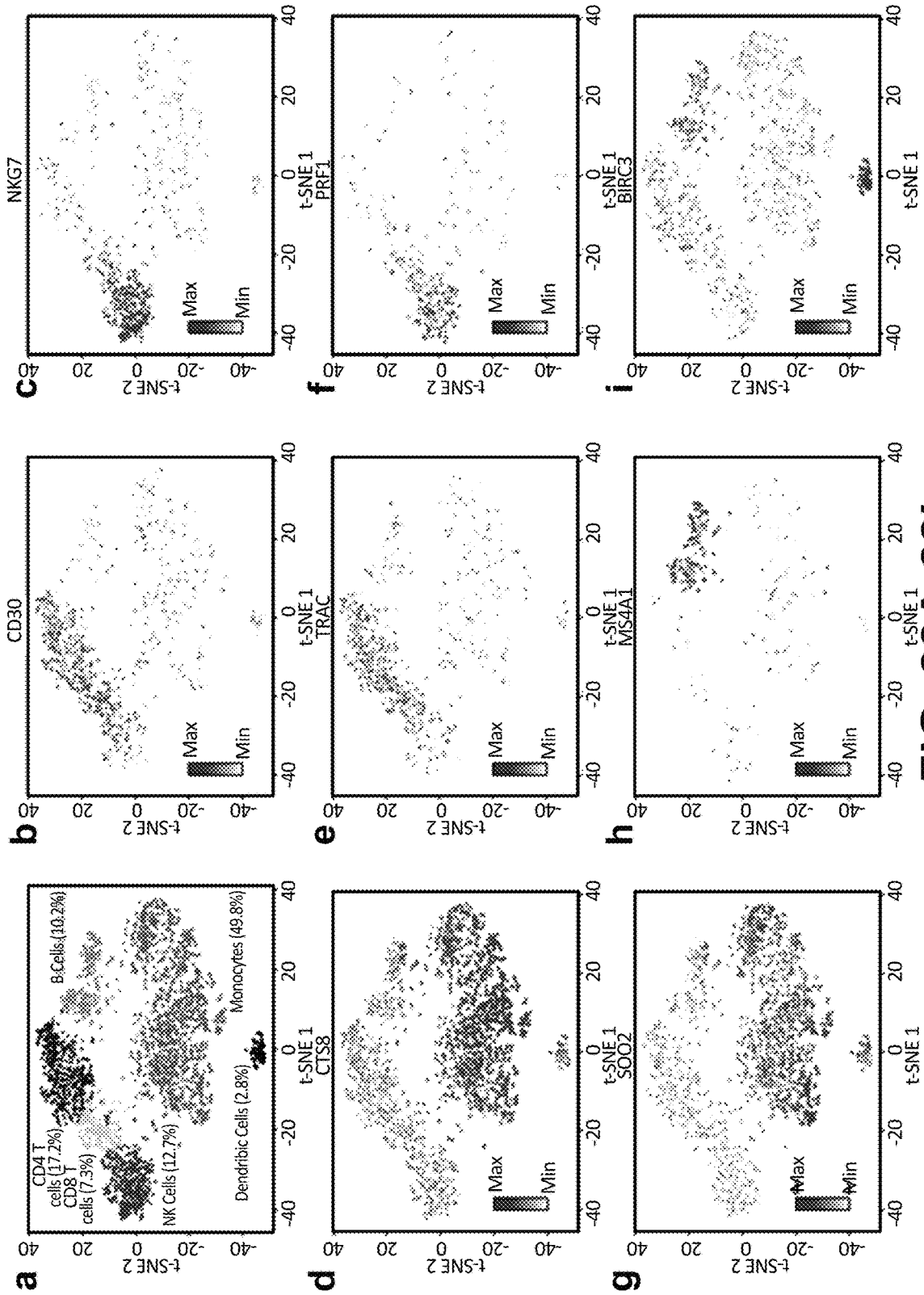

HEK293 cells were cultured in RPMI supplemented with 10% FBS. A total of 10,000 HEK293 cells were applied to a Seq-Well device and scRNA-Seq libraries were generated from 24,000 beads and sequenced on a NextSeq 500. For the bulk RNA-Seq sample, cellular lysate from 40,000 HEK293 cells in 200 µL of lysis buffer (5M GTCN, 1% 2-mercaptoethanol, 1 mM EDTA, and 0.1% Sarkosyl in 1×PBS, pH 6.0) was combined with 40,000 mRNA capture beads in a PCR tube and rotated end-over-end for 1 hour. Afterward, the beads were washed and a population sequencing library was constructed in an identical manner to the single-cell Seq-Well libraries but with reads from the different bead barcodes combined into one population. In-silico populations were created by randomly sampling 1, 10, 100 or 1000 HEK cells from a total of 1,453 cells with greater than 3,000 transcripts obtained from a Seq-Well array. Average Pearson correlation coefficients, and their standard deviation, were calculated between 100 randomly generated in-silico populations for each number of cells and the bead population (FIG. 21).

Human PBMC Experiments

Leukocytes isolated from a leukocyte reduction filter used during platelet apheresis were purchased from Key Biologics (Memphis, TN). The cells were shipped overnight at room temperature. PBMC were isolated from the sample using a Ficoll-Hypaque (GE) gradient, washed two times with HBSS buffer, and frozen in 90% FBS/10% DMSO in aliquots of $10^7$ cells. The day before the experiment, an aliquot was thawed and rested overnight in RPMI-1640 supplemented with 10% FBS, Pen/Strep, non-essential amino acids, sodium pyruvate, and HEPES buffer (RP10) at $10^6$ cells/mL in 50 mL conical tube. Cells were counted the next day, and $5 \times 10^5$ cells were pelleted, resuspended in 1 mL of CellCover solution, and processed as described above.

Array Loading for Imaging (PBMCs)

To quantify cell surface marker protein expression levels on array (FIG. 11a), PBMCs were loaded first and imaged prior to bead addition due to bead autofluorescence. Here, cells were resuspended in cold CellCover (Anacyte), an RNA stabilization reagent, and placed at 4 C for 1 hour. Cells were spun down and resuspended in a cocktail containing αCD45-AF647 (Biolegend; HI30), αCD3-PerCP (Biolegend; UCHT1), αCD4-PECy5.5 (eBioscience; SK3), αCD56-PECy5 (BD Biosciences; B159), αCD8-APCCy7 (Biolegend; RPA-T8), αHLA-DR-PECy7 (BD Biosciences; L243), and αCD19-PE (Biolegend; HIB19) in RP10 media and were incubated at 4° C. for 30 min. Cells were washed twice with PBS and resuspended in CellCover10 buffer (CellCover supplemented with 10% FBS and 100 mM sodium carbonate (pH 10) buffer). Functionalized arrays were washed with 5 mL of CellCover10 buffer. $2.0 \times 10^4$ cells were loaded onto the array and washed twice with CellCover10 buffer and finally the array was placed in 5 mL CellCover. Arrays were imaged with a Zeiss AxioVision microscope with Lumencor light source and EMCCD camera using the settings described herein. Automated imaging software was used to identify cell locations within the images and extract signal intensities in each spectral channel. To generate spillover coefficients for each fluorophore, α-mouse beads (Bangs Labs) were stained individually with each antibody using the same protocol as the cells. Images of the singly stained beads were used to generate spillover coefficients for each fluorophore that were then used to calculate the amount of each fluorophore on each cell as previously described (Roederer, M. "Compensation in flow cytometry" (2002) Current protocols in cytometry. Chapter 1, Unit 114). After imaging, arrays were washed with 5 mL CellCover10 media. Barcoded beads suspended in CellCover10 media were loaded into the array through gentle agitation. Arrays were washed 3× with CellCover10 without FBS and finally washed with CellCover. Arrays were then moved on to membrane attachment.

Human Monocyte Isolation

Primary human monocytes were isolated from deidentified human buffy coats obtained from the Massachusetts General Hospital Blood Bank using a standard Ficoll gradient and subsequent CD14 positive selection (Stemcell Technologies). Enriched monocytes were cultured in lowadherence flasks (Corning) for 9 days with RPMI media (Invitrogen) supplemented with 10% heat inactivated FCS (Sigma Aldrich).

*Mycobacterium tuberculosis* (Mtb) Culture

*Mycobacterium tuberculosis* H37Rv expressing the E2-Crimson fluorescent protein was grown in Difco Middlebrook 7H9 media supplemented with 10% OADC, 0.2% glycerol, 0.05% Tween-80 and Hygromycin B (50 µg/mL).

Macrophage Infection and Flow Cytometry

The Mtb culture was pelleted by centrifugation and washed once with RPMI+10% FCS, sonicated briefly, and filtered through a 5 µm syringe filter. Monocyte-derived macrophages (MDM) were infected at an MOI of 10 for four hours, and then washed 3× with RPMI+10% FCS. 24 hours after infection, cells were washed briefly with 1×PBS. 10× Trypsin (Life Technologies) was added and cells were incubated briefly at 37° C. to allow for cell detachment. Detached cells were spun down and resuspended in 1×PBS supplemented with 2% FCS and 1 mM EDTA, and then passed through a mesh filter to eliminate clumps. Uninfected and infected cells were sorted by flow cytometry on an Aria IIu flow cytometer. Mtb-infected cells were identified by the presence of an E2-Crimson signal above the background autofluorescence of uninfected cells.

Transcriptome Alignment and Barcode Collapsing

Read alignment was performed as in Macosko et al., Cell, 2015 (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214). Briefly, for each NextSeq sequencing run, raw sequencing data was converted to FASTQ files using bcl2fastq2 that were demultiplexed by Nextera N700 indices corresponding to individual samples. Reads were first aligned to both HgRC19 and mm10, and individual reads were tagged according to the 12-bp barcode sequence and the 8-bp UMI contained in read 1 of each fragment. Following alignment reads were binned and collapsed onto 12-bp cell barcodes that correspond to individual beads using DropSeq tools (http://mccarrolllab.com/dropseq/). Barcodes were collapsed with a single-base error tolerance (Hamming distance=1), with additional provisions for single insertions or deletions. An identical collapsing scheme (Hamming distance=1) was then applied to unique molecular identifiers to obtain quantitative counts of individual mRNA molecules. Quality metrics are presented in FIGS. 17 & 20.

Data Normalization

Digital gene expression matrices were obtained by collapsing filtered and mapped reads by 8-bp unique molecular identifier sequence within each cell barcode. From each cell, Applicants performed library-size normalization UMI-collapsed gene expression values for each cell barcode were scaled by the total number of transcripts and multiplied by 10,000. Scaled expression data were then natural-log transformed prior to analysis using using Seurat (Satija, R., et al. "Spatial reconstruction of single-cell expression data" Nature Biotechnology (2015), 33, 495-502).

Analyzing Species-Mixing Experiments

Figure 10A:
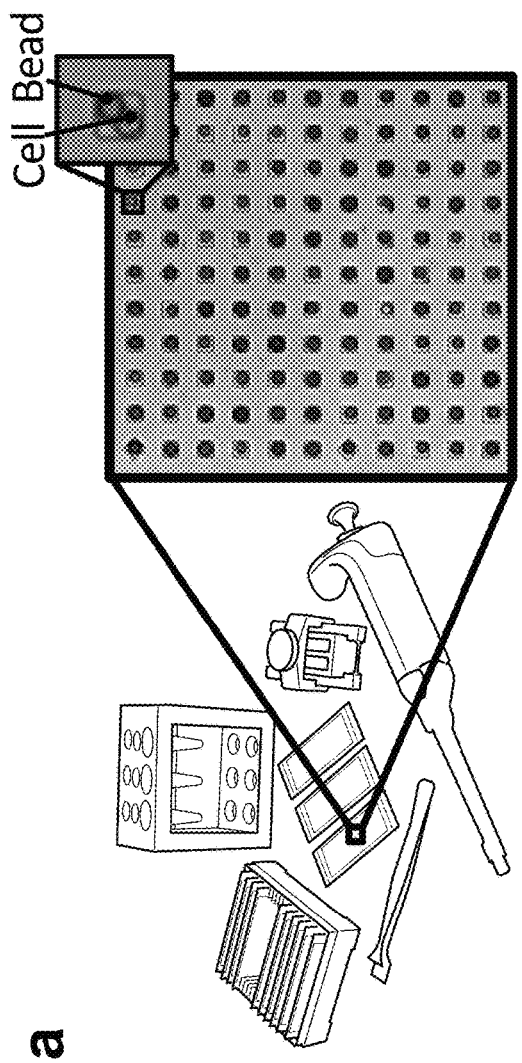
FIGS. 10A-10D illustrate an embodiment of the invention. (A) Photograph of equipment and array used to capture and lyse cells, respectively. (B) Transcripts captured from a mix of human (HEK293) and mouse (NIH/3T3) cells reveal distinct transcript mapping and single-cell resolution. Human (mouse) cells (>2,000 human (mouse) transcripts and <1,000 mouse (human) transcripts) are shown in blue (red). Among the 254 cells identified, 1.6% (shown in purple) had a mixed phenotype. (C,D) Violin plots of the number of transcripts (C) and genes (D) detected in human or mouse single-cell libraries generated by Seq-Well or Drop-Seq (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214) (center-line: Median; Limits: 1st and 3rd Quartile; Whiskers: +/−1.5 IQR; Points: Values >1.5 IQR). Using Seq-Well (Drop-Seq), an average of 37,878 (48,543) transcripts or 6,927 (7,175) genes were detected among human HEK cells (n=159 for Seq-Well; n=48 for Drop-Seq) and an average of 33,586 (26,700) transcripts or 6,113 (5,753) genes were detected among mouse 3T3 cells (n=172 for Seq-Well; n=27 for Drop-Seq) at an average read depth of 164,238 (797,915) reads per human HEK cell and an average read depth of 152,488 (345,117) read per mouse 3T3 cell.
Figure 10B:
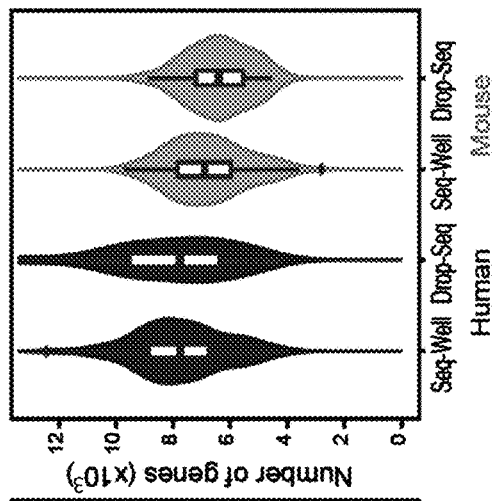
Figure 10C:
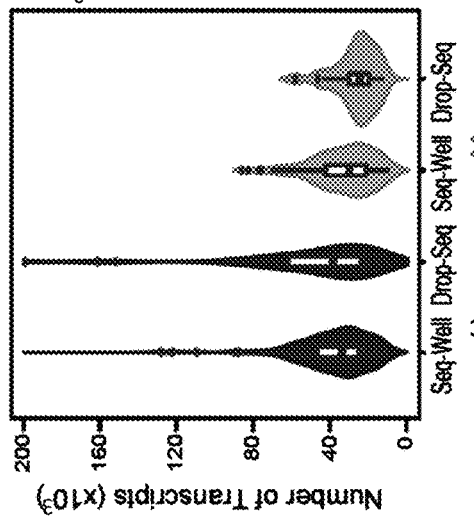
Figure 10D:
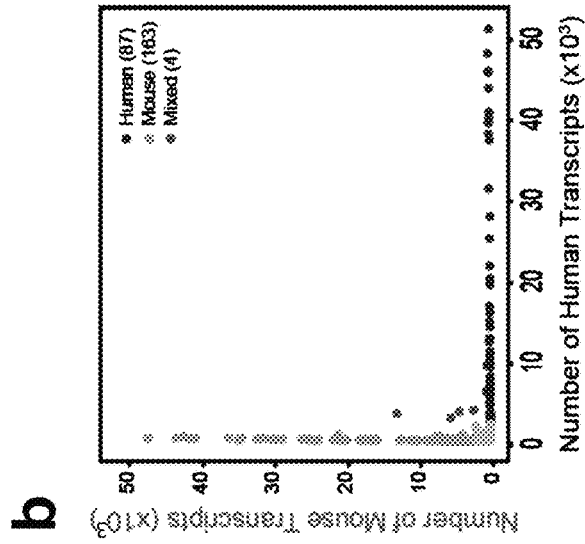

In the first experiment, HEK cells were identified as those barcodes with greater than 2,000 human transcripts and less than 1,000 mouse transcripts, while barcodes with greater than 2,000 mouse transcripts and less than 1,000 human transcripts were identified as 3T3 cells. Cells with fewer than 2,000 total transcripts were considered indeterminate, while any cell with greater than 5,000 total transcripts and more than 1,000 non-mouse or non-human transcripts was considered a multiplet (FIG. 10d). In the second experiment, HEK cells were identified as those barcodes with greater than 10,000 human transcripts, greater than 2,000 human genes, and greater than 90% human transcript alignment, while barcodes with greater than 10,000 mouse transcripts, greater than 2,000 mouse genes, and greater than 90% mouse transcript alignment were identified as 3T3 cells. Cells with fewer than 10,000 total transcripts were considered indeterminate, while any cell with greater than 10,000 total transcripts and more than 1,000 non-mouse or non-human transcripts were considered multiples (FIG. 10c, FIG. 20).

PBMC Analysis

Following sequence alignment, Applicants analyzed a total of 4,296 cells in which at least 10,000 reads, 1000 transcripts and 500 genes were detected with mRNA alignment rate greater than 65% (FIG. 11b-d), which resulted in filtering of 1,670 cells with greater than 1,000 transcripts. We analyzed a total of 6,713 genes that were detected in at least 2.5% of filtered cells across 6 sequencing runs from three separate arrays. We identified 687 variable genes with log-mean expression values greater than 0.5 and dispersion (variance/mean) greater than 0.5. We observed optimal discrimination of cell types identified through image cytometry using 11 principal components that account for the majority of the variation (51.6% cumulative variance) among variable genes and visualized using the t-distributed stochastic neighbor embedding (t-SNE) algorithm. We performed 1,000 iterations of the Barnes-Hut implementation of the t-SNE algorithm using a "perplexity" value of 40. We identified 7 distinct clusters of cells using the FindClusters function in Seurat with k.param=50 (a measure of neighborhood size) and resolution=0.75 (see below; FIG. 23). Clusters corresponding to CD4+ T cells, CD8+ T cells, B cells, NK cells, Monocytes and Dendritic Cells were all identified on the basis of significant enrichment using a ROC test implemented in Seurat (also see FIGS. 22 & 23). We removed 602 cells that comprised a distinct cluster enriched for expression of mitochondrial genes (FIG. 23) and a lower mapping rate of new transcripts and genes per sequencing read (FIG. 24), which likely represent single-cell libraries of low-complexity. We examined proportions of various cell types across arrays and sequencing runs among 3,694 cells that passed the aforementioned filtering criteria. Statistical significance of differences in the proportion of clusters between separate arrays and sequencing runs was performed using a Chi-square test (FIG. 11c). We further examined phenotypic variation within myeloid cells among identified principal components (FIG. 11d) by ranking cells on the basis of their PC score among gene with highest loadings for each principal component.

Comparison of Seq-Well PBMCs to 10× Genomics Data

We performed comparisons of gene detection and transcript capture among PBMC cell types conserved between 3,590 PBMCs (excluding dendritic cells) obtained using Seq-Well and 2,700 PBMCs from the 10× Genomics platform (http://support.10xgenomics.com/single-cell/datasets/pbmc3k). To classify PBMC cell types within the 10× genomics data, Applicants first identified 446 variable genes with log-mean expression values greater than 0.5 and dispersion (variance/mean) greater than 0.5. We then performed graph-based clustering using 13 principal components, k.param of 50, and resolution of 0.75. Cell type identity of each cluster was established on the basis of gene enrichments. Comparisons of genes and transcripts were initially performed between B cells, CD4 T cells, CD8 T cells, Monocytes, and NK cells using raw data matrices. We refined these comparisons by separately downsampling genes and transcripts within each cell type in Seq-Well data to an average read depth of 69,000 reads per cell to match the reported sequencing depth using in publicly available 10× genomics data.

M. tuberculosis Analysis

Figure 12A:
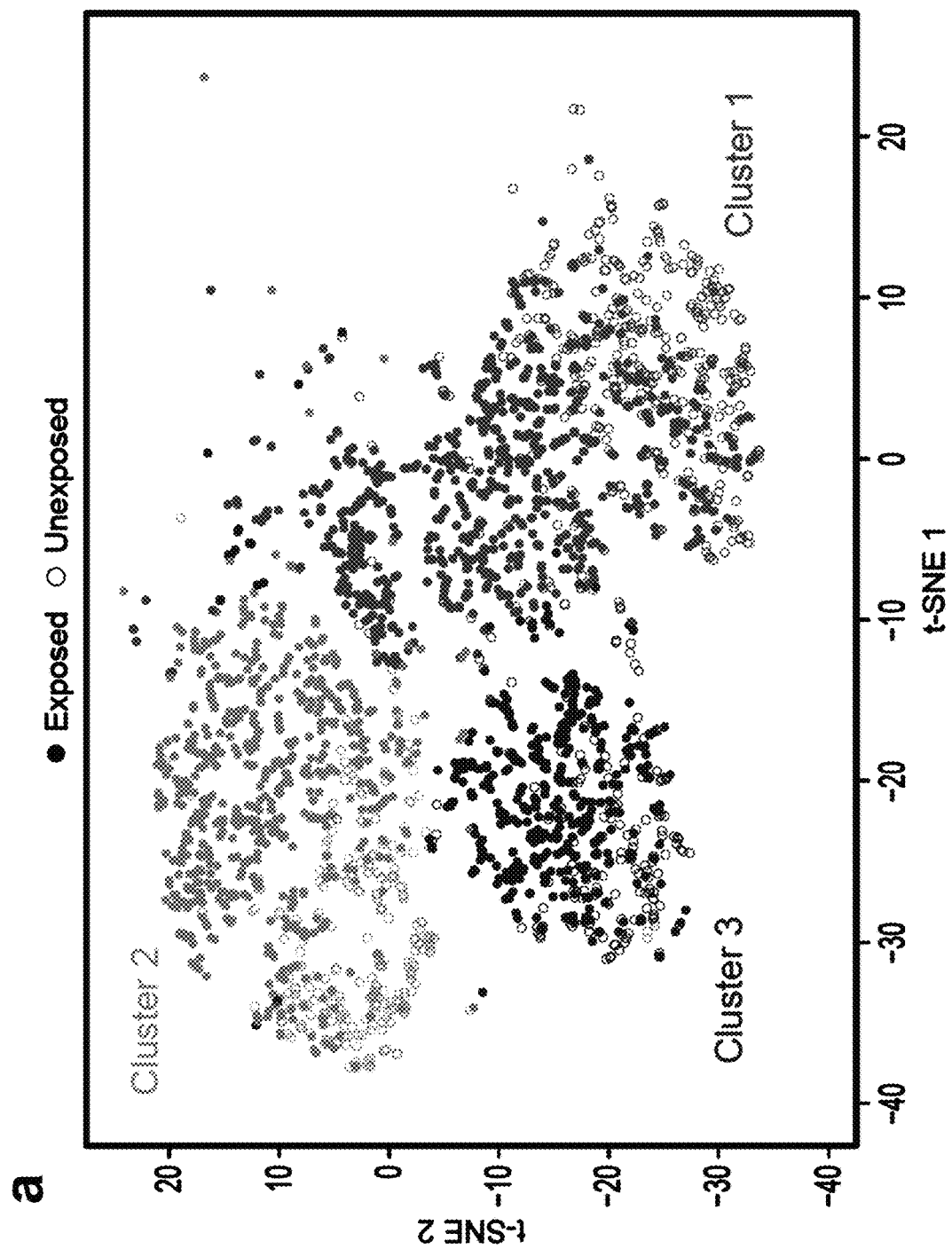
FIGS. 12A-12C illustrates sequencing of TB-exposed macrophages in a BSL3 facility using Seq-Well. (A) t-SNE visualization of single-cell clusters identified among 2,560 macrophages (1,686 exposed, solid circles; 874 unexposed, open circles) generated using 5 principal components across 377 variable genes. (B) Marker genes for the 3 phenotypic clusters of macrophages highlighted in (A). (C) Volcano plots of differential expression between exposed and unexposed macrophages within each cluster showing genes enriched in cells exposed to M. tuberculosis. In each plot, a p-value threshold of $5.0\times10^{-16}$ based on a likelihood ratio test was used to establish statistical significance, while a log 2-fold change threshold of 0.4 was used to determine differential expression. Genes with p-values less than $5.0\times10^{-6}$ are shown in cyan and absolute log 2-fold changes greater than 0.4; In magenta are genes with p-values less than $5.0\times10^{-6}$ but absolute log 2-fold changes less than 0.4; and, in black, are genes with p-values greater than $5.0\times10^{-6}$ and absolute log 2-fold changes less than 0.4.
Figure 12B:
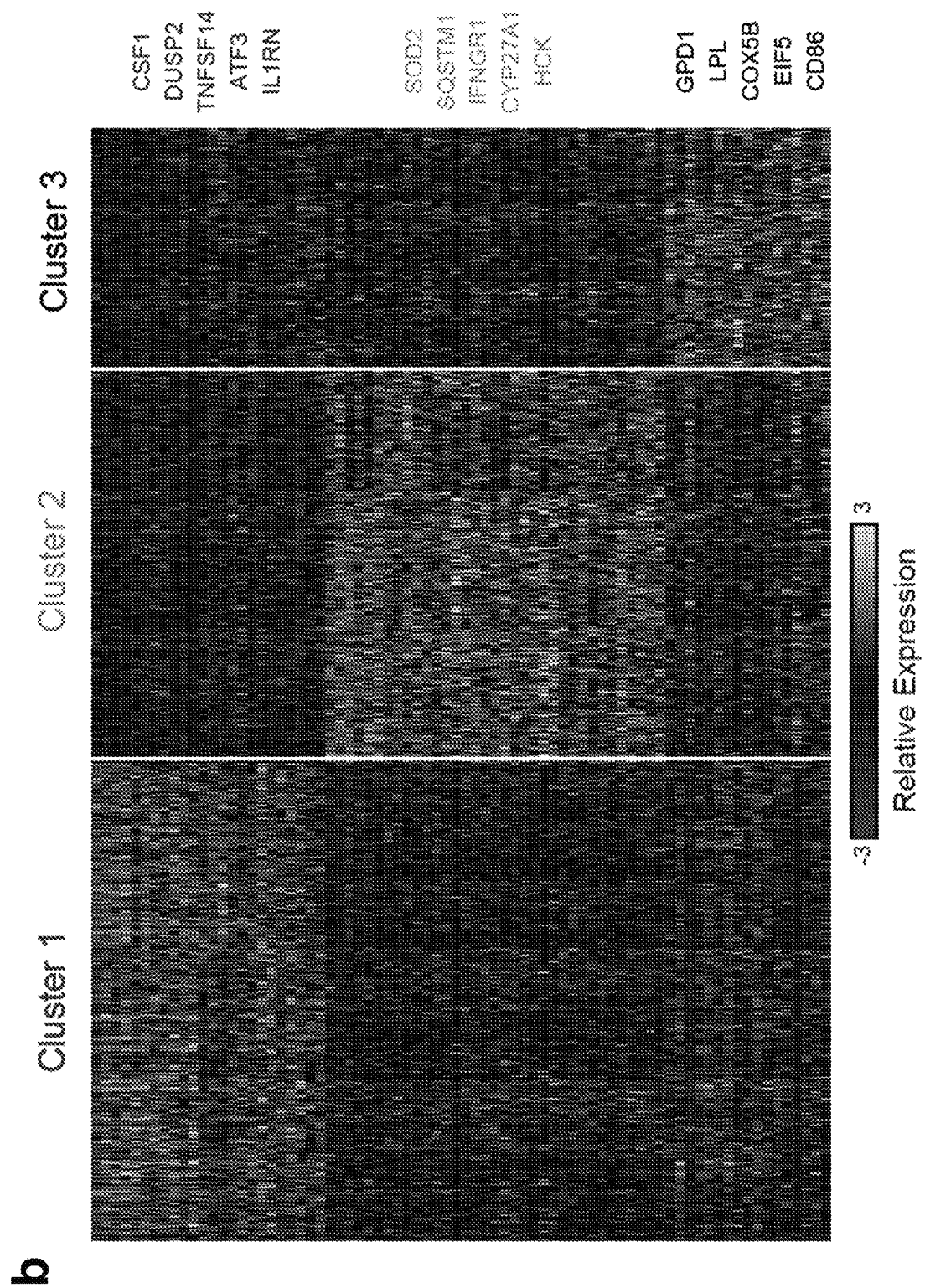
Figure 12C:
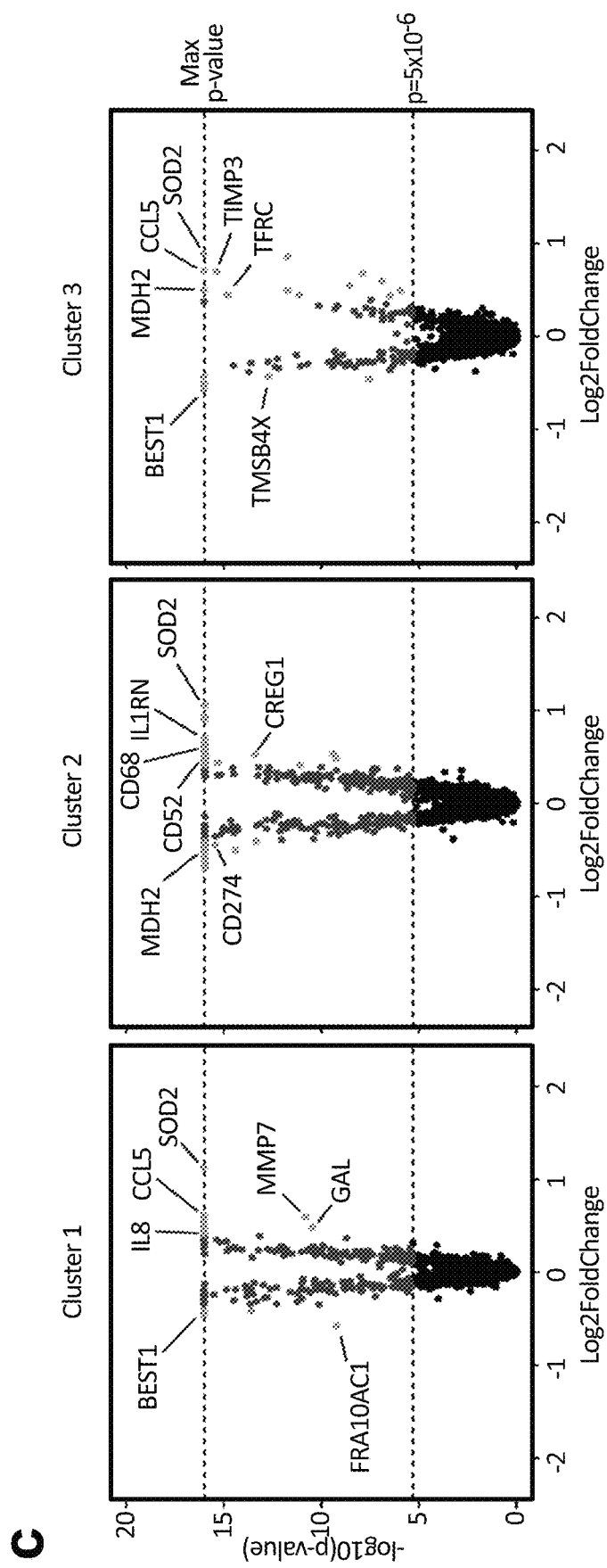
Figures 26A, 26B:
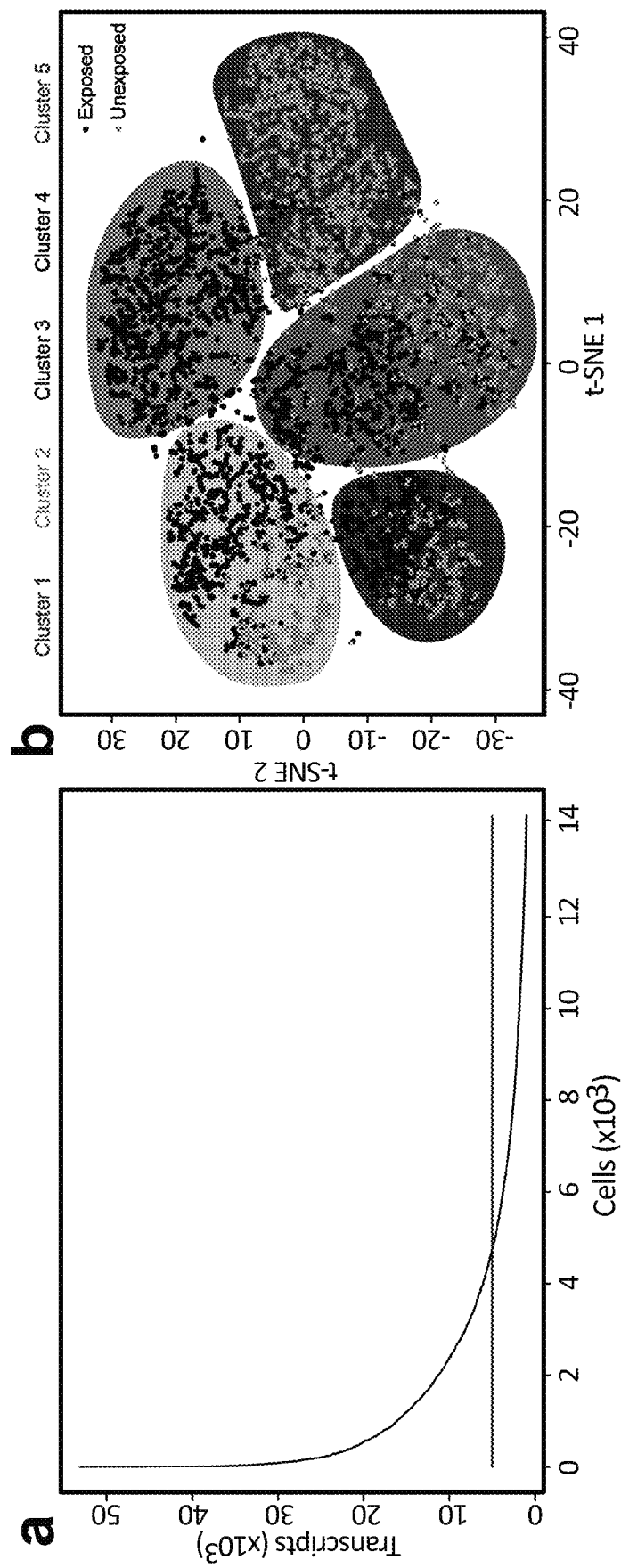
Figure 26C:
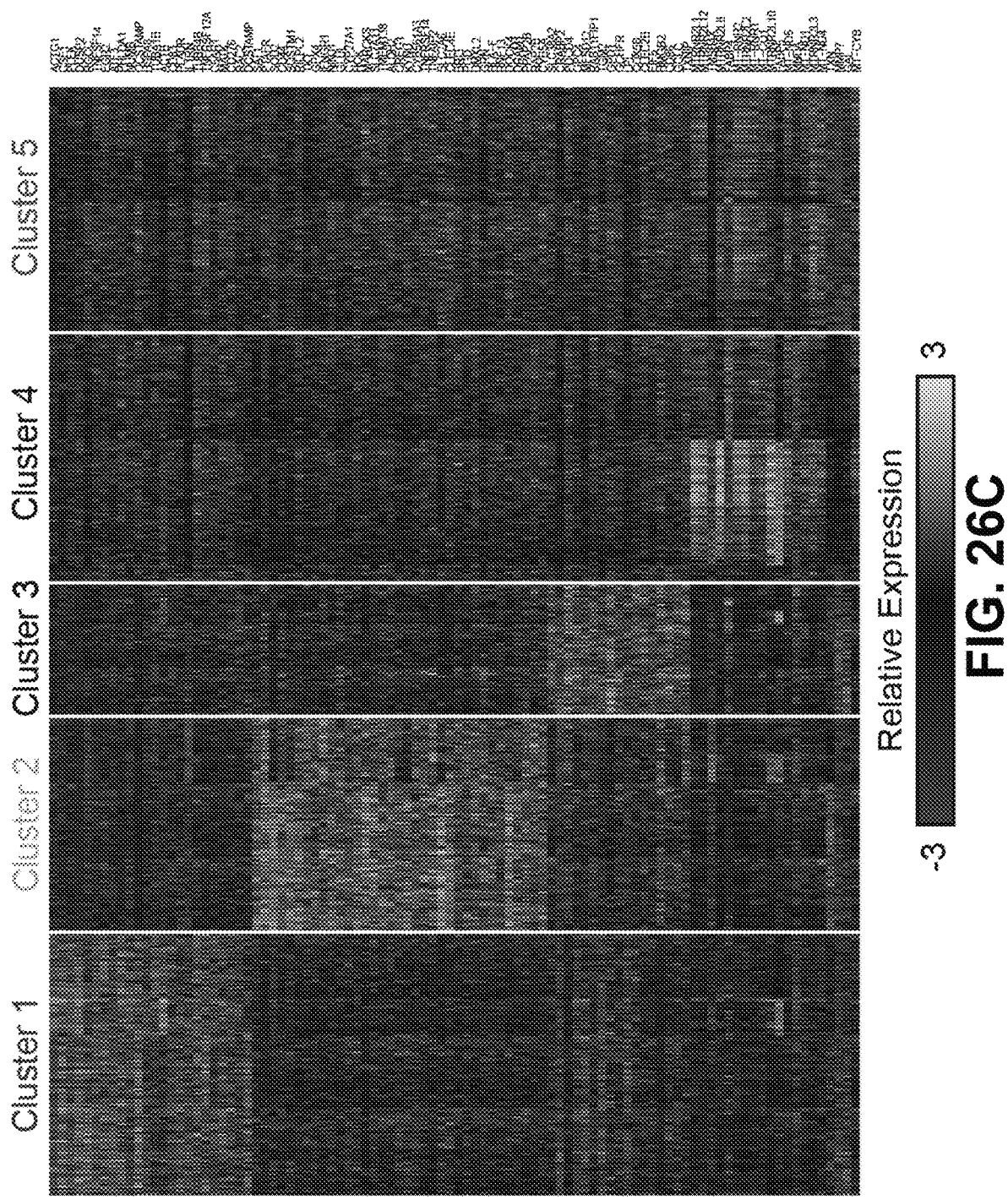
Figure 26D:
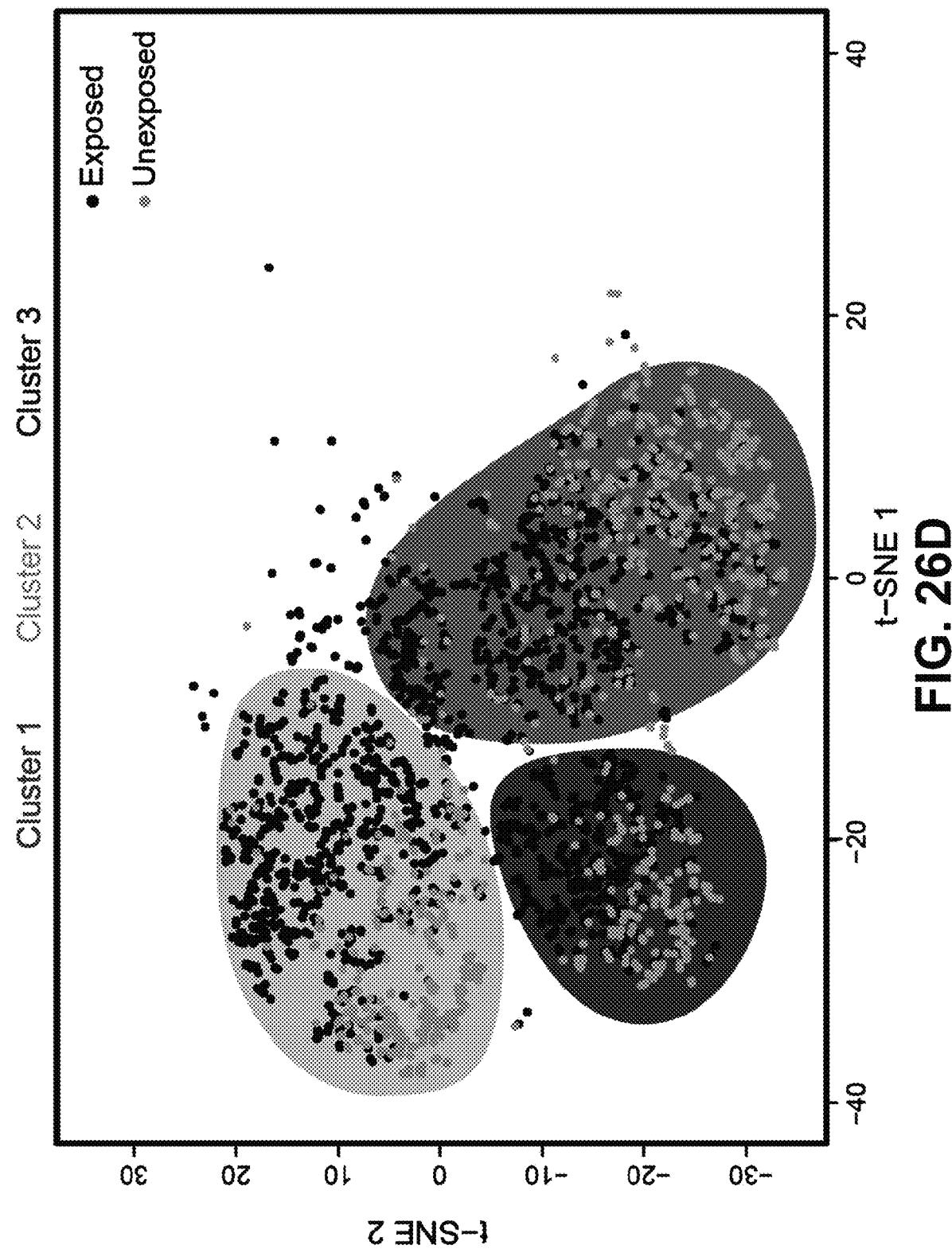
Figures 27A, 27B, 27C, 27D:
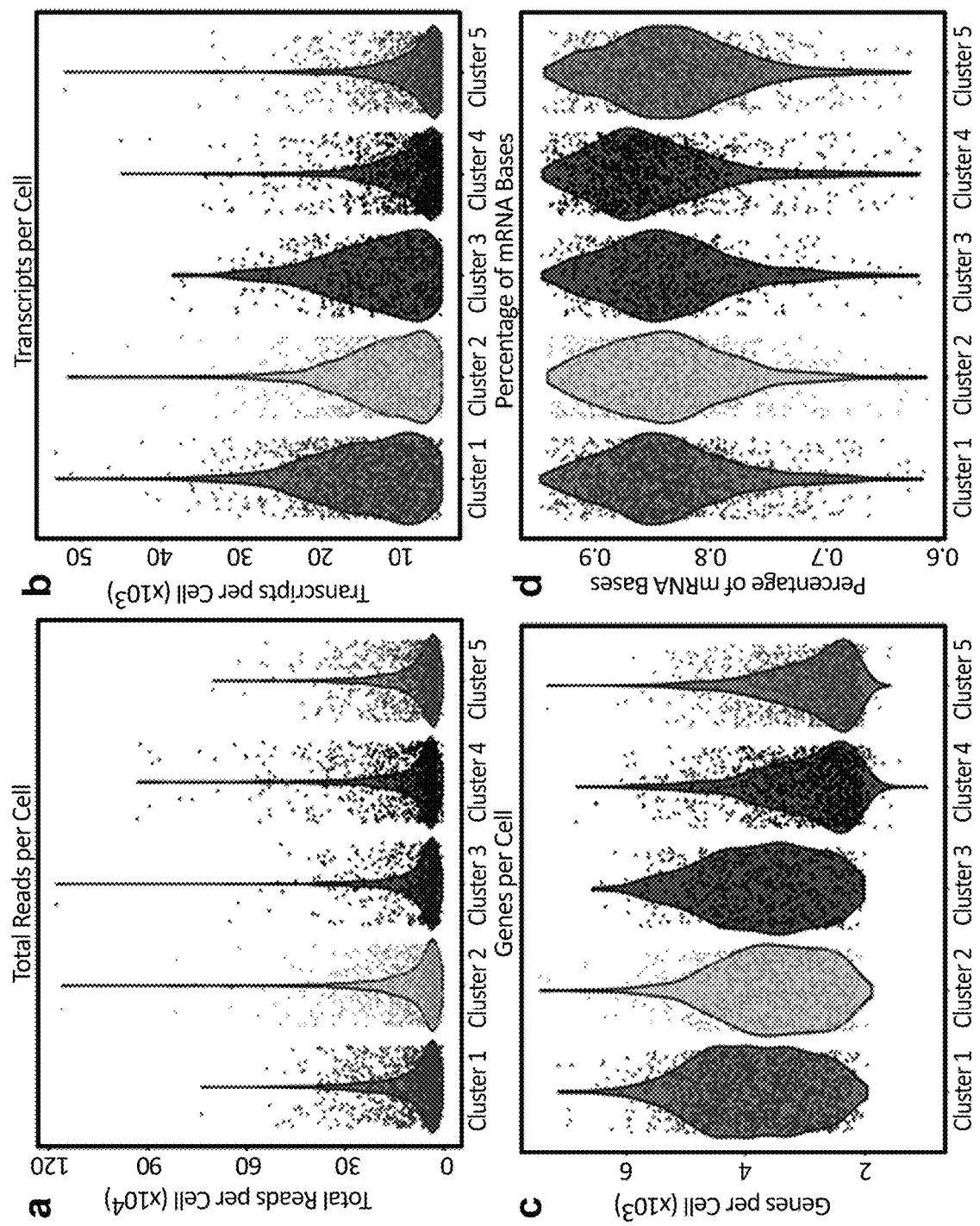

Following sequence alignment, Applicants identified a total of 14,218 cells with greater than 1,000 mapped transcripts. Initially, Applicants analyzed a subset of 4,638 macrophages with greater than 5,000 detected transcripts (FIG. 26a) and a total of 9,381 genes expressed in at least 5% of filtered cells. Principal components analysis was performed among a set of 377 variables genes, defined by genes with log mean expression greater than 0.5 and dispersion (variance/mean) greater than 0.5. We performed t-SNE clustering using the first 5 principal components since Applicants observed that they captured the majority of the biological variation in the dataset (63% cumulative variance), and that each additional principal components contributed less than 1% to the total variance. We performed 1,000 iterations of the t-SNE algorithm (Barnes-Hut implementation) using a "perplexity" value of 30. We identified 5 distinct clusters of cells in the t-SNE plot using the Find-Clusters function in Seurat with k.param=40 and resolution=0.25 (FIG. 26). We removed 2 clusters comprised of cells with reduced gene detection, transcript capture and enrichment for expression of mitochondrial genes. Following removal of low-quality cells, Applicants analyzed three distinct clusters with total of 2,560 high-quality cells (FIG. 12a, FIG. 26). Differential expression analysis was performed between clusters, and TB exposed and unexposed cells within each t-SNE cluster using a likelihood ratio test in Seurat (FIG. 12c). We performed gene set enrichment analysis to examine association of expression differences observed between M. tuberculosis exposed and unexposed control macrophages with previously published gene sets using GSEA. For each cluster, expression patterns between exposed and unexposed cells were made to complete GSEA databases.

Regressing Out Latent Technical Effects

Technical parameters governing sequencing data, such as the number of genes detected, or the transcriptomics alignment rate, often vary significantly across single cells. We sought to conservatively remove these technical effects using a 'latent-variable' approach similar to Buettner, F., et al., "Computational analysis of cell-to-cell heterogeneity in single-cell RNA-sequencing data reveals hidden subpopulations of cells" Nature Biotechnology (2015) 33, 155-60). Briefly, Applicants fit a linear model to predict the expression value of each gene based on a set of technical metrics, as well as the total number of unique genes detected in that cell. In the analyses, Applicants constructed models to adjust gene expression values for alignment rate of each cell. Applicants considered the residual expression from this model as a 'corrected' gene expression value, and used these values as input to the downstream clustering analyses.

Graph-Based Clustering of Single-Cell Transcriptomes

For all single cell-clustering analyses, Applicants used an approach similar to the recently proposed clustering strategy for Drop-Seq data. Briefly, as in Macosko et al. (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214), Applicants first identified the set of genes that was most variable across the dataset, after controlling for the relationship in single-cell RNA-seq data that inherently exists between mean expression and variability by binning genes into 20 bins based on their average expression level, and z-scoring dispersion (mean/variance) estimates within a bin. We excluded all genes which were detected in less than 2.5% of PBMCs (5% of monocytes for the Mtb experiments), and used a dispersion cutoff of 0.5 to select variable genes, resulting in the selection of 687 variable genes across 4,296 PBMCs and 377 variable genes across 4,638 macrophages.

Applicants next reduced the dimensionality of the dataset, using principal components analysis. As previously described in Macosko et al. (Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214), Applicants ran PCA using the prcomp function in R. We then selected PCs for further downstream analysis (11 PCs in PBMC analysis and 5 PCs in TB Analysis). As expected, markers for distinct cell types were highly represented among the genes with the largest scores along these PCs. We then applied t-distributed stochastic neighbor embedding (t-SNE) using cell loadings for the significant principal components as input, to visualize the structure of the data in two dimensions.

Here Applicants utilized graph-based clustering methods, similar to those that have been recently proposed for both single cell RNA-seq and mass cytometry data (Levine, J. H., et al., "Data-driven phenotypic dissection of AML reveals progenitor-like cells that correlate with prognosis" (2015) Cell 162, 184-197 & Xu, C., and Su., Z. "Identification of cell types from single-cell transcriptomes using a novel clustering method" (2015) Bioinformatics 31(12):1974-1980). We first construct a Euclidean distance matrix on the loadings for the significant principal components as described above, and use this to construct a k-nearest neighbor graph (KNN, k=50 in PBMC analysis, k=40 in TB analysis). Our goal was to identify 'quasi-cliques' Xu, C., and Su., Z. "Identification of cell types from single-cell transcriptomes using a novel clustering method" (2015) Bioinformatics 31(12):1974-1980), or 'communities' (Levine, J. H., et al., "Data-driven phenotypic dissection of AML reveals progenitor-like cells that correlate with prognosis" (2015) Cell 162, 184-197) of cells that were highly interconnected across this graph. Therefore Applicants first converted the KNN graph into a weighted shared nearest neighbor (SNN) graph, where the weight between any two cells was represented by the percent overlap in their respective K-nearest neighborhoods (Jaccard distance), and pruned low-quality edges with a Jaccard distance of <0.1 (less than 10% overlap in local neighborhoods). Finally, to group the cells into clusters, Applicants used a recently developed method for modularity optimization which aims to optimize a function describing the density of connections within a cluster versus connections between clusters, essentially to identify highly interconnected nodes within the SNN graph. Here, Applicants applied the smart local moving algorithm, which is similar to the widely used 'Louvain' algorithm for community detection, but implements a local moving heuristic that enables communities to be split up and iteratively re-organized in an attempt to improve the overall partition modularity. This grants the SLM algorithm additional freedom in identifying an optimal clustering solution, and Applicants empirically observed increased sensitivity and consistency applying this approach to single cell data.

Example

Figures 15A, 15B, 15C:
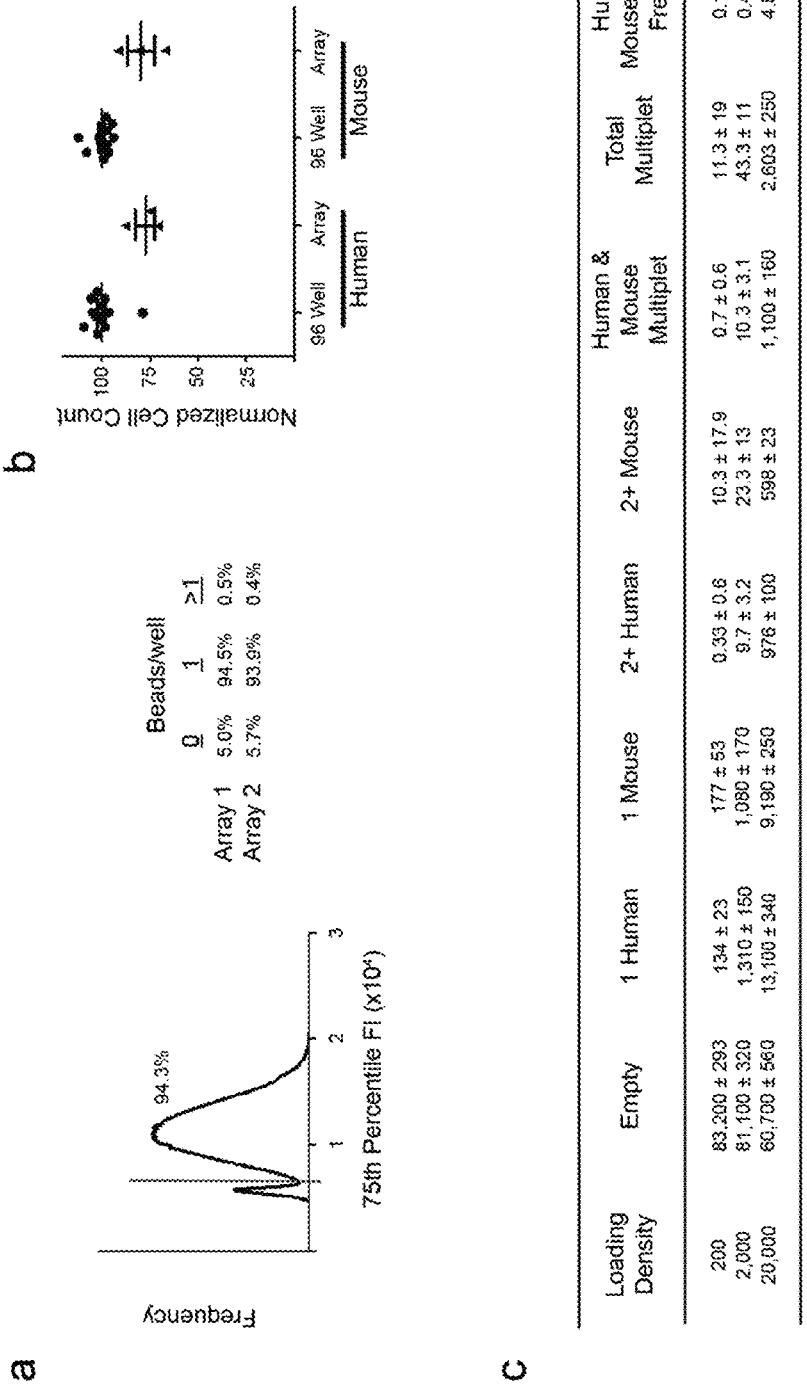
FIGS. 15A-15C illustrates bead and cell loading efficiency. (A) Two arrays were loaded with barcoded beads through intermittent rocking. After washing, arrays were imaged in transmitted light and AF488 channel to capture bead autofluorescence. A plot of the frequency of the $75^{th}$ percentile AF488 well intensity across the array (Panel 1) and the frequency of wells containing zero, one and multiple beads is displayed (Panel 2). (B) 200 µL of a 1:1 mix of fluorescently labeled human (HEK 293) and mouse (3T3) cell solution was loaded into 3 arrays and 12 wells of a 96 well plate. The number of cells loaded into each array and well as enumerated by fluorescent imaging is plotted, normalized to the average number of cells/well in the 96 well plate. Mean and standard error are denoted by line and error bars respectively. (C) $2\times10^2$, $2\times10^3$, and $2\times10^4$ total cells of a 1:1 mix of fluorescently labeled HEK 293T and 3T3 cells were loaded onto three functionalized arrays each. All arrays were fluorescently imaged to enumerate the number of each cell line in each array microwell. The mean±standard deviation of the number of empty, single and multiple occupancy wells across the three replicate arrays for each loading density is displayed along with the mean±standard deviation of the percentage of occupied wells containing a cell from each species.

According to the Example, single cells and barcoded poly(dT) mRNA capture beads are confined in a PDMS array of ~86,000 subnanoliter wells. Well dimensions are designed to accommodate only one bead enabling single-bead loading efficiencies of ~95% (FIG. 10a, FIG. 15a). A simplified cell-loading scheme, in turn, enables capture efficiencies around 80% (FIG. 15b), with a rate of dual occupancy that can be tuned by adjusting the number of cells loaded and visualized prior to processing (FIG. 15c).

Figures 16A, 16B, 16C:
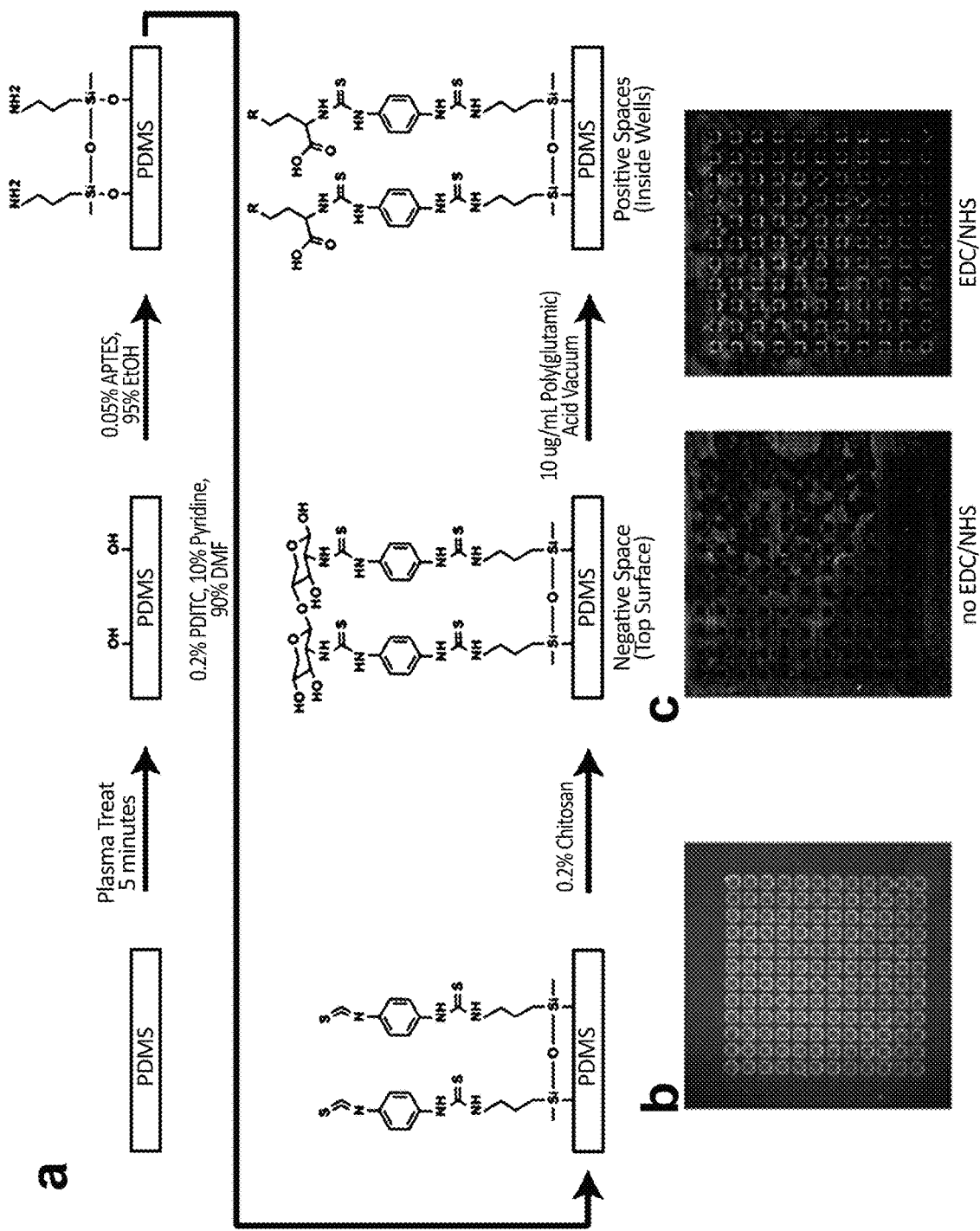
FIGS. 16A-16C illustrate PDMS surface chemistry functionalization protocol and differential functionalization of microwell arrays. (A) The surface of the PDMS device is initially treated with an air plasma under mild vacuum, terminating the surface in hydroxyls. This PDMS surface is aminated using (3-Aminopropyl)triethoxysilane (APTES). The amine surface is then activated with PDITC to create an isothiocyanate surface. The isothiocyanate on the top surface of the array (negative space) is covalently linked to chitosan polymers through their amine group. The hydrophobicity of the isothiocyanate surface prevents solvation of the microwells with the aqueous chitosan solution, preventing chitosan from reacting with the inner well surfaces (positive space). These surfaces are subsequently reacted with the free amine of poly(glutamic) acid polymers under vacuum to drive the solvation of the wells. (B) The top surface of a PDITC-activated array was coated with streptavidin-PE (red) and the inner well surfaces were coated with streptavidin-AF488 (green) using same method used to functionalize with chitosan and poly(glutamate). (C) Two chitosan/poly(glutamate) bifunctionalized arrays were submerged in MES buffer without (Panel 1) or with (Panel 2) 100 µg/mL EDC and 10 µg/mL NHS for 10 minutes. The arrays were washed and then submerged in PBS solution containing 1 µg/mL AF568-labeled antibody overnight. After washing, arrays were imaged for AF568 fluorescence.
Figure 17A:
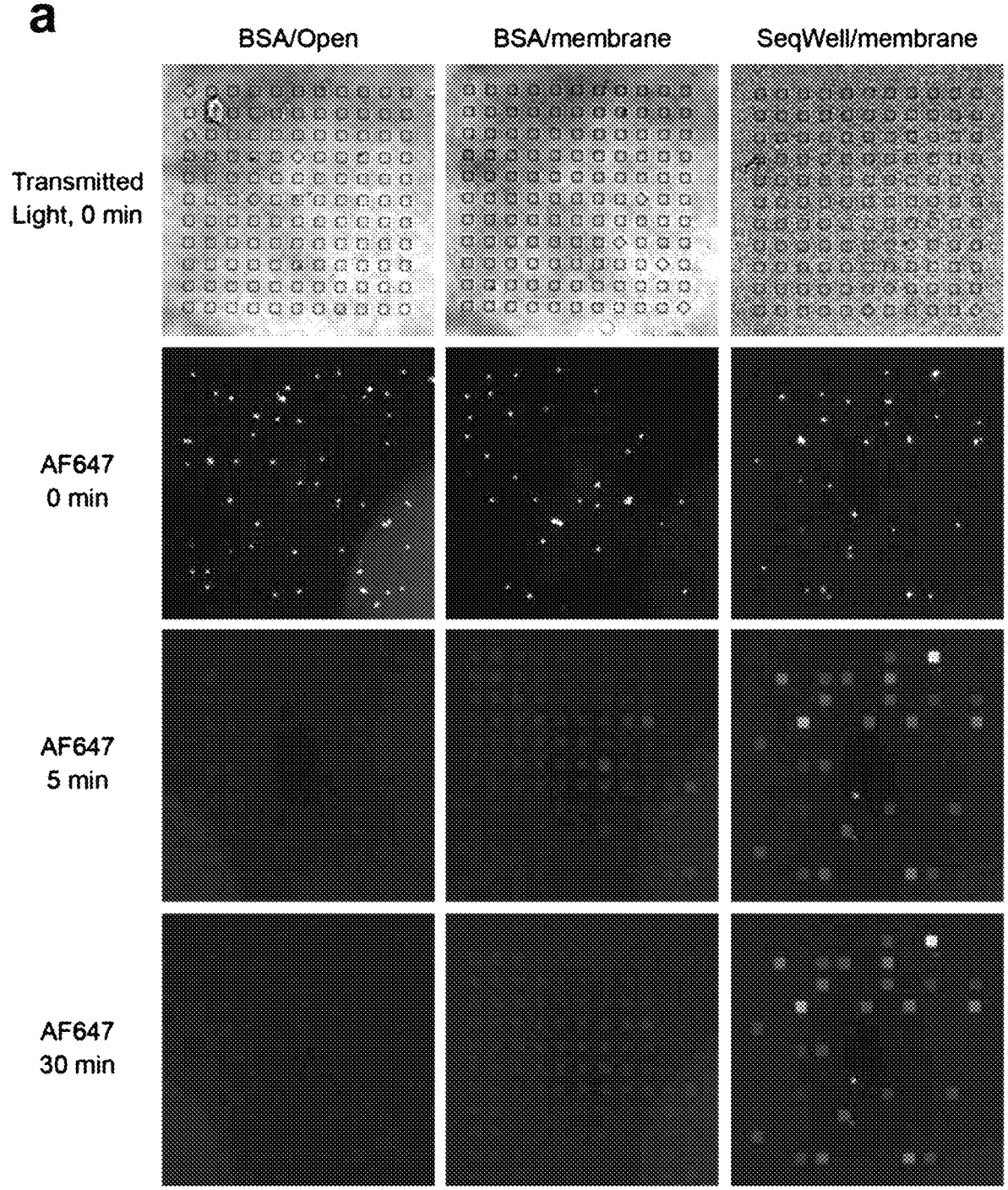
FIGS. 17A-17C illustrate microwell sealing with semi-permeable membrane. PBMCs labeled with αCD45-AF647 were loaded into two BSA-blocked arrays and one array functionalized with chitosan and poly(glutamate). A semi-permeable membrane was attached to one of the BSA-blocked arrays and the chitosan:polyglutamate functionalized array prior to addition of lysis buffer. (A) Example images of transmitted light and AF647 fluorescence of the arrays before and 5 and 30 minutes after addition of lysis buffer are displayed for each array. (B) The total fluorescence intensity (FI) of all pixels associated with cells within a well is plotted against the median fluorescent intensity (MFI) of the volume of the same well 5 minutes after lysis for 12,100 wells from each array. (C) The MFI of the well volume 5 minutes after lysis is plotted against the MFI of the volume of the same well 30 minutes after lysis for the same 12,100 wells from each array.
Figures 17B, 17C:
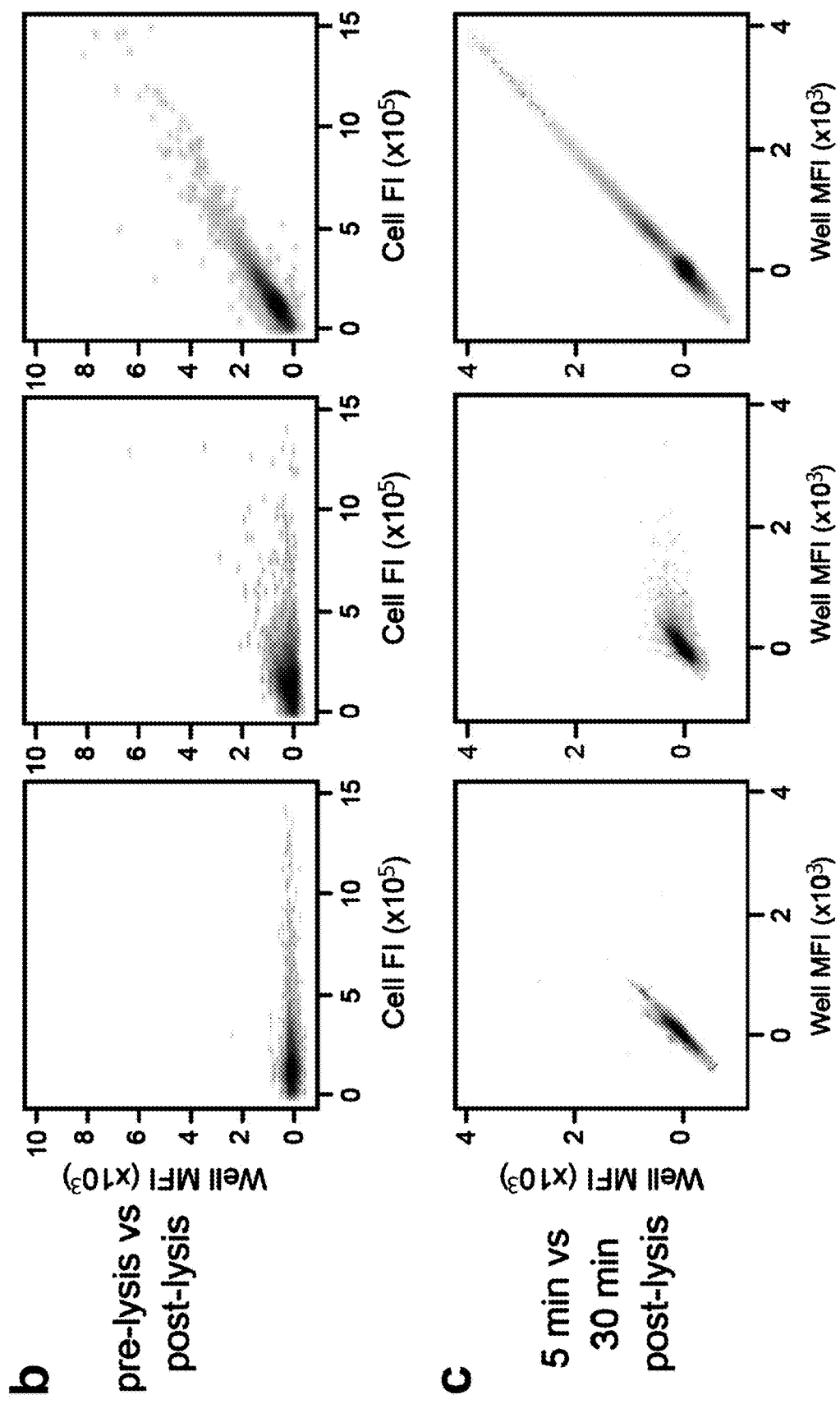

Selective chemical functionalization facilitates reversible attachment of a semi-permeable polycarbonate membrane (10 nm pore size) in physiologic buffers, enabling rapid solution exchange for efficient cell lysis and trapping biological macromolecules, increasing transcript capture during hybridization and reducing cross-contamination (FIG. 16a). The array's unique three-layer surface functionalization comprises an amino-silane base (Steinberg, G., et al., "Strategies for covalent attachment of DNA to beads" (2004) Biopolymers 73, 597-605) crosslinked to bifunctional poly (glutamate)/chitosan top via a p-Phenylene diisothiocyante intermediate (FIG. 16); this bifunctional top, with poly (glutamate) coating the inner surfaces of the nanowells (where cells are lysed) and chitosan the array's top surface (where the membrane binds), prevents non-specific binding of RNA to the array and efficient sealing, respectively (FIG. 16b,c). To test sealing and buffer exchange, Applicants monitored the fluorescence of dye-labeled, cell-bound antibodies before and after adding a guanidinium-based lysis buffer. We observed rapid diffusion of the antibodies throughout the wells within five minutes of buffer addition and, unlike unsealed or previously-described, membrane-covered BSA-blocked arrays (Dekoskey, B. J., et al., "High-throughput sequencing of the paired human immunoglobulin heavy and light chain repertoire" (2013) Nature Biotechnology 31, 166-169), little change in fluorescent signal over 30 minutes, suggesting robust retention of biological macromolecules despite use of a strong chaotrope (FIG. 17).

After lysis, cellular mRNAs are captured by bead-bound poly(dT) oligonucleotides that also contain a universal primer sequence, a cell barcode, and a unique molecular identifier (UMI). Next, the membrane is peeled off and the beads are removed for subsequent bulk reverse transcription, amplification, library preparation and paired-end sequencing, as previously described Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214). Critically, beyond a disposable array and membrane, Seq-Well only requires a pipette, a manual clamp, an oven, and a tube rotator to achieve stable, barcoded single-cell cDNAs (FIG. 10a), enabling it to be performed almost anywhere.

Figure 18:
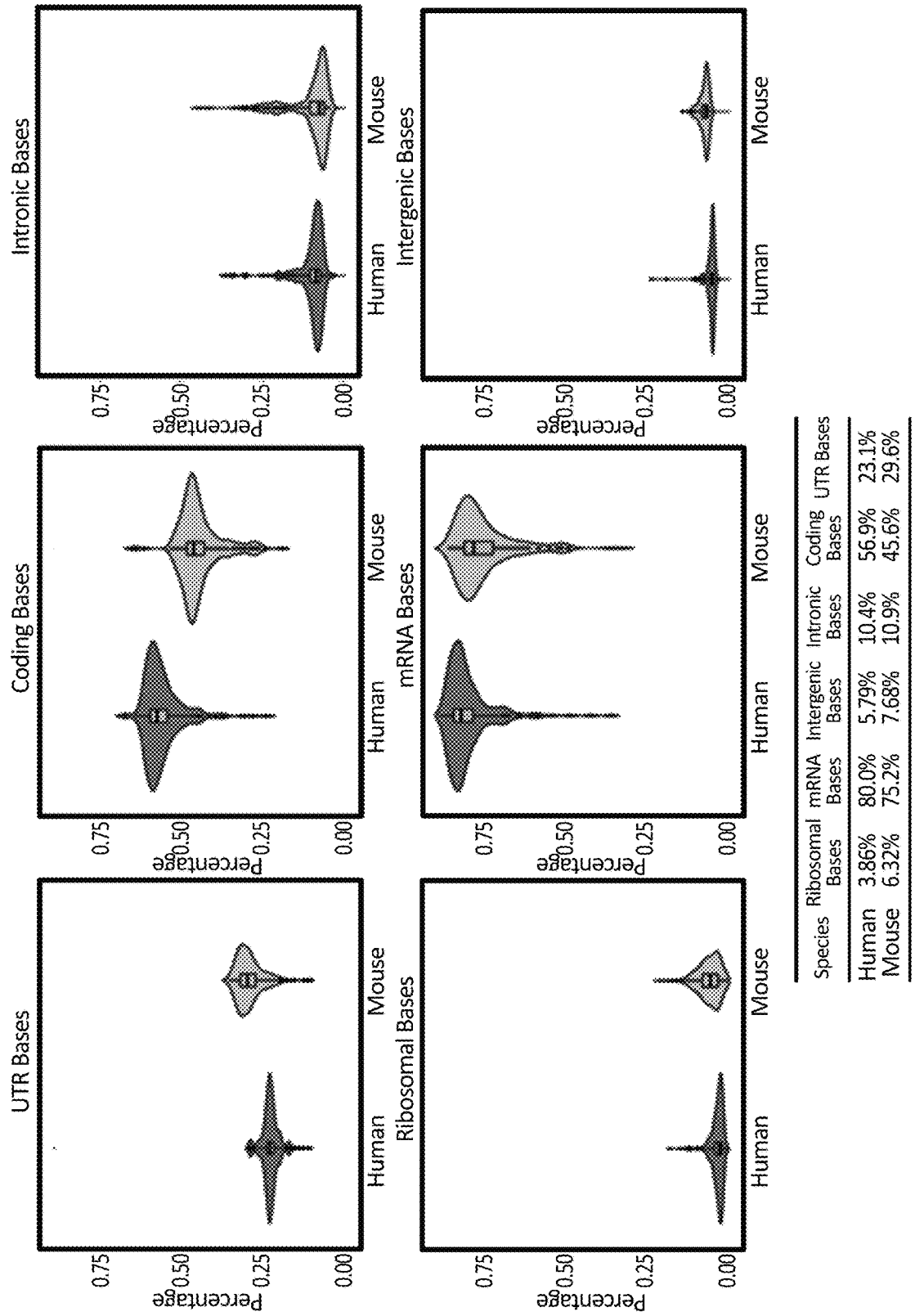
FIG. 18 illustrates read mapping quality. Read mapping quality matrices were generated for each sample for human (blue) and mouse (red) cells, aligned to hg19 and mm10, respectively. High quality samples had relatively higher percentages of annotated genomic (genic) and exonic transcripts and low percentages of annotated intergenic and ribosomal transcripts (Center-line: Median; Limits: $1^{st}$ and $3^{rd}$ Quartile; Whiskers: +/−1.5 IQR; Points: Values >1.5 IQR).
Figures 19A, 19B, 19C, 19D, 19E, 19F, 19G:
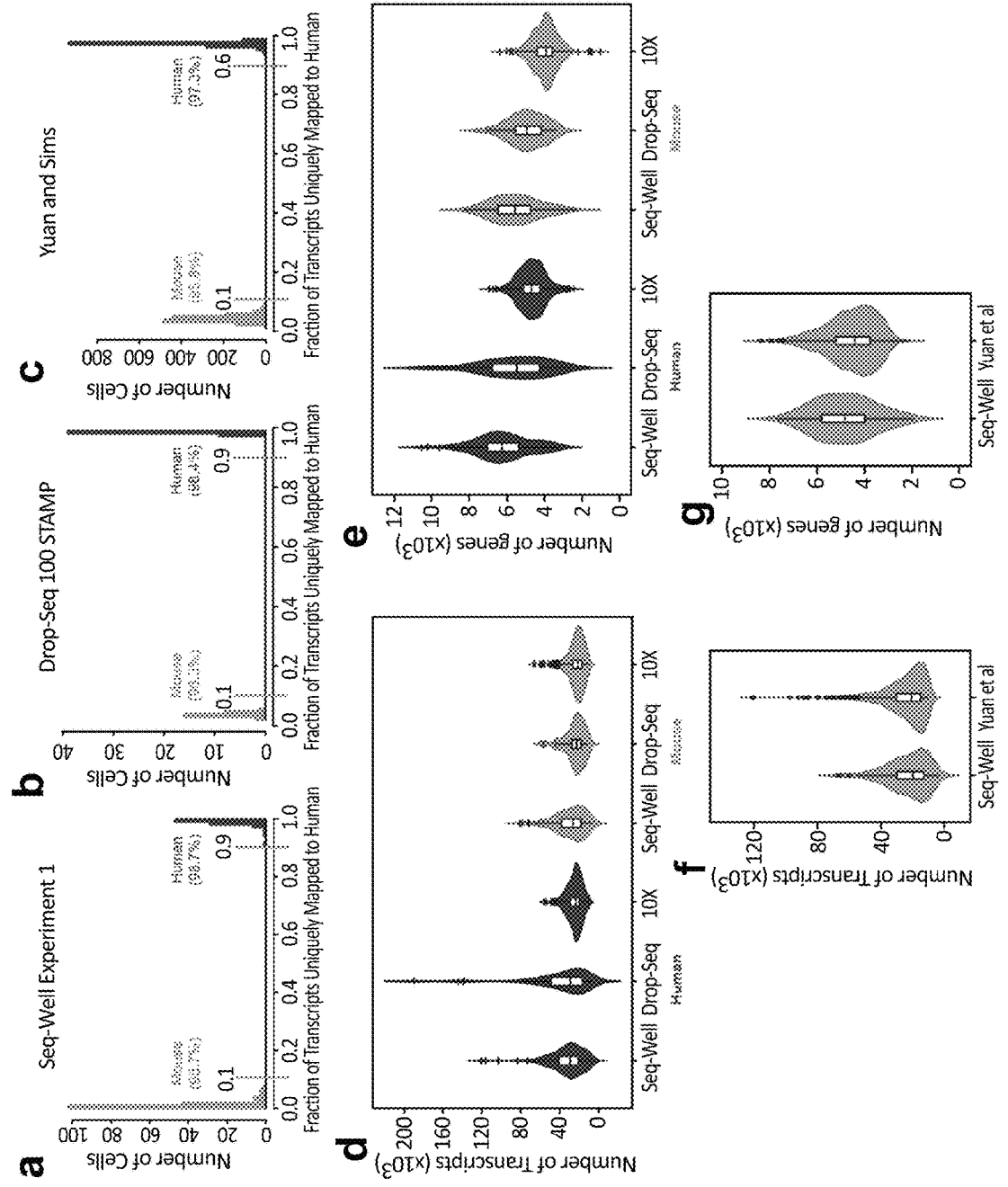
FIGS. 19A-19G illustrate a comparison of gene and transcript capture and percent contamination among massively-parallel scRNA-Seq methods using mouse and human cell lines. Histograms of the percent cross-species contamination in (A) Seq-Well, (B) Drop-Seq (Ref 12), and (C) Yuan and Sims (Ref. 15). In each plot, cells with greater than 90% of human transcripts are displayed in blue and cells with less than 10% human transcripts are displayed in red. (D) Transcript capture in human (blue) and mouse (red) cell lines across three massively-parallel, bead-based single-cell sequencing platforms (Seq-Well, Drop-Seq, and 10× Genomics, with downsampling to an average read-depth of 80,000 reads per cell, consistent with 10× genomics data (Center-line: Median; Limits: $1^{st}$ and $3^{rd}$ Quartile; Whiskers: +/−1.5 IQR; Points: Values >1.5 IQR). We detect an average of 32,841 human transcripts and 29,806 mouse transcripts using Seq-Well compared to an average of 39,400 human transcripts and 24,384 mouse transcripts using Drop-Seq, an average of 24,751 human transcripts and 22,971 mouse transcripts using 10× Genomics (available from http://support.10xgenomics.com/single-cell/datasets/hgmm). (E) Gene detection across human and mouse cell lines across the same three single-cell sequencing platforms with downsampling to the average read-depth of 80,000 reads per cell, consistent with 10× genomics (Center-line: Median; Limits: $1^{st}$ and $3^{rd}$ Quartile; Whiskers: +/−1.5 IQR; Points: Values >1.5 IQR). We detect an average of 6,174 human genes and 5,528 mouse genes using Seq-Well, an average of 5,561 human genes and 4,903 mouse genes using Drop-Seq and an average of 4,655 human genes and 3,950 mouse genes using 10× Genomics. (F) Downsampling to an average of 42,000 reads per cell consistent with data published in Yuan and Sims 2016, results in average detection of 23,061 mouse transcripts using Seq-Well compared to an average of 24,761 mouse transcripts using the Yuan and Sims platform (Center-line: Median; Limits: $1^{st}$ and $3^{rd}$ Quartile; Whiskers: +/−1.5 IQR; Points: Values >1.5 IQR). (G) Downsampling to an average of 42,000 reads per cell results in average detection of 4,827 mouse genes using Seq-Well compared to an average of 4,569 mouse genes using the Yuan and Sims platform (Center-line: Median; Limits: $1^{st}$ and $3^{rd}$ Quartile; Whiskers: +/−1.5 IQR; Points: Values >1.5 IQR).

To assess transcript capture efficiency and single-cell resolution, a mixture of $5 \times 10^3$ human (HEK293) and $5 \times 10^3$ mouse (3T3) cells was profiled using Seq-Well. The average fraction of reads mapping to exonic regions was 77.5% (FIG. 18), demonstrating high quality libraries. Shallow sequencing from a fraction of an array revealed highly organism-specific libraries, suggesting single-cell resolution and minimal cross-contamination (FIG. 10b; FIG. 19a-c). In the absence of membrane sealing, by comparison, poor transcript and gene detection, and substantial cross-contamination was obtained (FIG. 13). Deeper sequencing of a fraction of a second array, detected an average of 37,878 mRNA transcripts from 6,927 genes in HEK cells and 33,586 mRNA transcripts from 6,113 genes in 3T3 cells, comparable to a droplet-based approach using the same mRNA capture beads Macosko, E. Z., Basu, A., Satija, R., Nemesh, J., Shekar, K., Goldman, M., Tirosh, I., Bialas, A. R., Kamitaki, N., Martersteck, E. M., Trombetta, J. J., Weitz, D. A., Sanes, J. A., Shalek, A. K., Regev, A., McCarroll, S. A. "Highly Parallel Genome-wide Expression Profiling of Individual Cells Using Nanoliter Droplets" Cell, 161, 1202-1214). (FIG. 10c,d, FIGS. 19, 20). Upon matched-read downsampling, transcript and gene detection levels were observed to be consistent with other massively-parallel bead-based scRNA-Seq methods (FIG. 19d-g). Moreover, there were strong correlations between bulk RNA-seq data and populations constructed in silico from individual HEK cells ($R=0.751\pm0.073$-$0.983\pm0.0001$ for populations of 1-1,000 single cells, respectively), suggesting representative cell and transcript sampling (FIG. 21).

Figures 11A, 11B:
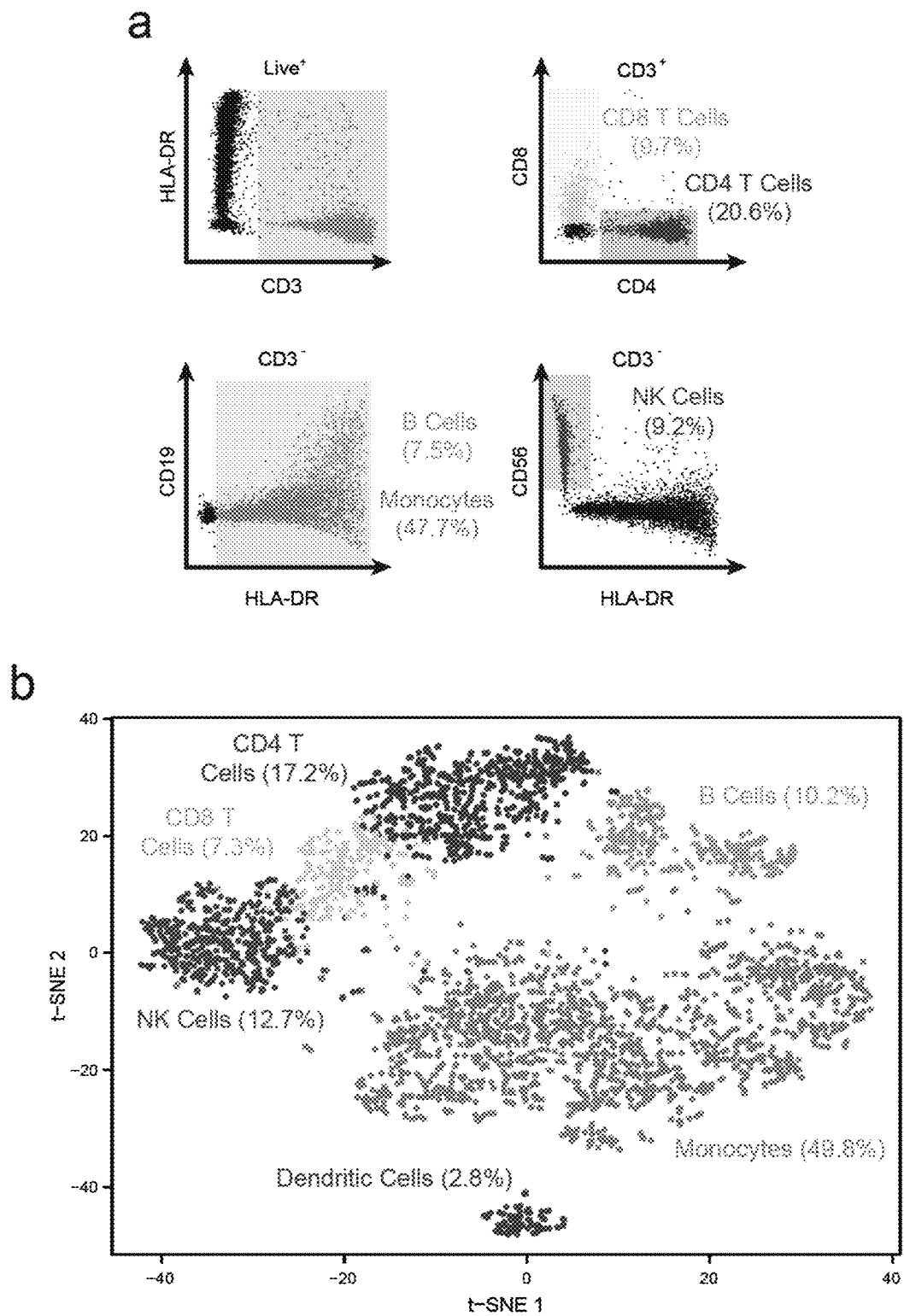
FIGS. 11A-11B illustrate combined image cytometry and scRNA-Seq of human PBMCs. (A) The hierarchical gating scheme (with the frequencies of major cell subpopulations) used to analyze PBMCs that had been labeled with a panel of fluorescent antibodies, loaded onto three replicate arrays and imaged prior to bead loading and transcript capture (Methods). Myeloid cells (green) were identified as the population of hCD3(−) HLA-DR(+) CD19(−) cells; B cells (orange) as the subset of hCD3(−) HLA-DR(+) CD19(+) cells; CD4 T cells (blue) as the subset of CD3(+) CD4(+) cells; CD8 T cells (yellow) as the CD3(+) CD8(+) subset of cells; and, NK cells (red) as the subset of CD3(−) HLA-DR (−) CD56(+) CD16(+) cells. (B) t-SNE visualization of single-cell clusters identified among 3,694 human Seq-Well PBMCs single-cell transcriptomes recovered from the imaged array and the two additional ones (FIGS. 22-24). Clusters (subpopulations) are labeled based on annotated marker gene (FIG. 22). (C) The distribution of transcriptomes captured on each of the 3 biological replicate arrays, run on separate fractions of the same set of PBMCs. All shifts are insignificant save for a slightly elevated fraction of CD8 T cells in array 1 (*, $p=1.0\times10^{-11}$; Chi-square Test, Bonferroni-corrected). (D) A heatmap showing the relative expression level of a set of inflammatory and antiviral genes among cells identified as monocytes.
Figure 11C:
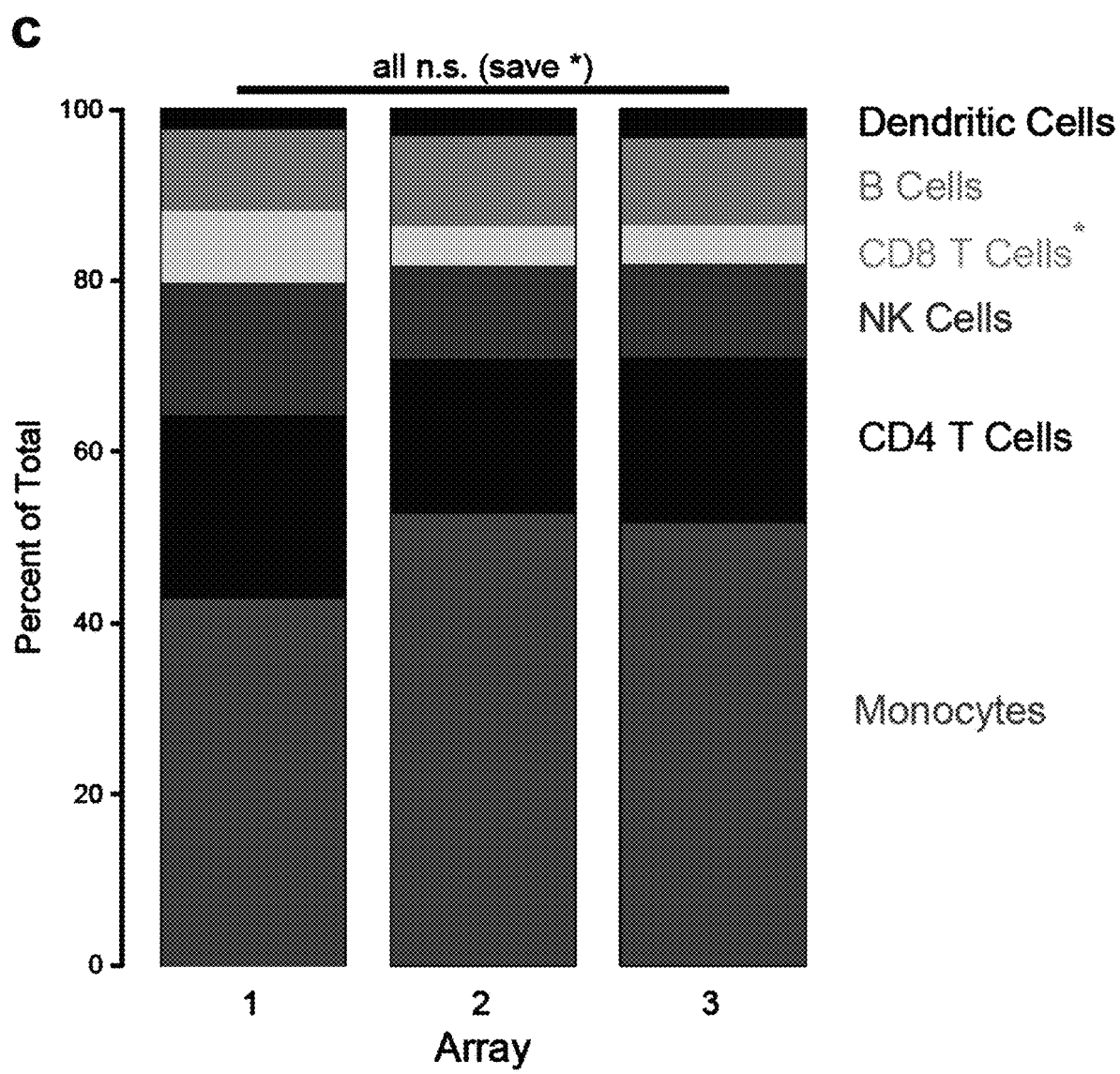

Next, to examine the ability of Seq-Well to resolve populations of cells in complex primary samples, human peripheral blood mononuclear cells (PBMCs) were loaded into arrays in triplicate prior to beads, allowing performance of on-array multi-color imaging cytometry (FIG. 11a,b). Sequencing one-third of the beads recovered from each array yielded 3,694 high-quality single-cell libraries. Unsupervised graph-based clustering revealed unique subpopulations corresponding to major PBMC cell types (FIG. 11b, FIGS. 3, 22-24). Each array yielded similar subpopulation frequencies (FIG. 11c), with detection efficiencies comparable to other massively-parallel technologies (FIG. 25). The proportion of each subpopulation determined by sequencing also matched on-array immunophenotyping results (FIG. 11a,b). Critically, sequencing provides additional information: in addition to resolving dendritic cells from monocytes (FIG. 11b), Applicants found significant variation among the monocytes (captured in PC3) due to differential expression of inflammatory and anti-viral gene programs (FIG. 11d)1,3. Overall, characterizing a sample in two ways using a single platform increases the amount of the information that can be extracted from a precious specimen, while also allowing analysis of one measurement in light of the other.

Figures 24A, 24B, 24C, 24D:
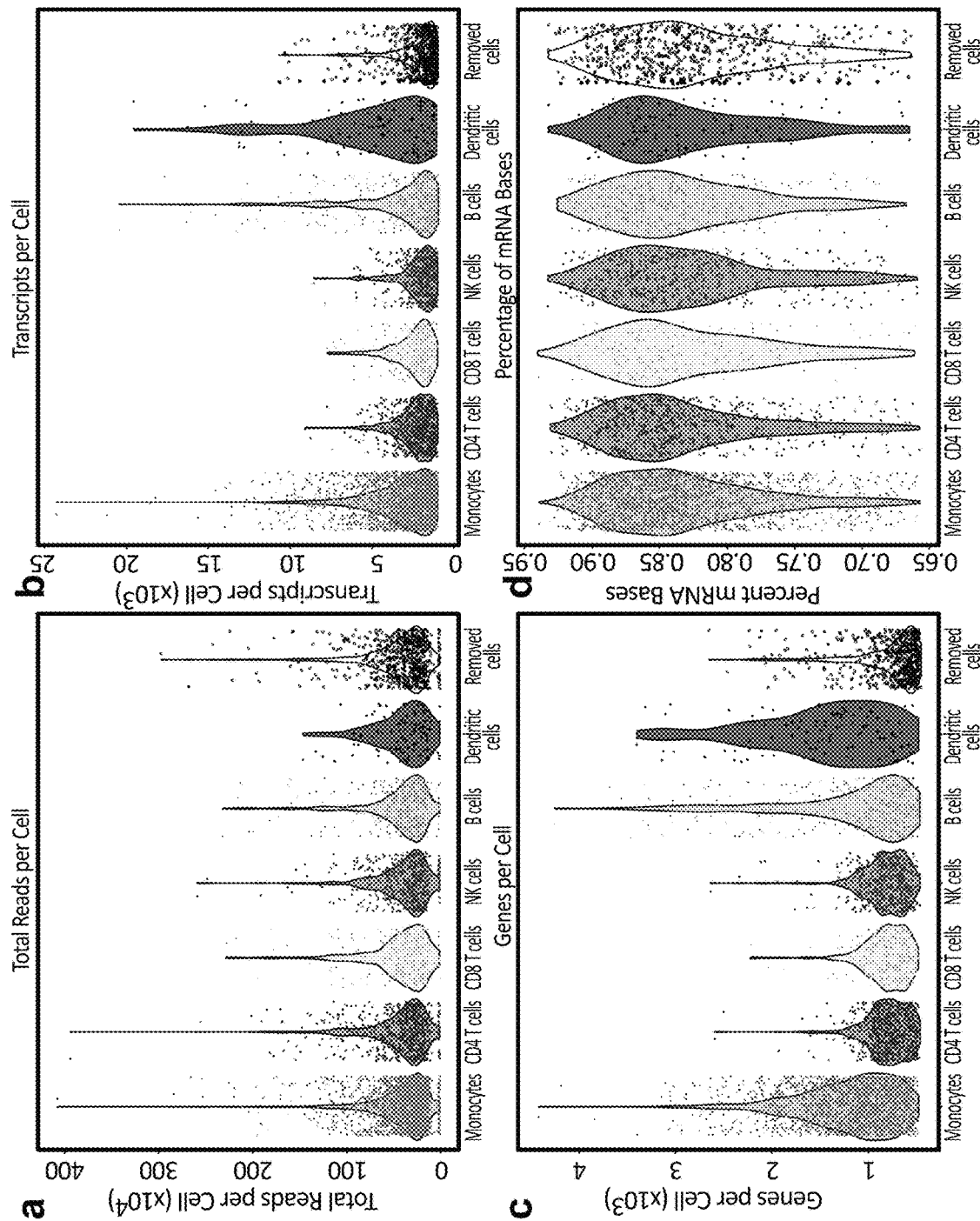

To test the portability of Seq-Well, primary human macrophages exposed to *M. tuberculosis* (H37Rv) in a BSL3 facility (Methods) were profiled. In total, 14,218 (of 40,000 possible) macrophages with greater than 1,000 mapped transcripts were recovered from a TB-exposed and an unexposed array. Unsupervised analysis of 4,638 cells with greater than 5,000 transcripts per cell revealed five distinct clusters (FIG. 12a,b, FIG. 24a,b). Two had lower transcript capture and high mitochondrial gene expression (suggestive of low quality libraries) (Illicic, T., et al., "Classification of low quality cells from single-cell RNA-seq data" (2016) Genome biology 17, 29), and were removed; the remaining three (2,560 cells) were identified in both the exposed and unexposed samples (FIG. 12a, FIG. 24c,d & FIG. 27), and likely represent distinct sub-phenotypes present in the initial culture.

Common and cluster-specific gene enrichments (Methods) were examined. Although Clusters 1 and 3 did not present strong stimulation-independent enrichments, Cluster 2 uniquely expressed several genes associated with metabolism. Within each cluster, shifts in gene expression were observed pronounced in response to *M. tuberculosis* (FIG. 2c), with common enrichments for gene sets previously observed in response to intracellular infection, LPS stimulation, and activation of TLR7/8. Cluster 1 uniquely displayed stimulation-induced shifts in several genes associated with cell growth, Cluster 3 in transcripts associated with hypoxia, and Cluster 2, again, in genes linked to metabolism. Overall, these data suggest that basal cellular heterogeneity may influence ensemble tuberculosis responses. Equally importantly, they demonstrate the ability of Seq-Well to acquire large numbers of single-cell transcriptomes in challenging experimental environments.

Seq-Well Protocol

Membrane Preparation: (1.) Place a pre-cut (22×66 mm) polycarbonate membrane onto a glass slide, carefully using a gloved finger and tweezers to separate the membrane and paper (Note 1: orientation of polycarbonate membranes not important; discard any membranes that have creases or large-scale imperfections). (2.) Place membranes onto a shelf in the plasma cleaner (Note: Place membranes on bottom shelf to reduce risk of them flying after vacuum is removed. (3.) Close the plasma cleaner door, and then turn on the main power and pump switch. To form a vacuum, ensure that the 3-way valve lever is at the 9:00 position as shown below. (4.) Allow vacuum to form for 2 minutes. Once the vacuum has formed, simultaneously turn the valve to 12:00 while turning the power to the Hi setting (shown below). Note: plasma (pink) form should be observed. (Note: The plasma should be a bright pink. If not, adjust the air valve to increase or decrease the amount of oxygen you are letting into the chamber.) (5) Treat membranes with plasma for 7 minutes. (6) Critical—After treatment, in the following order, turn the RF level valve from HIGH to OFF, then turn off the power followed by turning off the vacuum. Then slowly open the valve until you can barely hear air entering chamber (Approximate valve position shown below). Leave until door opens (~5 min). (7.) Remove slides from plasma cleaner and transfer to a 4 well plate. (Note 1: if membranes have slightly folded over, Slowly flip the membrane back using needle nosed tweezers; Note 2: if membranes have blown off the slide entirely, repeat above procedure to ensure you know which side was exposed to plasma.) (8.) Quickly pipet 5 mL of 1×PBS over the dry membrane, preventing the membrane from folding on itself (Note: gently hydrate one end of the membrane with a single drop so that it adheres to the slide before dispensing the entire volume) (9.) Remove any air bubbles underneath the membrane using wafer forceps. (10.) Membranes are now functionalized and ready for use. (Note 1: membranes solvated with 1×PBS should be used same day; Note 2: if transporting solvated membranes (e.g. between buildings), remove all by ~1 mL of PBS to prevent membranes from flipping within the dish; note 3: Alternatively, membranes can be solvated in a 2% Ficoll solution and stored dry for 2 weeks at room temperature.) When ready to use membranes, can be rehydrated with 1×PBS.

Bead Loading: (1.) Aspirate storage solution and solvate arrays with 5 mL of bead loading buffer (BLB). (2.) Place arrays under vacuum with rotation (50 rpm) for 10-15 minutes to remove air bubbles in wells. (3.) Aliquot ~110,000 beads from stock into a 1.5 mL tube and spin on a tabletop centrifuge for 10-15 seconds to form a pellet. (4.) Aspirate storage buffer and wash beads once in 500 µL of BLB. (5.) Pellet beads, aspirate BLB, and resuspend beads in 200 µL of BLB. (Note: for each array, recommended to load ~110,000 beads, e.g., when running two arrays you would aliquot ~220,000 beads, wash, and re-suspend in 400 µL of BLB.) (6.) Before loading beads, thoroughly aspirate BLB from the dish containing the array, being careful not to aspirate or dry the PDMS surface of the array. (7.) Use a 200 µL pipette to apply 200 µL containing 110,000 beads, in a drop-wise fashion, to the surface of the array. (8.) Place the loaded array(s) onto a rotator for 10 minutes (75 rpm). (9.) Thoroughly wash arrays to remove excess beads from the surface. For each wash: (a.) Position the array so that it sits in the center of the 4-well dish. (b.) Dispense 500 µL of BLB in the upper right corner of the array and 500 µL in the bottom right corner of the array (careful not to directly pipette onto the microwells, as it can dislodge beads). (c.) Using wafer forceps, push the array against the left side of the 4-well dish to create a capillary flow, which will help remove beads from the surface. (d.) Aspirate the liquid, reposition the array, and repeat on the opposite side. (10.) Repeat step 9 as necessary. Periodically examine the array under microscope to verify that no loose beads are present on the surface, as this will interfere with membrane attachment. (11.) Once excess beads have been removed from the surface, solvate the array with 5 mL of BLB and proceed to cell loading. (Notes: If continuing to cell loading immediately (i.e., within 1-5 hours), loaded arrays should be stored in 5 mL of BLB. Loaded arrays can be stored for up to 72 hours in Array Quenching Buffer.

Cell Loading (without imaging): (1) Arrays should be loaded with beads and immersed in BLB. (2) Obtain a cell or tissue sample and prepare a single cell suspension using your preferred protocol (3) While preparing your single cell suspension, aspirate the BLB from array and soak it in 5 mL of RPMI+10% FBS for 5 minutes (4) After obtaining a single cell suspension, count cells using a hemocytometer and make a new solution of 10,000 cells in 200 µL of RPMI+10% FBS (Cell Loading Solution) (5) Aspirate the RPMI+10% FBS solution, center the array in well, then load the cell loading solution in a dropwise fashion onto the surface of the array (6) Intermittently rock the array in the x & y direction for 5 minutes (to visualize membrane sealing or cell loading, pre-label cells with AF647-anti CD45 if leukocytes or another surface marker in AF647) (7) Wash arrays 4× with 5 mL of PBS to remove FBS in media—this is critical to ensure successful membrane attachment (Aspirate final PBS wash and replace with 5 mL of RPMI media (no FBS).

Cell Loading (with imaging): (1) When pre-imaging cells, cells should be loaded first as beads will obstruct view of many cells and bead autofluorescence can interfere with the signal (2) Obtain a cell or tissue sample and prepare a single cell suspension using your preferred protocol (3) Count cells using a hemocytometer and resuspend 10,000 cells in 200 µL of cold CellCover (Anacyte). (4) Incubate cells at 4° C. for 1 hour (5) After the cells have been fixed, perform antibody staining at 4° C. (Note: Some epitopes may no longer be available as a result of the fixation process) (6) Wash cells twice with 1×PBS, resuspend in 200 µL of CellCover10 buffer (pH 10+10% FBS) and place on ice. (7) Obtain empty functionalized array(s), aspirate storage solution and soak array(s) with 5 mL of CellCover10 buffer (8) Aspirate media and load fixed cells onto the array(s) in a dropwise format (9) Gently rock the array(s) in the x & y direction for 5 minutes (10) Wash array(s) twice with 5 mL of CellCover10 (pH 10+10% FBS), then solvate in 5 mL of CellCover (No FBS). (11) Place a lift slip onto the array(s), then image with a microscope (12) After imaging, wash array(s) in 5 mL of CellCover10 media (13) Immediately load beads using the bead loading protocol provided above (14) Proceed with membrane sealing.

Membrane Sealing: (1) Use wafer forceps to transfer the array(s) from media to the lid of a 4-well dish, being careful to keep the array as close to horizontal as possible (2) Use wafer forceps to remove a pre-treated membrane from the 4-well dish. (3) Gently dab away moisture from the glass slide on the paper towel until the membrane does not spontaneously change position on the glass slide (4) Carefully position the membrane on the center of the microscope slide, leaving a small (2-3 mm) membrane overhang beyond the edge of slide (5) Holding the membrane in your left hand, invert the microscope slide so that the treated surface is facing down (6) Place the overhang of the membrane in contact with the PDMS surface of the array just above the boundary of the microwells (7) Using your right hand, firmly hold down the overhang of the membrane against the PDMS surface of the array (8) Note: While maintaining pressure with your right hand to hold the membrane in place, gently apply the membrane; for optimal results, use little to no pressure while applying the membrane with the left hand; Attempts to manually seal the microwell device using pressure result in a 'squeegee' effect, effectively removing moisture from the membrane while fixing membrane creases in place). (9) After applying the membrane, carefully pry the array and membrane from the surface of the lid and transfer to an Agilent clamp (10) Tighten clamp to the point of resistance and place in a 37° C. incubator for 30 minutes (11) Repeat membrane sealing procedure if running multiple arrays.

Cell Lysis and Hybridization: (1) Remove the clamp from the incubator, and then remove the array from the Agilent clamp (2) Submerge the array with top slide still attached in 5 mL of pre-lysis buffer (5 M Guanidine thiocyanate and 1 mM EDTA) (3) Gently rock the array in pre-lysis buffer until the top glass slide lifts off (Note: time necessary for detachment of the top slide varies (10 seconds-5 minutes) (4) Once the top slide has detached, aspirate the pre-lysis buffer and add 5 mL of complete lysis buffer to the array (Note: Alternatively, 5 mL of complete lysis buffer can be prepared by adding 25 µL of 20% Sarkosyl and 50 µL of Beta-mercaptoethanol to pre-lysis buffer; use a separate waste container for lysis buffer because guanidine thiocyanate can react with bleach in TC traps to create toxic gas (5) Rock the array for 20 minutes at 50-60 rpm (6) Remove the lysis buffer and wash once with 5 mL of hybridization buffer. (7) Aspirate hybridization buffer and add another 5 mL of hybridization buffer to the array and rock for 40 minutes at 50-60 rpm (8) While array are rocking in hybridization buffer, prepare reverse transcription master mix.

Bead Removal: (1) Aspirate hybridization buffer and replace with 5 mL of wash buffer (2) rock for 3 min (3) remove membrane with fine-tipped tweezers (4) identify orientation of a lifter slip such that feet are facing upwards (5) place lifter slip(s) in a separate 4-well dish with feet oriented upwards (6) carefully transfer the array(s) to the new dish, inverting the array(s) so that the PDMS surface is in contact with the feet of the lift slips (7) transfer 3 mL of wash buffer to the dish containing the inverted array(s) (8) precisely (+/−2 grams) weigh the dish containing inverted array(s) to properly balance the centrifuge (9) Spin for 5 minutes at 1000×G. (10) After centrifugation, collect the beads and transfer them to a 15 mL conical tube for each array, if running multiple: (a) rinse the glass slide on the back of the array with wash buffer (b) invert the array and rinse the PDMS surface (c) lightly scrape the surface of the array to remove any retained beads using a microscope slide (d) remove array and rinse both sides of the lifter slips (e) collect suspended beads (10-12 mL) and transfer to a 15-mL conical tube. (11) Spin conical tube(s) for 5 minutes at 3000×G. (12) aspirate all liquid but 1 mL and transfer beads to a clean 1.5 mL centrifuge tube (13) Rinse 15 mL conical with 500 µL of wash buffer and add to the 1.5 mL tube.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for high-throughput parallel single cell biochemical analysis in a container, the method comprising providing an array container, the array container comprising:
   an array having a plurality of wells, the array comprising:
   (a) a first functionalized surface of each well, wherein the first functionalized surface comprises an affinity resin; and
   (b) a second functionalized surface of a top surface of the array, wherein the top surface is in planar configuration with the openings of the wells, and wherein the second functionalized surface provides accessible ionic functional groups, and
   a porous membrane configured to be positioned on the top surface and over the openings of the wells, wherein the porous membrane and the top surface of the array can cooperate by establishing molecular bonding so as to substantially isolate each well, or a subset of wells, from adjacent wells, and wherein isolation of each well or subset of wells comprises confining cells, macromolecules, or a combination thereof, inside the wells by sealing the loaded wells with the porous membrane, wherein the porous membrane pore size selectively isolates the cells and the macromolecules while allowing flow of liquid and/or molecules of a certain smaller size through the porous membrane.

2. The method of claim 1, wherein the array comprises at least one additional functionalized surface of each well, wherein the at least one additional functionalized surface provides for multiplexing reactions.

3. The method of claim 1, wherein the array comprises an array material comprising polydimethylsiloxane, polycarbonate, polystyrene, polymethyl-methacrylate, polyvinylidene difluoride, polyvinylchloride, polypropylene, cyclic olefin co-polymer, a glass, silicon, or polystyrene modified with dextran; and/or wherein the array comprises an array material doped with an ionic functional group anywhere from 1% to 30% (by molar basis) providing access for further modification via molecular bonding or providing charged moieties at surfaces.

4. The method of claim 1, wherein the top surface comprises an array material functionalized to an organosilane and/or provides free alcohols upon treatment; wherein the top surface comprises organosiloxane functional groups conjugated to polydimethylsiloxane; or wherein the top surface comprises functional groups conjugated to cyclic olefin co-polymer using aryl diazonium salts.

5. The method of claim 4, wherein the free alcohols are reacted with an amino-silane to create an amine functionalized surface.

6. The method of claim 1, wherein the ionic functional group is a positively charged functional group.

7. The method of claim 1, wherein the affinity resin comprises a negatively charged surface, wherein the negatively charged surface repels mRNA, and wherein the negatively charged surface enables mRNA to be captured by poly(dT) beads.

8. The method of claim 1, wherein the porous membrane is an ion exchange membrane and/or an ultrafiltration membrane, and wherein the ultrafiltration membrane comprises a weak cationic exchange surface or a polymeric surface functionalized with chitosan.

9. An array container for multiple parallel single-cell biochemical analysis, comprising
an array having a plurality of wells, wherein said array has a functionalized top surface in a planar configuration with the openings of the wells, and
a porous membrane configured to be positioned on the top surface of the array and over the openings of the wells, wherein the porous membrane and the functionalized top surface of the array can cooperate by establishing molecular bonding so as to substantially isolate each well, or a subset of wells, from adjacent wells, wherein isolation of each well or subset of wells comprises confining cells, macromolecules, or a combination thereof, inside the wells by sealing the loaded wells with the porous membrane, wherein the porous membrane pore size selectively isolates the cells and the macromolecules, while allowing flow of liquid and/or molecules of a certain smaller size through the porous membrane.

10. The array container of claim 9, wherein the array container comprises a plurality of Unique Molecular Identifiers (UMIs).

11. The array container of claim 9, wherein molecular bonding comprises one or more of covalent bonding, ion-ion bonding, dipole-dipole bonding, ion-dipole bonding, hydrogen bonding, and van der Waals bonding.

12. The array container of claim 9, wherein the molecular bonding is effective when the container is immersed in an aqueous solution.

13. The array container of claim 9, wherein the plurality of wells comprises about at least 1,000 or at least 10,000 or at least about 100,000 or at least 200,000 or at least 500,000 or up to 1,000,000 wells or about 50,000 to 1,000,000 wells.

14. The array container of claim 9, wherein the wells are micro-sized wells, nano-sized wells, or pico-sized wells; wherein the array has about 80,000 50 µm-wells, or 250,000 30 µm-wells, or 1,000,000 15 µm-wells; wherein the wells have a size less than or equal to about 50 microns on each side; and/or wherein the distance between adjacent wells is about 15 or 30 or 40 or 50 microns.

15. The array container of claim 9, wherein the well volume is equal or less than a microliter.

16. The array container of claim 9, wherein the molecular bonding between the porous membrane and the top surface of the array is reversible.

17. The array container of claim 9, wherein the top surface of the array bears a charge of a first polarity; the porous membrane bears a charge of a second polarity, the second polarity being opposite the first polarity and is hydrated; wherein the charged porous membrane is on the charged top surface of the array.

18. The array container of claim 17, wherein the first polarity is positive and the second polarity is negative.

19. The array container of claim 9, wherein the top surface comprises organosiloxane functional groups.

20. The array container of claim 9, wherein the array comprises polydimethylsiloxane (PDMS), polycarbonate (PC), polystyrene (PS), polymethyl-methacrylate (PMMA), PVDF, polyvinylchloride (PVC), polypropylene (PP), cyclic olefin co-polymer (COC), a glass, or is silicon.

21. The array container of claim 17, wherein a charge of a first polarity is induced on the top surface of the array by: plasma treating the array; and coating the top surface with an organosiloxane functional group.

22. The array container of claim 21, further comprising treating the top surface of the array with a polysaccharide.

23. The array container of claim 9, wherein the porous membrane is functionalized by a reactive functional group.

24. The array container of claim 23, wherein the top surface of the array is functionalized by a reactive functional group.

25. The array container of claim 23, wherein the top surface of the array is functionalized with an amine, an amine silane, a thiosilane, a methacrylate silane, a poly(allylamine), poly(lysine), BSA, epoxide silane, or chitosan.

26. The array container of claim 9, wherein part or all of the inside surface of the wells of the array is functionalized with a different molecule than the top surface of the array.

27. The array container of claim 9, wherein part or all of the inside surface of the wells is functionalized to activate loaded cells, capture secreted products, to make the wells hospitable to a living cell, functionalized with a hydrophilic coating, or any combination thereof.

28. The array container of claim 9, further comprising clamping the porous membrane to the array.

29. The array container of claim 9, wherein the wells have a size is less than or equal to about 50 microns on each side.

30. The array container of claim 9, wherein the array has about 50,000 to 1,000,000 wells.

31. The array container of claim 9, wherein the bonded porous membrane sustains strongly denaturing conditions, and/or retains bonded membrane porosity.

32. The array container of claim 9, wherein the porous membrane pore size is about 10-30 nm.

33. The array container of claim 9, wherein the porous membrane pore size is about 80-1000 nm.

34. The array container of claim 9, wherein the porous membrane is about 10-15 micron thick.

35. The array container of claim 9, wherein the porous membrane allows for cell culture for at least about 24 hours.

36. The array container of claim 9, wherein the porous membrane is selected from hydrophilic or hydrophobic poly(carbonate) membranes, hydrophilic or hydrophobic poly(carbonate) track etched membranes, nanoporous gold films, polyethersulfone membranes, functionalized cellulose membranes, nitrocellulose membranes, polyvinylidene difluoride (PVDF) membranes, polyacrylonitrile (PAN) membranes, polypiperazine-amide membranes, and polystyrene (PS) membranes.

37. The array container of claim 15, wherein the well volume is equal or less than a nanoliter.

38. The array container of claim 9, wherein the first functionalized surface comprises a nucleic acid or an antigen binding protein.

39. The array container of claim 9, wherein each well is configured to contain a barcoded bead.

40. The array container of claim 39, wherein the barcoded bead is a barcoded poly(dT) bead; and/or wherein the barcoded bead comprises a cell barcode and/or a unique molecular identifier (UMI).

41. The array container of claim 9, wherein the macromolecules comprise RNA, DNA, proteins, or combinations thereof.

42. The array container of claim 9, wherein the molecular bonding comprises one or more of covalent bonding, ion-ion bonding, dipole-dipole bonding, ion-dipole bonding, hydrogen bonding, and van der Waals bonding.

43. The array container of claim 9 wherein the porosity of the porous membrane is selected from porosities suitable for one or more of the following applications: protein capture after cell lysis, RNA capture after cell lysis, transcript capture after cell lysis, mammalian cell culture, protein capture trough micro-engraving, antibody staining for cytometry, and bacterial cell culture.

44. The array container of claim 10, wherein the UMIs are provided on a solid support or on a bead, or wherein the UMIs are provided directly in the wells on the inside of the wells; wherein the Unique Molecular Identifiers (UMIs) are selected so as to track experiments in the array; and/or wherein the UMIs are selected from RNA or DNA.

45. The array container of claim 22, wherein the polysaccharide is chitosan, a chitin, or cellulose.

46. The array container of claim 23, wherein the porous membrane is functionalized by an amine, an amine silane, a thiosilane, a methacrylate silane, or a poly(allylamine).

47. The array container of claim 46, wherein the porous membrane is further functionalized with one or more of maleimide, 2-iminothiolane (Traut's reagent), polyacrylic acid, and bisepoxide-PEG.

48. The array container of claim 25, wherein the top surface of the array is further functionalized with one or more of 2-iminothiolane (Traut's reagent), polyacrylic acid, epoxide-PEG, and oxidized agarose.

49. The array container of claim 27, wherein the hydrophilic coating comprises a hydroxyl, amine, and/or carboxyl functionality.

* * * * *